United States Patent
Schneider et al.

(10) Patent No.: US 8,404,214 B2
(45) Date of Patent: Mar. 26, 2013

(54) PMMA BINDING PEPTIDES

(75) Inventors: Eberhard Schneider, Denkte (DE);
Gregor Schurmann, Hannover (DE);
Peter Wagner, Braunschweig (DE);
Hong Wang, Kennett Square, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 258 days.

(21) Appl. No.: 12/778,180

(22) Filed: May 12, 2010

(65) Prior Publication Data
US 2010/0298241 A1    Nov. 25, 2010

Related U.S. Application Data

(60) Provisional application No. 61/179,831, filed on May 20, 2009.

(51) Int. Cl.
*A61K 8/00* (2006.01)
(52) U.S. Cl. .................................................. 424/7.1
(58) Field of Classification Search .................. None
See application file for complete search history.

(56) References Cited

U.S. PATENT DOCUMENTS

| | | | |
|---|---|---|---|
| 7,220,405 B2 | 5/2007 | Huang et al. | |
| 7,285,264 B2 | 10/2007 | O'Brien et al. | |
| 7,341,604 B2 | 3/2008 | Rothe et al. | |
| 7,632,919 B2 | 12/2009 | Cunningham et al. | |
| 7,700,716 B2 | 4/2010 | Cunningham et al. | |
| 7,709,601 B2 | 5/2010 | Cunningham et al. | |
| 8,206,693 B2 * | 6/2012 | Schneider et al. | 424/70.1 |
| 2005/0050656 A1 | 3/2005 | Huang et al. | |
| 2005/0054752 A1 | 3/2005 | O'Brien et al. | |
| 2005/0226839 A1 | 10/2005 | Huang et al. | |
| 2005/0249682 A1 | 11/2005 | Buseman-Williams et al. | |
| 2006/0171885 A1 | 8/2006 | Janssen et al. | |
| 2006/0199206 A1 | 9/2006 | Wang et al. | |
| 2007/0065387 A1 | 3/2007 | Beck et al. | |
| 2007/0110686 A1 | 5/2007 | Lowe et al. | |
| 2007/0141628 A1 | 6/2007 | Cunningham et al. | |
| 2007/0196305 A1 | 8/2007 | Wang et al. | |
| 2007/0249805 A1 | 10/2007 | Ittel et al. | |
| 2007/0264720 A1 | 11/2007 | Cunningham et al. | |
| 2007/0265431 A1 | 11/2007 | Cunningham et al. | |
| 2007/0274931 A9 | 11/2007 | Buseman-Williams et al. | |
| 2008/0175798 A1 | 7/2008 | Beck et al. | |
| 2008/0206809 A1 | 8/2008 | DeCarolis et al. | |
| 2008/0280810 A1 | 11/2008 | O'Brien et al. | |
| 2009/0029902 A1 | 1/2009 | Cunningham et al. | |
| 2010/0158822 A1 | 6/2010 | Fahnestock et al. | |
| 2010/0158837 A1 | 6/2010 | Fahnestock et al. | |

FOREIGN PATENT DOCUMENTS

| | | |
|---|---|---|
| WO | 2004000257 A2 | 12/2003 |
| WO | 2004048399 A2 | 6/2004 |

OTHER PUBLICATIONS

Gold, Larry, mRNA display: Diversity matters during in vitro selection, PNAS, Apr. 24, 2001, pp. 4825-4826, vol. 98, No. 9.
U.S. Appl. No. 12/785,694, filed May 24, 2010, Schneider et al.
U.S. Appl. No. 12/778,167, filed May 12, 2010, Schneider et al.
U.S. Appl. No. 12/778,174, filed May 12, 2010, Schneider et al.
U.S. Appl. No. 12/778,178, filed May 12, 2010, Schneider et al.
U.S. Appl. No. 12/778,169, filed May 12, 2010, Schneider et al.
U.S. Appl. No. 12/778,186, filed May 12, 2010, Schneider et al.
U.S. Appl. No. 12/778,194, filed May 12, 2010, Schneider et al.
U.S. Appl. No. 12/778,199, filed May 12, 2010, Schneider et al.

* cited by examiner

*Primary Examiner* — Thomas Heard

(57) ABSTRACT

Peptides are provided that have binding affinity for polymethyl methacrylate (PMMA). The polymethyl methacrylate-binding peptides may be used to prepare peptide-based reagents suitable for use in a variety of applications. The peptide-based reagents may be used to couple benefit agents to a PMMA polymer surface or may be used to couple a benefit agent comprising a PMMA polymer surface to a target surface, such as a body surface.

7 Claims, No Drawings

SEQUENCE LISTING

<160> NUMBER OF SEQ ID NOS: 474

<210> SEQ ID NO 1
<211> LENGTH: 27
<212> TYPE: PRT
<213> ORGANISM: artificial sequence
<220> FEATURE:
<223> OTHER INFORMATION: synthetic construct

<400> SEQUENCE: 1

Phe Leu His Gly Leu Ile His Gly Trp Tyr Ser Leu Trp Met Trp Met
1               5                   10                  15

Leu Ser Trp Pro Tyr Met Val Trp Trp Val Phe
            20                  25

<210> SEQ ID NO 2
<211> LENGTH: 27
<212> TYPE: PRT
<213> ORGANISM: artificial sequence
<220> FEATURE:
<223> OTHER INFORMATION: synthetic construct

<400> SEQUENCE: 2

Phe Leu His Gly Leu Ile His Gly Trp Tyr Ser Leu Trp Met Trp Ile
1               5                   10                  15

Leu Ser Trp Pro Tyr Met Val Trp Trp Val Phe
            20                  25

<210> SEQ ID NO 3
<211> LENGTH: 27
<212> TYPE: PRT
<213> ORGANISM: artificial sequence
<220> FEATURE:
<223> OTHER INFORMATION: synthetic construct

<400> SEQUENCE: 3

Phe Met His Gly Leu Ile His Gly Trp Tyr Ser Leu Trp Met Trp Met
1               5                   10                  15

Leu Ser Trp Pro Tyr Met Val Trp Trp Val Phe
            20                  25

<210> SEQ ID NO 4
<211> LENGTH: 27
<212> TYPE: PRT
<213> ORGANISM: artificial sequence
<220> FEATURE:
<223> OTHER INFORMATION: synthetic construct

<400> SEQUENCE: 4

Phe Leu His Gly Leu Ile His Gly Trp Tyr Ser Leu Trp Met Trp Met
1               5                   10                  15

Leu Ser Trp Pro Tyr Met Val Trp Trp Val Leu
            20                  25

<210> SEQ ID NO 5
<211> LENGTH: 27
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa = Leu or Met
<220> FEATURE:

```
<221> NAME/KEY: MISC_FEATURE
<222> LOCATION: (16)..(16)
<223> OTHER INFORMATION: Xaa = Met or Iso
<220> FEATURE:
<221> NAME/KEY: MISC_FEATURE
<222> LOCATION: (27)..(27)
<223> OTHER INFORMATION: Xaa = Phe or Leu

<400> SEQUENCE: 5

Phe Xaa His Gly Leu Ile His Gly Trp Tyr Ser Leu Trp Met Trp Xaa
 1               5                  10                  15

Leu Ser Trp Pro Tyr Met Val Trp Trp Val Xaa
            20                  25

<210> SEQ ID NO 6
<211> LENGTH: 27
<212> TYPE: PRT
<213> ORGANISM: artificial sequence
<220> FEATURE:
<223> OTHER INFORMATION: synthetic construct

<400> SEQUENCE: 6

Gly Trp Gln Arg Ile Trp Gln Ser Ile Leu Cys Trp Met Tyr Phe Pro
 1               5                  10                  15

Leu Cys Leu Trp Met Glu Trp Tyr Arg Ala Ile
            20                  25

<210> SEQ ID NO 7
<211> LENGTH: 27
<212> TYPE: PRT
<213> ORGANISM: artificial sequence
<220> FEATURE:
<223> OTHER INFORMATION: synthetic construct

<400> SEQUENCE: 7

Gly Trp Gln Arg Ile Trp Gln Ser Ile Leu Cys Trp Met Tyr Leu Pro
 1               5                  10                  15

Leu Cys Leu Trp Met Glu Trp Tyr Arg Ala Ile
            20                  25

<210> SEQ ID NO 8
<211> LENGTH: 27
<212> TYPE: PRT
<213> ORGANISM: artificial sequence
<220> FEATURE:
<223> OTHER INFORMATION: synthetic construct

<400> SEQUENCE: 8

Gly Trp Gln Arg Ile Trp Gln Ser Ile Phe Cys Trp Met Tyr Phe Pro
 1               5                  10                  15

Leu Cys Leu Trp Met Glu Trp Tyr Arg Ala Ile
            20                  25

<210> SEQ ID NO 9
<211> LENGTH: 27
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (10)..(10)
<223> OTHER INFORMATION: Xaa = Leu or Phe
<220> FEATURE:
<221> NAME/KEY: MISC_FEATURE
<222> LOCATION: (15)..(15)
<223> OTHER INFORMATION: Xaa = Leu or Phe
```

-continued

```
<400> SEQUENCE: 9

Gly Trp Gln Arg Ile Trp Gln Ser Ile Xaa Cys Trp Met Tyr Xaa Pro
1               5                   10                  15

Leu Cys Leu Trp Met Glu Trp Tyr Arg Ala Ile
            20                  25

<210> SEQ ID NO 10
<211> LENGTH: 27
<212> TYPE: PRT
<213> ORGANISM: artificial sequence
<220> FEATURE:
<223> OTHER INFORMATION: synthetic construct

<400> SEQUENCE: 10

Gly Ser Glu Thr Tyr Leu Tyr Trp Ser Trp Trp Trp Leu Tyr Leu Trp
1               5                   10                  15

Tyr Trp Pro Phe Trp Tyr Met Trp Ala Gly Met
            20                  25

<210> SEQ ID NO 11
<211> LENGTH: 27
<212> TYPE: PRT
<213> ORGANISM: artificial sequence
<220> FEATURE:
<223> OTHER INFORMATION: synthetic construct

<400> SEQUENCE: 11

Gly Ser Glu Thr Tyr Leu Tyr Trp Ser Trp Trp Trp Leu Tyr Leu Trp
1               5                   10                  15

Tyr Trp Pro Phe Trp Tyr Val Trp Ala Gly Met
            20                  25

<210> SEQ ID NO 12
<211> LENGTH: 27
<212> TYPE: PRT
<213> ORGANISM: artificial sequence
<220> FEATURE:
<223> OTHER INFORMATION: synthetic construct

<400> SEQUENCE: 12

Gly Ser Glu Thr Tyr Leu Tyr Trp Ser Trp Cys Trp Leu Tyr Leu Trp
1               5                   10                  15

Tyr Trp Pro Phe Arg Tyr Met Trp Ala Gly Met
            20                  25

<210> SEQ ID NO 13
<211> LENGTH: 27
<212> TYPE: PRT
<213> ORGANISM: artificial sequence
<220> FEATURE:
<223> OTHER INFORMATION: synthetic construct

<400> SEQUENCE: 13

Gly Ser Glu Thr Tyr Leu Tyr Trp Ser Trp Trp Trp Leu Tyr Ser Trp
1               5                   10                  15

Tyr Trp Pro Phe Trp Tyr Met Trp Ala Gly Met
            20                  25

<210> SEQ ID NO 14
<211> LENGTH: 27
<212> TYPE: PRT
<213> ORGANISM: artificial sequence
<220> FEATURE:
<223> OTHER INFORMATION: synthetic construct
<220> FEATURE:
```

```
<221> NAME/KEY: MISC_FEATURE
<222> LOCATION: (11)..(11)
<223> OTHER INFORMATION: Xaa = Trp or Cys
<220> FEATURE:
<221> NAME/KEY: MISC_FEATURE
<222> LOCATION: (15)..(15)
<223> OTHER INFORMATION: Xaa = Leu or Ser
<220> FEATURE:
<221> NAME/KEY: MISC_FEATURE
<222> LOCATION: (21)..(21)
<223> OTHER INFORMATION: Xaa = Trp or Arg
<220> FEATURE:
<221> NAME/KEY: MISC_FEATURE
<222> LOCATION: (23)..(23)
<223> OTHER INFORMATION: Xaa = Val or Met

<400> SEQUENCE: 14

Gly Ser Glu Thr Tyr Leu Tyr Trp Ser Trp Xaa Trp Leu Tyr Xaa Trp
1               5                   10                  15

Tyr Trp Pro Phe Xaa Tyr Xaa Trp Ala Gly Met
            20                  25

<210> SEQ ID NO 15
<211> LENGTH: 27
<212> TYPE: PRT
<213> ORGANISM: artificial sequence
<220> FEATURE:
<223> OTHER INFORMATION: synthetic construct

<400> SEQUENCE: 15

Met Trp His Gly Leu Trp Leu Trp Met Ala Leu Tyr Trp Trp Met Thr
1               5                   10                  15

Trp Ser Trp Phe Leu Trp Pro Phe Arg Val Ile
            20                  25

<210> SEQ ID NO 16
<211> LENGTH: 27
<212> TYPE: PRT
<213> ORGANISM: artificial sequence
<220> FEATURE:
<223> OTHER INFORMATION: synthetic construct

<400> SEQUENCE: 16

Met Trp His Gly Leu Trp Leu Trp Met Ala Leu Tyr Trp Trp Met Thr
1               5                   10                  15

Trp Ser Trp Phe Leu Trp Pro Phe Trp Val Ile
            20                  25

<210> SEQ ID NO 17
<211> LENGTH: 27
<212> TYPE: PRT
<213> ORGANISM: artificial sequence
<220> FEATURE:
<223> OTHER INFORMATION: synthetic construct

<400> SEQUENCE: 17

Met Trp Tyr Gly Leu Trp Leu Trp Met Ala Leu Tyr Trp Trp Met Thr
1               5                   10                  15

Trp Ser Trp Phe Leu Trp Pro Phe Arg Val Ile
            20                  25

<210> SEQ ID NO 18
<211> LENGTH: 27
<212> TYPE: PRT
<213> ORGANISM: artificial sequence
<220> FEATURE:
<223> OTHER INFORMATION: synthetic construct
<220> FEATURE:
```

```
<221> NAME/KEY: MISC_FEATURE
<222> LOCATION: (3)..(3)
<223> OTHER INFORMATION: Xaa = His orTyr
<220> FEATURE:
<221> NAME/KEY: MISC_FEATURE
<222> LOCATION: (25)..(25)
<223> OTHER INFORMATION: Xaa = Trp or Arg

<400> SEQUENCE: 18

Met Trp Xaa Gly Leu Trp Leu Trp Met Ala Leu Tyr Trp Trp Met Thr
1               5                   10                  15

Trp Ser Trp Phe Leu Trp Pro Phe Xaa Val Ile
            20                  25

<210> SEQ ID NO 19
<211> LENGTH: 27
<212> TYPE: PRT
<213> ORGANISM: artificial sequence
<220> FEATURE:
<223> OTHER INFORMATION: synthetic construct

<400> SEQUENCE: 19

Ile Gly Trp Trp Leu Leu Arg Tyr Trp Leu Tyr Leu Gln Trp Lys Leu
1               5                   10                  15

Tyr Val Trp Trp Phe Ser Val Leu Trp Thr Phe
            20                  25

<210> SEQ ID NO 20
<211> LENGTH: 27
<212> TYPE: PRT
<213> ORGANISM: artificial sequence
<220> FEATURE:
<223> OTHER INFORMATION: synthetic construct

<400> SEQUENCE: 20

Ile Gly Trp Trp Leu Leu Arg Tyr Trp Leu Tyr Leu Gln Trp Lys Leu
1               5                   10                  15

Tyr Ala Trp Trp Phe Ser Val Leu Trp Thr Phe
            20                  25

<210> SEQ ID NO 21
<211> LENGTH: 27
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (18)..(18)
<223> OTHER INFORMATION: Xaa = Val or Ala

<400> SEQUENCE: 21

Ile Gly Trp Trp Leu Leu Arg Tyr Trp Leu Tyr Leu Gln Trp Lys Leu
1               5                   10                  15

Tyr Xaa Trp Trp Phe Ser Val Leu Trp Thr Phe
            20                  25

<210> SEQ ID NO 22
<211> LENGTH: 27
<212> TYPE: PRT
<213> ORGANISM: artificial sequence
<220> FEATURE:
<223> OTHER INFORMATION: synthetic construct

<400> SEQUENCE: 22

Arg Leu Asp Ser Trp Ile Phe Gln Thr Trp Leu Met Trp Ile Trp Met
1               5                   10                  15
```

```
Val Trp Pro Trp Leu Trp Pro Phe Trp Trp Leu
            20                  25

<210> SEQ ID NO 23
<211> LENGTH: 26
<212> TYPE: PRT
<213> ORGANISM: artificial sequence
<220> FEATURE:
<223> OTHER INFORMATION: synthetic construct

<400> SEQUENCE: 23

Leu Asp Ser Trp Ile Phe Gln Thr Trp Leu Met Trp Ile Trp Met Val
1               5                   10                  15

Trp Pro Trp Leu Trp Pro Phe Trp Trp Leu
            20                  25

<210> SEQ ID NO 24
<211> LENGTH: 27
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa = Arg or a single amino acid deletion

<400> SEQUENCE: 24

Xaa Leu Asp Ser Trp Ile Phe Gln Thr Trp Leu Met Trp Ile Trp Met
1               5                   10                  15

Val Trp Pro Trp Leu Trp Pro Phe Trp Trp Leu
            20                  25

<210> SEQ ID NO 25
<211> LENGTH: 27
<212> TYPE: PRT
<213> ORGANISM: artificial sequence
<220> FEATURE:
<223> OTHER INFORMATION: synthetic construct

<400> SEQUENCE: 25

Val Trp Trp Thr Phe Phe Gly Trp Phe Tyr Trp Leu Trp Ala Met Trp
1               5                   10                  15

Trp Asn Val Ser Leu Ala Leu Trp Glu Trp Val
            20                  25

<210> SEQ ID NO 26
<211> LENGTH: 27
<212> TYPE: PRT
<213> ORGANISM: artificial sequence
<220> FEATURE:
<223> OTHER INFORMATION: synthetic construct

<400> SEQUENCE: 26

Val Trp Trp Ala Phe Phe Gly Trp Phe Tyr Trp Leu Trp Ala Met Trp
1               5                   10                  15

Trp Asn Val Ser Leu Ala Leu Trp Glu Trp Val
            20                  25

<210> SEQ ID NO 27
<211> LENGTH: 27
<212> TYPE: PRT
<213> ORGANISM: artificial sequence
<220> FEATURE:
<223> OTHER INFORMATION: synthetic construct
<220> FEATURE:
```

-continued

<221> NAME/KEY: MISC_FEATURE
<222> LOCATION: (4)..(4)
<223> OTHER INFORMATION: Xaa = Thr or Ala

<400> SEQUENCE: 27

Val Trp Trp Xaa Phe Phe Gly Trp Phe Tyr Trp Leu Trp Ala Met Trp
1               5                   10                  15

Trp Asn Val Ser Leu Ala Leu Trp Glu Trp Val
            20                  25

<210> SEQ ID NO 28
<211> LENGTH: 27
<212> TYPE: PRT
<213> ORGANISM: artificial sequence
<220> FEATURE:
<223> OTHER INFORMATION: synthetic construct

<400> SEQUENCE: 28

Val Val Pro Leu Met Trp Val Tyr Trp Trp Val Phe Met Trp Gly Trp
1               5                   10                  15

Pro Met Val Phe Trp Tyr Thr Trp Trp Ala Ala
            20                  25

<210> SEQ ID NO 29
<211> LENGTH: 27
<212> TYPE: PRT
<213> ORGANISM: artificial sequence
<220> FEATURE:
<223> OTHER INFORMATION: synthetic construct

<400> SEQUENCE: 29

Phe Ser Ser Arg Asp Phe Leu Gly Tyr Trp Ile Ser Trp Leu Met Trp
1               5                   10                  15

Pro Tyr Phe Val Leu Trp Arg Trp Leu Met His
            20                  25

<210> SEQ ID NO 30
<211> LENGTH: 27
<212> TYPE: PRT
<213> ORGANISM: artificial sequence
<220> FEATURE:
<223> OTHER INFORMATION: synthetic construct

<400> SEQUENCE: 30

Arg Ser Gly Leu Lys Arg Lys Val Leu Arg His Val Trp Thr Val Met
1               5                   10                  15

Trp Thr Met Gly Ser Trp Leu His Gly Ser Leu
            20                  25

<210> SEQ ID NO 31
<211> LENGTH: 27
<212> TYPE: PRT
<213> ORGANISM: artificial sequence
<220> FEATURE:
<223> OTHER INFORMATION: synthetic construct

<400> SEQUENCE: 31

Phe Trp Tyr Gly Leu Trp Leu Phe Trp Trp Trp His Thr Trp Phe Val
1               5                   10                  15

Trp Arg Thr Leu Trp Tyr Trp Met Val Trp Leu
20 25

<210> SEQ ID NO 32
<211> LENGTH: 27
<212> TYPE: PRT

<213> ORGANISM: artificial sequence
<220> FEATURE:
<223> OTHER INFORMATION: synthetic construct

<400> SEQUENCE: 32

Thr Leu Trp Thr Phe Tyr Trp Leu Ser Trp Ala Trp Tyr Met Pro Leu
1               5                   10                  15
Trp Pro Trp Trp Leu Tyr Trp Leu Met Trp Gly
            20                  25

<210> SEQ ID NO 33
<211> LENGTH: 27
<212> TYPE: PRT
<213> ORGANISM: artificial sequence
<220> FEATURE:
<223> OTHER INFORMATION: synthetic construct

<400> SEQUENCE: 33

Leu Leu Trp Leu Phe Trp Trp Pro Trp Leu Trp Trp Leu Cys Val Thr
1               5                   10                  15
Gln Trp Ser Tyr Glu Met Gly Met Gly Trp Trp
            20                  25

<210> SEQ ID NO 34
<211> LENGTH: 27
<212> TYPE: PRT
<213> ORGANISM: artificial sequence
<220> FEATURE:
<223> OTHER INFORMATION: synthetic construct

<400> SEQUENCE: 34

His Phe Trp Ala Trp Tyr Ile Glu Trp Leu Arg Trp Tyr Leu Tyr Val
1               5                   10                  15
Pro Leu Val Val Phe Arg Trp Phe Val Gly Phe
            20                  25

<210> SEQ ID NO 35
<211> LENGTH: 27
<212> TYPE: PRT
<213> ORGANISM: artificial sequence
<220> FEATURE:
<223> OTHER INFORMATION: synthetic construct

<400> SEQUENCE: 35

Tyr Val Leu Phe Phe Met Ala Val Trp Trp Pro Trp Trp Leu Leu Met
1               5                   10                  15
Trp Ile Trp Gln Asn Leu Met Thr Met Thr Thr
            20                  25

<210> SEQ ID NO 36
<211> LENGTH: 17
<212> TYPE: PRT
<213> ORGANISM: artificial sequence
<220> FEATURE:
<223> OTHER INFORMATION: N terminal constant region - synthetic

<400> SEQUENCE: 36

Met His His His His His His Ser Gly Ser Ser Ser Gly Ser Gly Ser
1               5                   10                  15
Gly

<210> SEQ ID NO 37
<211> LENGTH: 16
<212> TYPE: PRT
<213> ORGANISM: artificial sequence

```
<220> FEATURE:
<223> OTHER INFORMATION: C terminal constant region - synthetic

<400> SEQUENCE: 37

Thr Ser Gly Gly Ser Ser Gly Ser Ser Leu Gly Val Ala Ser Ala Ile
1               5                   10                  15

<210> SEQ ID NO 38
<211> LENGTH: 28
<212> TYPE: RNA
<213> ORGANISM: artificial sequence
<220> FEATURE:
<223> OTHER INFORMATION: Synthetic oligonucleotide linker
<220> FEATURE:
<221> NAME/KEY: misc_feature
<222> LOCATION: (1)..(10)
<223> OTHER INFORMATION: 2'-O-methylation

<400> SEQUENCE: 38
uagcggaugc aaaaaaaaaa aaaaaaaa                                          28

<210> SEQ ID NO 39
<211> LENGTH: 42
<212> TYPE: DNA
<213> ORGANISM: artificial sequence
<220> FEATURE:
<223> OTHER INFORMATION: primer

<400> SEQUENCE: 39
taatacgact catagggaca attactattt acaattacaa tg                          42

<210> SEQ ID NO 40
<211> LENGTH: 39
<212> TYPE: DNA
<213> ORGANISM: artificial sequence
<220> FEATURE:
<223> OTHER INFORMATION: primer

<400> SEQUENCE: 40
aattaaatag cggatgctac accaagacta gaaccgctg                              39

<210> SEQ ID NO 41
<211> LENGTH: 8
<212> TYPE: PRT
<213> ORGANISM: Artificial Sequence
<220> FEATURE:
<223> OTHER INFORMATION: Caspase 3 cleavage site

<400> SEQUENCE: 41

Leu Glu Ser Gly Asp Glu Val Asp
1               5

<210> SEQ ID NO 42
<211> LENGTH: 12
<212> TYPE: PRT
<213> ORGANISM: Artificial sequence
<220> FEATURE:
<223> OTHER INFORMATION: Polymethylmethacrylate binding peptides

<400> SEQUENCE: 42

Ile Pro Trp Trp Asn Ile Arg Ala Pro Leu Asn Ala
1               5                   10

<210> SEQ ID NO 43
<211> LENGTH: 12
<212> TYPE: PRT
<213> ORGANISM: Artificial Sequence
<220> FEATURE:
```

<223> OTHER INFORMATION: Polymethylmethacrylate-binding peptide

<400> SEQUENCE: 43

Thr Ala Val Met Asn Val Val Asn Asn Gln Leu Ser
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 44

Val Pro Trp Trp Ala Pro Ser Lys Leu Ser Met Gln
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 45

Met Val Met Ala Pro His Thr Pro Arg Ala Arg Ser
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 46

Thr Tyr Pro Asn Trp Ala His Leu Leu Ser His Tyr
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 47

Thr Pro Trp Trp Arg Ile Thr
1               5

<210> SEQ ID NO 48
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 48

Asp Leu Thr Leu Pro Phe His
1               5

<210> SEQ ID NO 49
<211> LENGTH: 7
<212> TYPE: PRT
<213> ORGANISM: Artificial Sequence
<220> FEATURE:
<223> OTHER INFORMATION: Polymethylmethacrylate-binding peptide

```
<400> SEQUENCE: 49

Gly Thr Ser Ile Pro Ala Met
1               5

<210> SEQ ID NO 50
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 50

His His Lys His Val Val Ala
1               5

<210> SEQ ID NO 51
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 51

His His His Lys His Phe Met
1               5

<210> SEQ ID NO 52
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 52

His His His Arg His Gln Gly
1               5

<210> SEQ ID NO 53
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 53

His His Trp His Ala Pro Arg
1               5

<210> SEQ ID NO 54
<211> LENGTH: 12
<212> TYPE: PRT
<213> ORGANISM: Artificial Sequence
<220> FEATURE:
<223> OTHER INFORMATION: PMMA-binding peptide

<400> SEQUENCE: 54

Ala Pro Trp His Leu Ser Ser Gln Tyr Ser Gly Thr
1               5                   10

<210> SEQ ID NO 55
<211> LENGTH: 14
<212> TYPE: PRT
<213> ORGANISM: Artificial Sequence
<220> FEATURE:
<223> OTHER INFORMATION: PMMA-binding peptide

<400> SEQUENCE: 55
```

```
Gly Tyr Cys Leu Arg Val Asp Glu Pro Thr Val Cys Ser Gly
1               5                   10
```

<210> SEQ ID NO 56
<211> LENGTH: 15
<212> TYPE: PRT
<213> ORGANISM: Artificial Sequence
<220> FEATURE:
<223> OTHER INFORMATION: PMMA-binding peptide

<400> SEQUENCE: 56

```
His Ile His Pro Ser Asp Asn Phe Pro His Lys Asn Arg Thr His
1               5                   10                  15
```

<210> SEQ ID NO 57
<211> LENGTH: 20
<212> TYPE: PRT
<213> ORGANISM: Artificial Sequence
<220> FEATURE:
<223> OTHER INFORMATION: PMMA-binding peptide

<400> SEQUENCE: 57

```
His Thr His His Asp Thr His Lys Pro Trp Pro Thr Asp Asp His Arg
1               5                   10                  15

Asn Ser Ser Val
            20
```

<210> SEQ ID NO 58
<211> LENGTH: 20
<212> TYPE: PRT
<213> ORGANISM: Artificial Sequence
<220> FEATURE:
<223> OTHER INFORMATION: PMMA-binding peptide

<400> SEQUENCE: 58

```
Pro Glu Asp Arg Pro Ser Arg Thr Asn Ala Leu His His Asn Ala His
1               5                   10                  15

His His Asn Ala
            20
```

<210> SEQ ID NO 59
<211> LENGTH: 15
<212> TYPE: PRT
<213> ORGANISM: Artificial Sequence
<220> FEATURE:
<223> OTHER INFORMATION: PMMA-binding peptide

<400> SEQUENCE: 59

```
Thr Pro His Asn His Ala Thr Thr Asn His His Ala Gly Lys Lys
1               5                   10                  15
```

<210> SEQ ID NO 60
<211> LENGTH: 15
<212> TYPE: PRT
<213> ORGANISM: Artificial Sequence
<220> FEATURE:
<223> OTHER INFORMATION: PMMA-binding peptide

<400> SEQUENCE: 60

```
Glu Met Val Lys Asp Ser Asn Gln Arg Asn Thr Arg Ile Ser Ser
1               5                   10                  15
```

<210> SEQ ID NO 61
<211> LENGTH: 12
<212> TYPE: PRT
<213> ORGANISM: Artificial Sequence
<220> FEATURE:

<223> OTHER INFORMATION: PMMA-binding peptide

<400> SEQUENCE: 61

His Tyr Ser Arg Tyr Asn Pro Gly Pro His Pro Leu
1               5                   10

<210> SEQ ID NO 62
<211> LENGTH: 12
<212> TYPE: PRT
<213> ORGANISM: Artificial Sequence
<220> FEATURE:
<223> OTHER INFORMATION: PMMA-binding peptide

<400> SEQUENCE: 62

Ile Asp Thr Phe Tyr Met Ser Thr Met Ser His Ser
1               5                   10

<210> SEQ ID NO 63
<211> LENGTH: 20
<212> TYPE: PRT
<213> ORGANISM: Artificial Sequence
<220> FEATURE:
<223> OTHER INFORMATION: PMMA-binding peptide

<400> SEQUENCE: 63

Pro Met Lys Glu Ala Thr His Pro Val Pro Pro His Lys His Ser Glu
1               5                   10                  15

Thr Pro Thr Ala
            20

<210> SEQ ID NO 64
<211> LENGTH: 12
<212> TYPE: PRT
<213> ORGANISM: Artificial Sequence
<220> FEATURE:
<223> OTHER INFORMATION: PMMA-binding peptide

<400> SEQUENCE: 64

Tyr Gln Thr Ser Ser Pro Ala Lys Gln Ser Val Gly
1               5                   10

<210> SEQ ID NO 65
<211> LENGTH: 15
<212> TYPE: PRT
<213> ORGANISM: Artificial Sequence
<220> FEATURE:
<223> OTHER INFORMATION: PMMA-binding peptide

<400> SEQUENCE: 65

His Leu Pro Ser Tyr Gln Ile Thr Gln Thr His Ala Gln Tyr Arg
1               5                   10                  15

<210> SEQ ID NO 66
<211> LENGTH: 20
<212> TYPE: PRT
<213> ORGANISM: Artificial Sequence
<220> FEATURE:
<223> OTHER INFORMATION: PMMA-binding peptide

<400> SEQUENCE: 66

Thr Thr Pro Lys Thr Thr Tyr His Gln Ser Arg Ala Pro Val Thr Ala
1               5                   10                  15

Met Ser Glu Val
            20

<210> SEQ ID NO 67

```
<211> LENGTH: 15
<212> TYPE: PRT
<213> ORGANISM: Artificial Sequence
<220> FEATURE:
<223> OTHER INFORMATION: PMMA-binding peptide

<400> SEQUENCE: 67

Asp Arg Ile His His Lys Ser His His Val Thr Thr Asn His Phe
1               5                   10                  15

<210> SEQ ID NO 68
<211> LENGTH: 12
<212> TYPE: PRT
<213> ORGANISM: Artificial Sequence
<220> FEATURE:
<223> OTHER INFORMATION: PMMA-binding peptide

<400> SEQUENCE: 68

Trp Ala Pro Glu Lys Asp Tyr Met Gln Leu Met Lys
1               5                   10

<210> SEQ ID NO 69
<211> LENGTH: 12
<212> TYPE: PRT
<213> ORGANISM: Artificial sequence
<220> FEATURE:
<223> OTHER INFORMATION: Polypropylene-binding peptides

<400> SEQUENCE: 69

Thr Ser Asp Ile Lys Ser Arg Ser Pro His His Arg
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Polypropylenebinding peptide

<400> SEQUENCE: 70

His Thr Gln Asn Met Arg Met Tyr Glu Pro Trp Phe
1               5                   10

<210> SEQ ID NO 71
<211> LENGTH: 7
<212> TYPE: PRT
<213> ORGANISM: Artificial Sequence
<220> FEATURE:
<223> OTHER INFORMATION: Polypropylene-binding peptide

<400> SEQUENCE: 71

Leu Pro Pro Gly Ser Leu Ala
1               5

<210> SEQ ID NO 72
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 72

Met Pro Ala Val Met Ser Ser Ala Gln Val Pro Arg
1               5                   10

<210> SEQ ID NO 73
<211> LENGTH: 12
<212> TYPE: PRT
```

```
<213> ORGANISM: Artificial Sequence
<220> FEATURE:
<223> OTHER INFORMATION: Polypropylene-binding peptide

<400> SEQUENCE: 73

Asn Gln Ser Phe Leu Pro Leu Asp Phe Pro Phe Arg
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 74

Ser Ile Leu Ser Thr Met Ser Pro His Gly Ala Thr
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 75

Ser Met Lys Tyr Ser His Ser Thr Ala Pro Ala Leu
1               5                   10

<210> SEQ ID NO 76
<211> LENGTH: 12
<212> TYPE: PRT
<213> ORGANISM: Artificial sequence
<220> FEATURE:
<223> OTHER INFORMATION: Polytetrafluoroethylene-binding peptides

<400> SEQUENCE: 76

Glu Ser Ser Tyr Ser Trp Ser Pro Ala Arg Leu Ser
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 77

Gly Pro Leu Lys Leu Leu His Ala Trp Trp Gln Pro
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Polytetrafluoroethylene-binding peptide

<400> SEQUENCE: 78

Asn Ala Leu Thr Arg Pro Val
1               5

<210> SEQ ID NO 79
<211> LENGTH: 7
<212> TYPE: PRT
<213> ORGANISM: Artificial Sequence
<220> FEATURE:
```

```
<223> OTHER INFORMATION: Polytetrafluoroethylene-binding peptide

<400> SEQUENCE: 79

Ser Ala Pro Ser Ser Lys Asn
1               5

<210> SEQ ID NO 80
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 80

Ser Val Ser Val Gly Met Lys Pro Ser Pro Arg Pro
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 81

Ser Tyr Tyr Ser Leu Pro Pro Ile Phe His Ile Pro
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 82

Thr Phe Thr Pro Tyr Ser Ile Thr His Ala Leu Leu
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 83

Thr Met Gly Phe Thr Ala Pro Arg Phe Pro His Tyr
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 84

Thr Asn Pro Phe Pro Pro Pro Pro Ser Ser Pro Ala
1               5                   10

<210> SEQ ID NO 85
<211> LENGTH: 12
<212> TYPE: PRT
<213> ORGANISM: Artificial sequence
<220> FEATURE:
<223> OTHER INFORMATION: Polyethylene-binding peptides
```

-continued

<400> SEQUENCE: 85

His Asn Lys Ser Ser Pro Leu Thr Ala Ala Leu Pro
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 86

Leu Pro Pro Trp Lys His Lys Thr Ser Gly Val Ala
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 87

Leu Pro Trp Trp Leu Arg Asp Ser Tyr Leu Leu Pro
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 88

Val Pro Trp Trp Lys His Pro Pro Leu Pro Val Pro
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 89

His His Lys Gln Trp His Asn His Pro His His Ala
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 90

His Ile Phe Ser Ser Trp His Gln Met Trp His Arg
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 91

```
Trp Pro Ala Trp Lys Thr His Pro Ile Leu Arg Met
1               5                   10
```

<210> SEQ ID NO 92
<211> LENGTH: 7
<212> TYPE: PRT
<213> ORGANISM: Artificial sequence
<220> FEATURE:
<223> OTHER INFORMATION: Nylon-binding peptides

<400> SEQUENCE: 92

```
Lys Thr Pro Pro Thr Arg Pro
1               5
```

<210> SEQ ID NO 93
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 93

```
Val Ile Asn Pro Asn Leu Asp
1               5
```

<210> SEQ ID NO 94
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 94

```
Lys Val Trp Ile Val Ser Thr
1               5
```

<210> SEQ ID NO 95
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 95

```
Ala Glu Pro Val Ala Met Leu
1               5
```

<210> SEQ ID NO 96
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 96

```
Ala Glu Leu Val Ala Met Leu
1               5
```

<210> SEQ ID NO 97
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 97

```
His Ser Leu Arg Leu Asp Trp
1               5
```

-continued

```
<210> SEQ ID NO 98
<211> LENGTH: 13
<212> TYPE: PRT
<213> ORGANISM: Artificial sequence
<220> FEATURE:
<223> OTHER INFORMATION: Polystyrene-binding peptide

<400> SEQUENCE: 98

Thr Ser Thr Ala Ser Pro Thr Met Gln Ser Lys Ile Arg
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Polystyrene-binding peptide

<400> SEQUENCE: 99

Lys Arg Asn His Trp Gln Arg Met His Leu Ser Ala
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Polystyrene-binding peptide

<400> SEQUENCE: 100

Ser His Ala Thr Pro Pro Gln Gly Leu Gly Pro Gln
1               5                   10

<210> SEQ ID NO 101
<211> LENGTH: 20
<212> TYPE: PRT
<213> ORGANISM: artificial sequence
<220> FEATURE:
<223> OTHER INFORMATION: cellulose acetate-binding peptide

<400> SEQUENCE: 101

Ala Thr Thr Pro Pro Ser Gly Lys Ala Ala His Ser Ala Ala Arg
1               5                   10                  15

Gln Lys Gly Asn
            20

<210> SEQ ID NO 102
<211> LENGTH: 15
<212> TYPE: PRT
<213> ORGANISM: artificial sequence
<220> FEATURE:
<223> OTHER INFORMATION: cellulose acetate-binding peptide

<400> SEQUENCE: 102

Asp Thr Ile His Pro Asn Lys Met Lys Ser Pro Ser Ser Pro Leu
1               5                   10                  15

<210> SEQ ID NO 103
<211> LENGTH: 20
<212> TYPE: PRT
<213> ORGANISM: artificial sequence
<220> FEATURE:
<223> OTHER INFORMATION: cellulose aceteate-binding peptide

<400> SEQUENCE: 103

Asn Gly Asn Asn His Thr Asp Ile Pro Asn Arg Ser Ser Tyr Thr Gly
```

```
                1               5                  10                 15

Gly Ser Phe Ala
                20

<210> SEQ ID NO 104
<211> LENGTH: 15
<212> TYPE: PRT
<213> ORGANISM: ARTIFICIAL SEQUENCE
<220> FEATURE:
<223> OTHER INFORMATION: cellulose acetate-binding peptide

<400> SEQUENCE: 104

Ser Asp Glu Thr Gly Pro Gln Ile Pro His Arg Arg Pro Thr Trp
1               5                  10                 15

<210> SEQ ID NO 105
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 105

Met Pro Pro Pro Leu Met Gln
1               5

<210> SEQ ID NO 106
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 106

Phe His Glu Asn Trp Pro Ser
1               5

<210> SEQ ID NO 107
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 107

Arg Thr Ala Pro Thr Thr Pro Leu Leu Leu Ser Leu
1               5                  10

<210> SEQ ID NO 108
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 108

Trp His Leu Ser Trp Ser Pro Val Pro Leu Pro Thr
1               5                  10

<210> SEQ ID NO 109
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 109
```

Pro His Ala Arg Leu Val Gly
1               5

<210> SEQ ID NO 110
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 110

Asn Ile Pro Tyr His His Pro
1               5

<210> SEQ ID NO 111
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 111

Thr Thr Met Pro Ala Ile Pro
1               5

<210> SEQ ID NO 112
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 112

His Asn Leu Pro Pro Arg Ser
1               5

<210> SEQ ID NO 113
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 113

Ala His Lys Thr Gln Met Gly Val Arg Gln Pro Ala
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 114

Ala Asp Asn Val Gln Met Gly Val Ser His Thr Pro
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 115

Ala His Asn Ala Gln Met Gly Val Ser His Pro Pro
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 116

Ala Asp Tyr Val Gly Met Gly Val Ser His Arg Pro
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 117

Ser Val Ser Val Gly Met Lys Pro Ser Pro Arg Pro
1               5                   10

<210> SEQ ID NO 118
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 118

Tyr Pro Asn Thr Ala Leu Val
1               5

<210> SEQ ID NO 119
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 119

Val Ala Thr Arg Ile Val Ser
1               5

<210> SEQ ID NO 120
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 120

His Ser Leu Lys Asn Ser Met Leu Thr Val Met Ala
1               5                   10

<210> SEQ ID NO 121
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 121

Asn Tyr Pro Thr Gln Ala Pro
1               5

```
<210> SEQ ID NO 122
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 122

Lys Cys Cys Tyr Ser Val Gly
1               5

<210> SEQ ID NO 123
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 123

Arg His Asp Leu Asn Thr Trp Leu Pro Pro Val Lys
1               5                   10

<210> SEQ ID NO 124
<211> LENGTH: 12
<212> TYPE: PRT
<213> ORGANISM: artificial sequence
<220> FEATURE:
<223> OTHER INFORMATION: synthetic construct

<400> SEQUENCE: 124

Glu Ile Ser Leu Pro Ala Lys Leu Pro Ser Ala Ser
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 125

Ser Asp Tyr Val Gly Met Arg Pro Ser Pro Arg His
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 126

Ser Asp Tyr Val Gly Met Arg Leu Ser Pro Ser Gln
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 127

Ser Val Ser Val Gly Ile Gln Pro Ser Pro Arg Pro
1               5                   10

<210> SEQ ID NO 128
<211> LENGTH: 12
```

```
<212> TYPE: PRT
<213> ORGANISM: Artificial Sequence
<220> FEATURE:
<223> OTHER INFORMATION: Pigment-binding peptide

<400> SEQUENCE: 128

Tyr Val Ser Val Gly Ile Lys Pro Ser Pro Arg Pro
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 129

Tyr Val Cys Glu Gly Ile His Pro Cys Pro Arg Pro
1               5                   10

<210> SEQ ID NO 130
<211> LENGTH: 12
<212> TYPE: PRT
<213> ORGANISM: artificial sequence
<220> FEATURE:
<223> OTHER INFORMATION: synthetic pigment binding peptide

<400> SEQUENCE: 130

Trp Ala Pro Glu Lys Asp His Met Gln Leu Met Lys
1               5                   10

<210> SEQ ID NO 131
<211> LENGTH: 12
<212> TYPE: PRT
<213> ORGANISM: artificial sequence
<220> FEATURE:
<223> OTHER INFORMATION: Iron oxide-binding peptide

<400> SEQUENCE: 131

Trp Ala Pro Glu Lys Asp Tyr Met Gln Leu Met Lys
1               5                   10

<210> SEQ ID NO 132
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 132

Cys Pro Leu Asp Thr Pro Thr His Lys Thr Lys His Glu Tyr Lys Thr
1               5                   10                  15

Arg Cys Arg His
            20

<210> SEQ ID NO 133
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 133

Asp His Asp His Pro Arg Leu His Lys Arg Gln Glu Lys Ser Glu His
1               5                   10                  15

Leu His
```

<210> SEQ ID NO 134
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 134

Asp Ser His His Asn His His Lys Gln Asp Ser Arg Pro Gln His Arg
1               5                   10                  15

Lys Thr Pro Asn
            20

<210> SEQ ID NO 135
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 135

Glu Gly Gly Asn Ala Pro His His Lys Pro His His Arg Lys His
1               5                   10                  15

<210> SEQ ID NO 136
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 136

His Asp Ser His Arg Pro Leu Thr Gln His Gly His Arg His Ser His
1               5                   10                  15

Val Pro

<210> SEQ ID NO 137
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 137

His Asp Ser Asn His Cys Ser His Ser Thr Arg Arg Pro Asn Cys Ala
1               5                   10                  15

Arg Thr

<210> SEQ ID NO 138
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 138

Ala Thr Arg Val Asp Asn Thr Pro Ala Ser Asn Pro Pro Ser Leu
1               5                   10                  15

<210> SEQ ID NO 139
<211> LENGTH: 15
<212> TYPE: PRT
<213> ORGANISM: artificial sequence
<220> FEATURE:
<223> OTHER INFORMATION: Iron oxide-binding peptide -continued

```
<400> SEQUENCE: 139

Asp Gly Ile Lys Pro Phe His Leu Met Thr Pro Thr Leu Ala Asn
1               5                   10                  15

<210> SEQ ID NO 140
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 140

Asp Ile Thr Pro Pro Gly Ser Thr His His Arg Lys Pro His Arg His
1               5                   10                  15

Gln His

<210> SEQ ID NO 141
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 141

Asp Asn Leu Trp Pro Gln Pro Leu Asn Val Glu Asp Asp Arg Tyr
1               5                   10                  15

<210> SEQ ID NO 142
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 142

Glu Asn Glu Lys His Arg His Asn Thr His Glu Ala Leu His Ser His
1               5                   10                  15

Phe Lys

<210> SEQ ID NO 143
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 143

Gly Ala Ile Trp Pro Ala Ser Ser Ala Leu Met Thr Glu His Asn Pro
1               5                   10                  15

Thr Asp Asn His
            20

<210> SEQ ID NO 144
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 144

Gly Asp Thr Asn Gln Asp Thr Val Met Trp Tyr Tyr Thr Val Asn
1               5                   10                  15

<210> SEQ ID NO 145
<211> LENGTH: 15
```

```
<212> TYPE: PRT
<213> ORGANISM: artificial sequence
<220> FEATURE:
<223> OTHER INFORMATION: Iron oxide-binding peptide

<400> SEQUENCE: 145

His Asn Gly Pro Tyr Gly Met Leu Ser Thr Gly Lys Ile His Phe
1               5                   10                  15

<210> SEQ ID NO 146
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 146

Leu Asp Gly Gly Tyr Arg Asp Thr Pro Asp Asn Tyr Leu Lys Gly
1               5                   10                  15

<210> SEQ ID NO 147
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 147

Leu His Thr Lys Thr Glu Asn Ser His Thr Asn Met Lys Thr Thr
1               5                   10                  15

<210> SEQ ID NO 148
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 148

Asn Ala Gln Tyr Asp Pro Pro Thr Leu Asn Lys Gly Ala Val Arg Lys
1               5                   10                  15

Ala Ala Ser Thr
            20

<210> SEQ ID NO 149
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 149

Asn Gly Asn Asn His Thr Asp Ile Pro Asn Arg Ser Ser Tyr Thr
1               5                   10                  15

<210> SEQ ID NO 150
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 150

Gln Ser Thr Asn His His His Pro His Ala Lys His Pro Arg Val Asn
1               5                   10                  15

Thr His
```

<210> SEQ ID NO 151
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 151

Ser Asn Asn Asp Tyr Val Gly Thr Tyr Pro Ala Thr Ala Ile Gln
1               5                   10                  15

<210> SEQ ID NO 152
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 152

Ser Thr Gln His Asn Leu His Asp Arg Asn Ile Tyr Phe Val Ser
1               5                   10                  15

<210> SEQ ID NO 153
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 153

Thr Ala Asn Asn Lys Thr Pro Ala Gly Ala Pro Asn Ala Ala Val Gly
1               5                   10                  15

Leu Ala Gln Arg
            20

<210> SEQ ID NO 154
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 154

Thr Glu Pro Thr Arg Ile Ser Asn Tyr Arg Ser Ile Pro Asn Asp
1               5                   10                  15

<210> SEQ ID NO 155
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 155

Thr His Asn Pro Arg Glu His Ala Arg His His His Asn Glu Tyr
1               5                   10                  15

Lys His

<210> SEQ ID NO 156
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 156

```
Thr His Pro Pro Cys Trp Tyr Glu Thr Asn Cys Ile Val Gln Glu
1               5                   10                  15

<210> SEQ ID NO 157
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 157

Thr Thr Asn Pro His Lys Pro Ala Ser His His Asp His Arg Pro
1               5                   10                  15

Ala Leu Arg His
            20

<210> SEQ ID NO 158
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 158

Trp Leu Val Ala Asp Asn Ala Thr Asp Gly His Ser His Gln Lys
1               5                   10                  15

<210> SEQ ID NO 159
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 159

Tyr Thr Asp Ser Met Ser Asp Gln Thr Pro Glu Phe Ala Lys Tyr
1               5                   10                  15

<210> SEQ ID NO 160
<211> LENGTH: 27
<212> TYPE: PRT
<213> ORGANISM: artificial sequence
<220> FEATURE:
<223> OTHER INFORMATION: Clay-binding peptide

<400> SEQUENCE: 160

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25

<210> SEQ ID NO 161
<211> LENGTH: 27
<212> TYPE: PRT
<213> ORGANISM: artificial sequence
<220> FEATURE:
<223> OTHER INFORMATION: Clay-binding peptide

<400> SEQUENCE: 161

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25

<210> SEQ ID NO 162
<211> LENGTH: 27
```

```
<212> TYPE: PRT
<213> ORGANISM: artificial sequence
<220> FEATURE:
<223> OTHER INFORMATION: Clay-binding peptide

<400> SEQUENCE: 162

Lys Lys Ser Asn Lys Gly His His Pro Ser Ser Lys Gly Lys Gly Pro
1               5                   10                  15

Pro Trp Ser Glu Trp Asp Lys Lys Asn Gly Pro
            20                  25

<210> SEQ ID NO 163
<211> LENGTH: 27
<212> TYPE: PRT
<213> ORGANISM: artificial sequence
<220> FEATURE:
<223> OTHER INFORMATION: Clay-binding peptide

<400> SEQUENCE: 163

Lys Lys Ser Asn Lys Gly Pro His Pro Ser Ser Lys Gly Lys Gly Pro
1               5                   10                  15

Pro Trp Ser Glu Trp Asp Lys Lys Asn Gly Pro
            20                  25

<210> SEQ ID NO 164
<211> LENGTH: 22
<212> TYPE: PRT
<213> ORGANISM: artificial sequence
<220> FEATURE:
<223> OTHER INFORMATION: Clay-binding peptide

<400> SEQUENCE: 164

Val Gly Arg His His Ser Lys Ala Lys Gln Lys Arg Pro His Gly Gly
1               5                   10                  15

Lys Gly Gln Asn Lys Asn
            20

<210> SEQ ID NO 165
<211> LENGTH: 22
<212> TYPE: PRT
<213> ORGANISM: artificial sequence
<220> FEATURE:
<223> OTHER INFORMATION: Clay-binding peptide

<400> SEQUENCE: 165

Val Gly Arg His His Pro Lys Ala Lys Gln Lys Arg Pro His Gly Gly
1               5                   10                  15

Lys Gly Gln Asn Lys Asn
            20

<210> SEQ ID NO 166
<211> LENGTH: 17
<212> TYPE: PRT
<213> ORGANISM: artificial sequence
<220> FEATURE:
<223> OTHER INFORMATION: Clay-binding peptide

<400> SEQUENCE: 166

Gly Arg Arg Pro Arg Ala Arg Gly Arg Ser Arg Arg Gly Ser Thr Lys
1               5                   10                  15

Thr

<210> SEQ ID NO 167
<211> LENGTH: 19
<212> TYPE: PRT
```

-continued

```
<213> ORGANISM: artificial sequence
<220> FEATURE:
<223> OTHER INFORMATION: Clay-binding peptide

<400> SEQUENCE: 167

Leu Gly Val Ile Arg Asn His Val Val Arg Gly Arg Arg His His Gln
1               5                   10                  15

His Val Arg

<210> SEQ ID NO 168
<211> LENGTH: 27
<212> TYPE: PRT
<213> ORGANISM: artificial sequence
<220> FEATURE:
<223> OTHER INFORMATION: Clay-binding peptide

<400> SEQUENCE: 168

Gln Pro Gly Arg Pro Thr Glu Val His Pro Glu Leu Val Arg Lys Ser
1               5                   10                  15

Ala Tyr Leu Val Asn Pro Ser Glu Asp Ile Arg
            20                  25

<210> SEQ ID NO 169
<211> LENGTH: 27
<212> TYPE: PRT
<213> ORGANISM: artificial sequence
<220> FEATURE:
<223> OTHER INFORMATION: Clay-binding peptide

<400> SEQUENCE: 169

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
            20                  25

<210> SEQ ID NO 170
<211> LENGTH: 27
<212> TYPE: PRT
<213> ORGANISM: artificial sequence
<220> FEATURE:
<223> OTHER INFORMATION: Clay-binding peptide

<400> SEQUENCE: 170

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25

<210> SEQ ID NO 171
<211> LENGTH: 27
<212> TYPE: PRT
<213> ORGANISM: artificial sequence
<220> FEATURE:
<223> OTHER INFORMATION: Clay-binding peptide

<400> SEQUENCE: 171

Val Gly Glu Lys Pro Arg Arg Lys Ser Lys Gly Ala Lys Ala Lys Lys
1               5                   10                  15

Ala Arg Thr Lys Glu Glu Lys Leu Pro Lys Asn
            20                  25

<210> SEQ ID NO 172
<211> LENGTH: 27
<212> TYPE: PRT
<213> ORGANISM: artificial sequence
```

```
<220> FEATURE:
<223> OTHER INFORMATION: Clay-binding peptide

<400> SEQUENCE: 172

Asn Lys Gly His Lys Gln Ser Gly Ser Pro Arg His Ser Asn Lys Lys
1               5                   10                  15

Glu Lys Lys Thr Gln Gln Lys Arg Gly Gln Pro
            20                  25

<210> SEQ ID NO 173
<211> LENGTH: 27
<212> TYPE: PRT
<213> ORGANISM: artificial sequence
<220> FEATURE:
<223> OTHER INFORMATION: Clay-binding peptide

<400> SEQUENCE: 173

His Trp Gly Ser Gln His Lys Thr Gly Leu Arg Asn His Lys Arg Ser
1               5                   10                  15

Arg Arg Asp Ser Leu Gly Lys Arg Gly Thr Asp
            20                  25

<210> SEQ ID NO 174
<211> LENGTH: 27
<212> TYPE: PRT
<213> ORGANISM: artificial sequence
<220> FEATURE:
<223> OTHER INFORMATION: Clay-binding peptide

<400> SEQUENCE: 174

Lys Gly Trp Gly Ser Ser Ser Gly Pro Pro Gly Leu Thr Gly Lys Ala
1               5                   10                  15

Leu Gly Lys Gly Arg Leu Lys Pro Lys Lys Lys
            20                  25

<210> SEQ ID NO 175
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 175

Arg Asn Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 176
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 176

Arg Asn Asn Lys Gly Ser Lys Lys Val Asp Asp Lys Arg Arg Lys Thr
1               5                   10                  15

Val His Asn Thr Lys Ser Arg Ala Lys His Ser
            20                  25

<210> SEQ ID NO 177
<211> LENGTH: 27
<212> TYPE: PRT
<213> ORGANISM: artificial sequence
```

<220> FEATURE:
<223> OTHER INFORMATION: Calcium carbonate binding peptide

<400> SEQUENCE: 177

Arg Asp Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 178
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 178

Arg Asn Asn Lys Gly Ser Lys Lys Val Asp Asp Lys Arg Arg Lys Thr
1               5                   10                  15

Val His Ser Thr Lys Ser Arg Ala Lys Tyr Ser
            20                  25

<210> SEQ ID NO 179
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 179

Arg Asn Asn Lys Gly Ser Arg Lys Val Asp Asp Lys Arg Arg Lys Thr
1               5                   10                  15

Val His Asn Thr Lys Ser Arg Ala Lys Tyr Ser
            20                  25

<210> SEQ ID NO 180
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 180

Arg Asn Asn Lys Gly Ser Lys Lys Ala Asp Asp Lys Arg Arg Lys Thr
1               5                   10                  15

Val His Ser Thr Lys Ser Arg Ala Lys Tyr Ser
            20                  25

<210> SEQ ID NO 181
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 181

Arg Asn Asn Lys Gly Ser Lys Lys Val Asp Asp Lys Arg Arg Lys Ala
1               5                   10                  15

Val His Asn Lys Lys Ser Arg Ala Lys Tyr Ser
            20                  25

<210> SEQ ID NO 182
<211> LENGTH: 27
<212> TYPE: PRT
<213> ORGANISM: artificial sequence

```
<220> FEATURE:
<223> OTHER INFORMATION: Calcium carbonate binding peptide

<400> SEQUENCE: 182

Arg Asn Asn Lys Gly Ser Lys Lys Val Asp Asp Lys Arg Arg Lys Thr
1               5                   10                  15

Val His Asn Thr Arg Ser Arg Ala Lys Tyr Ser
            20                  25

<210> SEQ ID NO 183
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 183

Arg Asn Asn Lys Gly Ser Lys Lys Val Asp Asp Lys Arg Arg Lys Thr
1               5                   10                  15

Val His Asn Thr Lys Ser Arg Ala Lys Phe Ser
            20                  25

<210> SEQ ID NO 184
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 184

Gln Arg Arg Lys Leu Arg His Pro Lys Glu Lys Trp Phe Gly Trp Ser
1               5                   10                  15

Glu Lys Lys Val Ile Lys Lys Trp Ser Arg Lys
            20                  25

<210> SEQ ID NO 185
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (23)..(23)
<223> OTHER INFORMATION: Xaa = any naturally occurring amino acid

<400> SEQUENCE: 185

Gln Arg Arg Lys Phe Arg His Pro Lys Glu Lys Trp Phe Gly Trp Ser
1               5                   10                  15

Glu Lys Lys Val Ile Lys Xaa Asn Gly Arg Pro
            20                  25

<210> SEQ ID NO 186
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 186

His Lys Arg Leu Val Gln Asn Lys Pro His Arg Thr Arg Lys Ile Glu
1               5                   10                  15

Gly Trp Ile Lys His Met Val Lys Arg Gln His
            20                  25
```

```
<210> SEQ ID NO 187
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 187

Thr Arg Gly His Ile Met Arg Pro Cys Trp Ile Gly Ala Met Lys Gln
1               5                   10                  15

Gly Val Lys Lys Lys Arg Thr Pro Gly Trp Arg
            20                  25

<210> SEQ ID NO 188
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 188

Trp Lys Val Lys Arg Arg Met Val Thr Arg Thr Tyr Glu Phe Met Gly
1               5                   10                  15

Lys Lys Pro Cys Met Met Leu Thr Lys Arg Leu
            20                  25

<210> SEQ ID NO 189
<211> LENGTH: 26
<212> TYPE: PRT
<213> ORGANISM: artificial sequence
<220> FEATURE:
<223> OTHER INFORMATION: Calcium carbonate binding peptide

<400> SEQUENCE: 189

Lys Lys Ser Asn Lys Gly His His Ser Lys Ala Lys Gln Lys Arg Pro
1               5                   10                  15

His Gly Gly Lys Ala Gln Asn Lys Asn Thr
            20                  25

<210> SEQ ID NO 190
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 190

Arg Ala His Lys Glu Arg Phe Val Val Arg Gln Ile Gly Arg Ser Gln
1               5                   10                  15

Gly Tyr Lys Thr Trp Gln Cys Val Arg Val Ala
            20                  25

<210> SEQ ID NO 191
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 191

Ser Gln Lys Pro Lys Gly His Lys Val Lys Val Val Lys Leu Cys
1               5                   10                  15

Lys Arg Pro Tyr Trp Arg Met Leu Asn Thr Ala
            20                  25
```

<210> SEQ ID NO 192
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (11)..(11)
<223> OTHER INFORMATION: Xaa = any naturally occurring amino acid

<400> SEQUENCE: 192

Asn His Gly Cys Pro Val Asn Trp Lys Val Xaa Asn Pro Pro Arg Gly
1               5                   10                  15

Trp Gln Arg Leu Asn His Cys Lys Trp Trp Asn
            20                  25

<210> SEQ ID NO 193
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 193

Arg Asn Ser Arg His Lys Glu Trp Arg Arg Tyr Lys Arg Thr His Val
1               5                   10                  15

His Ser His Glu Phe Tyr His Val Glu Cys Trp
            20                  25

<210> SEQ ID NO 194
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 194

His Arg Ser Glu Lys Pro Lys Asn Val Asn Tyr Lys Arg Gly Tyr Trp
1               5                   10                  15

Glu Arg Gly Asn Gln Lys Lys His Gly Pro Gly
            20                  25

<210> SEQ ID NO 195
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 195

His Glu Arg Thr Arg Arg Gly Lys Pro Asp Arg Gln Lys Thr Thr His
1               5                   10                  15

Glu Lys Arg Arg Gln Gly Leu Trp Ile Phe Met
            20                  25

<210> SEQ ID NO 196
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 196

Pro Trp Gly Thr Asn Lys Arg Gln Lys His Lys Val His Glu Ala Lys
1               5                   10                  15

```
Ala Leu Lys Lys Ser Leu Trp Tyr Ser Asn Ser
            20                  25

<210> SEQ ID NO 197
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 197

Arg Arg Gly Val Val Leu Cys His Thr His Arg Asn Lys Arg Ile Arg
1               5                   10                  15

Leu Ala Tyr Ser Val Thr Lys Lys Ala Trp Ala
            20                  25

<210> SEQ ID NO 198
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 198

Glu Arg Ile Arg Trp Arg Arg Leu Ser Ala Glu Ile Arg Ala His Lys
1               5                   10                  15

Trp Ser Val Leu Lys Phe Arg Leu Ser Cys Met
            20                  25

<210> SEQ ID NO 199
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 199

Lys Thr Lys Glu Lys Lys Lys Glu Val Leu His Lys Lys Ser Leu
1               5                   10                  15

Ser Leu Val Leu Leu Ala Asp Leu Trp Arg Leu
            20                  25

<210> SEQ ID NO 200
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 200

Leu Gly Lys Lys His Lys Gln His Ser Lys Val Gly His Gly Lys Leu
1               5                   10                  15

Ser Thr Arg Phe Leu Arg Arg Ser Lys Leu Phe
            20                  25

<210> SEQ ID NO 201
<211> LENGTH: 20
<212> TYPE: PRT
<213> ORGANISM: artificial sequence
<220> FEATURE:
<223> OTHER INFORMATION: Silica-binding peptide

<400> SEQUENCE: 201

Ala Glu Ala Lys Arg His Pro Val Val Pro Leu His Glu Gln His Gly
1               5                   10                  15
```

```
His His Glu Leu
            20

<210> SEQ ID NO 202
<211> LENGTH: 18
<212> TYPE: PRT
<213> ORGANISM: artificial sequence
<220> FEATURE:
<223> OTHER INFORMATION: Silica-binding peptide

<400> SEQUENCE: 202

Ala Pro Gln Thr Trp Asn Arg Pro His Pro Gly His Pro Asn Val His
1               5                   10                  15

Thr Arg

<210> SEQ ID NO 203
<211> LENGTH: 20
<212> TYPE: PRT
<213> ORGANISM: artificial sequence
<220> FEATURE:
<223> OTHER INFORMATION: Silica-binding peptide

<400> SEQUENCE: 203

Ala Thr Thr Pro Pro Ser Gly Lys Ala Ala Ala His Ser Ala Ala Arg
1               5                   10                  15

Gln Lys Gly Asn
            20

<210> SEQ ID NO 204
<211> LENGTH: 20
<212> TYPE: PRT
<213> ORGANISM: artificial sequence
<220> FEATURE:
<223> OTHER INFORMATION: Silica-binding peptide

<400> SEQUENCE: 204

Asp Gly Arg Pro Asp Asn Pro Lys His Gln Gln Ser Tyr Asn Arg Gln
1               5                   10                  15

Leu Pro Arg Gln
            20

<210> SEQ ID NO 205
<211> LENGTH: 20
<212> TYPE: PRT
<213> ORGANISM: artificial sequence
<220> FEATURE:
<223> OTHER INFORMATION: Silica-binding peptide

<400> SEQUENCE: 205

Asp His Asn Asn Arg Gln His Ala Val Glu Val Arg Glu Asn Lys Thr
1               5                   10                  15

His Thr Ala Arg
            20

<210> SEQ ID NO 206
<211> LENGTH: 20
<212> TYPE: PRT
<213> ORGANISM: artificial sequence
<220> FEATURE:
<223> OTHER INFORMATION: Silica-binding peptide

<400> SEQUENCE: 206

Gly Pro Glu Pro Arg Ala Leu Asn Pro Lys Arg His Met Asp Pro Ala
1               5                   10                  15

Thr Gln Ile Arg
```

20

<210> SEQ ID NO 207
<211> LENGTH: 15
<212> TYPE: PRT
<213> ORGANISM: artificial sequence
<220> FEATURE:
<223> OTHER INFORMATION: Silica-binding peptide

<400> SEQUENCE: 207

His Asp His His Gln Thr His Asn Val Leu His Gly Met Lys Lys
1               5                   10                  15

<210> SEQ ID NO 208
<211> LENGTH: 18
<212> TYPE: PRT
<213> ORGANISM: artificial sequence
<220> FEATURE:
<223> OTHER INFORMATION: Silica-binding peptide

<400> SEQUENCE: 208

His His Asp Arg Ala Glu Pro Arg Gly Met Ala Ala Thr Leu Ala Gln
1               5                   10                  15

Thr Ile

<210> SEQ ID NO 209
<211> LENGTH: 20
<212> TYPE: PRT
<213> ORGANISM: artificial sequence
<220> FEATURE:
<223> OTHER INFORMATION: Silica-binding peptide

<400> SEQUENCE: 209

His His Asn His Met Thr Gly Ala Asp Asn Pro Ile Phe His Asn Asn
1               5                   10                  15

Thr Ala His Arg
            20

<210> SEQ ID NO 210
<211> LENGTH: 18
<212> TYPE: PRT
<213> ORGANISM: artificial sequence
<220> FEATURE:
<223> OTHER INFORMATION: Silica-binding peptide

<400> SEQUENCE: 210

His Asn His Ala Gln Met Leu Arg Pro Glu Pro Thr Gly Ile Ser His
1               5                   10                  15

Lys Asn

<210> SEQ ID NO 211
<211> LENGTH: 20
<212> TYPE: PRT
<213> ORGANISM: artificial sequence
<220> FEATURE:
<223> OTHER INFORMATION: Silica-binding peptide

<400> SEQUENCE: 211

His Thr Asn Asp Asn Gly Gln Ser Thr Pro Arg Arg Asp Pro Pro Ala
1               5                   10                  15

Phe Gln Arg Lys
            20

<210> SEQ ID NO 212
<211> LENGTH: 18

-continued

```
<212> TYPE: PRT
<213> ORGANISM: artificial sequence
<220> FEATURE:
<223> OTHER INFORMATION: Silica-binding peptide

<400> SEQUENCE: 212

His Thr Asn His His Tyr Asp Gln Lys Met His Gly Pro Leu Pro Thr
1               5                   10                  15

Pro Tyr

<210> SEQ ID NO 213
<211> LENGTH: 20
<212> TYPE: PRT
<213> ORGANISM: artificial sequence
<220> FEATURE:
<223> OTHER INFORMATION: Silica-binding peptide

<400> SEQUENCE: 213

Leu Asn Ser Met Ser Asp Lys His His Gly His Gln Asn Thr Ala Thr
1               5                   10                  15

Arg Asn Gln His
            20

<210> SEQ ID NO 214
<211> LENGTH: 20
<212> TYPE: PRT
<213> ORGANISM: artificial sequence
<220> FEATURE:
<223> OTHER INFORMATION: Silica-binding peptide

<400> SEQUENCE: 214

Met His Lys Pro Asn Asn Pro Asp Thr His Arg Ser Thr Pro Ser Pro
1               5                   10                  15

Leu Gly Lys Ser
            20

<210> SEQ ID NO 215
<211> LENGTH: 18
<212> TYPE: PRT
<213> ORGANISM: artificial sequence
<220> FEATURE:
<223> OTHER INFORMATION: Silica-binding peptide

<400> SEQUENCE: 215

Asn Phe Pro Val Tyr Asp Thr Thr His His Gly Gly His Arg Ser Lys
1               5                   10                  15

Leu His

<210> SEQ ID NO 216
<211> LENGTH: 20
<212> TYPE: PRT
<213> ORGANISM: artificial sequence
<220> FEATURE:
<223> OTHER INFORMATION: Silica-binding peptide

<400> SEQUENCE: 216

Asn Val His Pro Gln Ser Glu Asn Thr Asn Thr Thr Arg Pro His Lys
1               5                   10                  15

Ser Thr Gln Arg
            20

<210> SEQ ID NO 217
<211> LENGTH: 18
<212> TYPE: PRT
<213> ORGANISM: artificial sequence
```

-continued

```
<220> FEATURE:
<223> OTHER INFORMATION: Silica-binding peptide

<400> SEQUENCE: 217

Gln His Gly Met His Ser Pro Asn Leu Gly Ala Arg Met Asn Ala Thr
1               5                   10                  15

Pro His

<210> SEQ ID NO 218
<211> LENGTH: 20
<212> TYPE: PRT
<213> ORGANISM: artificial sequence
<220> FEATURE:
<223> OTHER INFORMATION: Silica-binding peptide

<400> SEQUENCE: 218

Arg Pro Asn Asp Thr His His Pro Gly Lys Cys Asp Thr His Ala Val
1               5                   10                  15

Cys His Gln Thr
            20

<210> SEQ ID NO 219
<211> LENGTH: 20
<212> TYPE: PRT
<213> ORGANISM: artificial sequence
<220> FEATURE:
<223> OTHER INFORMATION: Silica-binding peptide

<400> SEQUENCE: 219

Ser His Leu Met His Val Lys Ala Pro Thr Asp Gln Ala Ser Thr Arg
1               5                   10                  15

Asn Arg Phe Asp
            20

<210> SEQ ID NO 220
<211> LENGTH: 20
<212> TYPE: PRT
<213> ORGANISM: artificial sequence
<220> FEATURE:
<223> OTHER INFORMATION: Silica-binding peptide

<400> SEQUENCE: 220

Ser Ser Ser Thr Pro Pro Asn Ser Pro Lys His Ser Lys Tyr Asn Val
1               5                   10                  15

Trp Thr Ser Pro
            20

<210> SEQ ID NO 221
<211> LENGTH: 17
<212> TYPE: PRT
<213> ORGANISM: artificial sequence
<220> FEATURE:
<223> OTHER INFORMATION: Silica-binding peptide

<400> SEQUENCE: 221

Val His Gln Thr Thr Pro Gln His Lys Asp Ala Val Asn Leu Pro Arg
1               5                   10                  15

Lys

<210> SEQ ID NO 222
<211> LENGTH: 20
<212> TYPE: PRT
<213> ORGANISM: artificial sequence
<220> FEATURE:
<223> OTHER INFORMATION: Silica-binding peptide
```

<400> SEQUENCE: 222

Trp His Ser Ser Glu Gly Gln Tyr Lys Lys Pro Asn Asn His Arg Gln
1               5                   10                  15

Tyr His Thr Gly
            20

<210> SEQ ID NO 223
<211> LENGTH: 15
<212> TYPE: PRT
<213> ORGANISM: artificial sequence
<220> FEATURE:
<223> OTHER INFORMATION: Silica-binding peptide

<400> SEQUENCE: 223

Tyr Lys His Glu Arg His Tyr Ser Gln Pro Leu Lys Val Arg His
1               5                   10                  15

<210> SEQ ID NO 224
<211> LENGTH: 17
<212> TYPE: PRT
<213> ORGANISM: Artificial Sequence
<220> FEATURE:
<223> OTHER INFORMATION: synthetic construct

<400> SEQUENCE: 224

Pro Lys Gly Leu Lys Lys Leu Leu Lys Gly Leu Lys Lys Leu Leu Lys
1               5                   10                  15

Leu

<210> SEQ ID NO 225
<211> LENGTH: 16
<212> TYPE: PRT
<213> ORGANISM: Artificial Sequence
<220> FEATURE:
<223> OTHER INFORMATION: synthetic construct

<400> SEQUENCE: 225

Lys Gly Leu Lys Lys Leu Leu Lys Gly Leu Lys Lys Leu Leu Lys Leu
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: synthetic construct

<400> SEQUENCE: 226

Lys Gly Leu Lys Lys Leu Leu Lys Leu Leu Lys Lys Leu Leu Lys Leu
1               5                   10                  15

<210> SEQ ID NO 227
<211> LENGTH: 14
<212> TYPE: PRT
<213> ORGANISM: Artificial Sequence
<220> FEATURE:
<223> OTHER INFORMATION: synthetic construct

<400> SEQUENCE: 227

Leu Lys Lys Leu Leu Lys Leu Leu Lys Lys Leu Leu Lys Leu
1               5                   10

<210> SEQ ID NO 228
<211> LENGTH: 12
<212> TYPE: PRT

<213> ORGANISM: Artificial Sequence
<220> FEATURE:
<223> OTHER INFORMATION: synthetic construct

<400> SEQUENCE: 228

Leu Lys Lys Leu Leu Lys Leu Leu Lys Lys Leu Leu
1               5                   10

<210> SEQ ID NO 229
<211> LENGTH: 17
<212> TYPE: PRT
<213> ORGANISM: Artificial Sequence
<220> FEATURE:
<223> OTHER INFORMATION: synthetic construct

<400> SEQUENCE: 229

Val Ala Lys Lys Leu Ala Lys Leu Ala Lys Lys Leu Ala Lys Leu Ala
1               5                   10                  15
Leu

<210> SEQ ID NO 230
<211> LENGTH: 13
<212> TYPE: PRT
<213> ORGANISM: Artificial Sequence
<220> FEATURE:
<223> OTHER INFORMATION: synthetic construct

<400> SEQUENCE: 230

Phe Ala Lys Leu Leu Ala Lys Ala Leu Lys Lys Leu Leu
1               5                   10

<210> SEQ ID NO 231
<211> LENGTH: 16
<212> TYPE: PRT
<213> ORGANISM: Artificial Sequence
<220> FEATURE:
<223> OTHER INFORMATION: synthetic construct

<400> SEQUENCE: 231

Lys Gly Leu Lys Lys Gly Leu Lys Leu Leu Lys Leu Leu Lys Leu
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: synthetic construct

<400> SEQUENCE: 232

Lys Gly Leu Lys Lys Leu Leu Lys Leu Gly Lys Lys Leu Leu Lys Leu
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: synthetic construct

<400> SEQUENCE: 233

Lys Gly Leu Lys Lys Leu Gly Lys Leu Leu Lys Lys Leu Leu Lys Leu
1               5                   10                  15

<210> SEQ ID NO 234
<211> LENGTH: 16
<212> TYPE: PRT

```
<213> ORGANISM: Artificial Sequence
<220> FEATURE:
<223> OTHER INFORMATION: synthetic construct

<400> SEQUENCE: 234

Lys Gly Leu Lys Lys Leu Leu Lys Leu Leu Lys Gly Leu Lys Leu
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: synthetic construct

<400> SEQUENCE: 235

Lys Gly Leu Lys Lys Leu Leu Lys Leu Leu Lys Lys Leu Gly Lys Leu
1               5                   10                  15

<210> SEQ ID NO 236
<211> LENGTH: 19
<212> TYPE: PRT
<213> ORGANISM: Artificial Sequence
<220> FEATURE:
<223> OTHER INFORMATION: synthetic construct

<400> SEQUENCE: 236

Phe Ala Leu Ala Leu Lys Ala Leu Lys Lys Leu Lys Lys Ala Leu Lys
1               5                   10                  15

Lys Ala Leu

<210> SEQ ID NO 237
<211> LENGTH: 17
<212> TYPE: PRT
<213> ORGANISM: Artificial Sequence
<220> FEATURE:
<223> OTHER INFORMATION: synthetic construct

<400> SEQUENCE: 237

Phe Ala Lys Lys Leu Ala Lys Leu Ala Lys Lys Leu Ala Lys Leu Ala
1               5                   10                  15

Leu

<210> SEQ ID NO 238
<211> LENGTH: 13
<212> TYPE: PRT
<213> ORGANISM: Artificial Sequence
<220> FEATURE:
<223> OTHER INFORMATION: synthetic construct

<400> SEQUENCE: 238

Phe Ala Lys Leu Leu Ala Lys Leu Ala Lys Lys Leu Leu
1               5                   10

<210> SEQ ID NO 239
<211> LENGTH: 15
<212> TYPE: PRT
<213> ORGANISM: Artificial Sequence
<220> FEATURE:
<223> OTHER INFORMATION: synthetic construct

<400> SEQUENCE: 239

Phe Ala Lys Lys Leu Ala Lys Leu Ala Leu Lys Leu Ala Lys Leu
1               5                   10                  15

<210> SEQ ID NO 240
```

<211> LENGTH: 10
<212> TYPE: PRT
<213> ORGANISM: Artificial Sequence
<220> FEATURE:
<223> OTHER INFORMATION: synthetic construct

<400> SEQUENCE: 240

Phe Ala Lys Lys Leu Ala Lys Lys Leu Leu
1               5                   10

<210> SEQ ID NO 241
<211> LENGTH: 13
<212> TYPE: PRT
<213> ORGANISM: Artificial Sequence
<220> FEATURE:
<223> OTHER INFORMATION: synthetic construct

<400> SEQUENCE: 241

Phe Ala Lys Leu Leu Ala Lys Leu Ala Lys Lys Val Leu
1               5                   10

<210> SEQ ID NO 242
<211> LENGTH: 13
<212> TYPE: PRT
<213> ORGANISM: Artificial Sequence
<220> FEATURE:
<223> OTHER INFORMATION: synthetic construct

<400> SEQUENCE: 242

Lys Tyr Lys Lys Ala Leu Lys Lys Leu Ala Lys Leu Leu
1               5                   10

<210> SEQ ID NO 243
<211> LENGTH: 12
<212> TYPE: PRT
<213> ORGANISM: Artificial Sequence
<220> FEATURE:
<223> OTHER INFORMATION: synthetic construct

<400> SEQUENCE: 243

Phe Ala Leu Leu Lys Ala Leu Leu Lys Lys Ala Leu
1               5                   10

<210> SEQ ID NO 244
<211> LENGTH: 14
<212> TYPE: PRT
<213> ORGANISM: Artificial Sequence
<220> FEATURE:
<223> OTHER INFORMATION: synthetic construct

<400> SEQUENCE: 244

Lys Arg Leu Phe Lys Lys Leu Lys Phe Ser Leu Arg Lys Tyr
1               5                   10

<210> SEQ ID NO 245
<211> LENGTH: 14
<212> TYPE: PRT
<213> ORGANISM: Artificial Sequence
<220> FEATURE:
<223> OTHER INFORMATION: synthetic construct

<400> SEQUENCE: 245

Lys Arg Leu Phe Lys Lys Leu Leu Phe Ser Leu Arg Lys Tyr
1               5                   10

<210> SEQ ID NO 246
<211> LENGTH: 14
<212> TYPE: PRT

```
<213> ORGANISM: Artificial Sequence
<220> FEATURE:
<223> OTHER INFORMATION: synthetic construct

<400> SEQUENCE: 246

Leu Leu Leu Phe Leu Leu Lys Lys Arg Lys Lys Arg Lys Tyr
1               5                   10

<210> SEQ ID NO 247
<211> LENGTH: 36
<212> TYPE: PRT
<213> ORGANISM: Hyalophora cecropia

<400> SEQUENCE: 247

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
            20                  25                  30

Gln Ile Ala Lys
        35

<210> SEQ ID NO 248
<211> LENGTH: 23
<212> TYPE: PRT
<213> ORGANISM: Xenopus laevis

<400> SEQUENCE: 248

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 249
<211> LENGTH: 22
<212> TYPE: PRT
<213> ORGANISM: Xenopus laevis

<400> SEQUENCE: 249

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 250
<211> LENGTH: 12
<212> TYPE: PRT
<213> ORGANISM: Bos taurus

<400> SEQUENCE: 250

Arg Leu Cys Arg Ile Val Val Ile Arg Val Cys Arg
1               5                   10

<210> SEQ ID NO 251
<211> LENGTH: 13
<212> TYPE: PRT
<213> ORGANISM: Bos taurus

<400> SEQUENCE: 251

Ile Leu Pro Trp Lys Trp Pro Trp Trp Pro Trp Arg Arg
1               5                   10

<210> SEQ ID NO 252
<211> LENGTH: 24
<212> TYPE: PRT
```

<213> ORGANISM: Homo sapiens

<400> SEQUENCE: 252

Asp Ser His Ala Lys Arg His His Gly Tyr Lys Arg Lys Phe His Glu
1               5                   10                  15

Lys His His Ser His Arg Gly Tyr
            20

<210> SEQ ID NO 253
<211> LENGTH: 33
<212> TYPE: PRT
<213> ORGANISM: artificial sequence
<220> FEATURE:
<223> OTHER INFORMATION: synthetic linker

<400> SEQUENCE: 253

Glu Pro Glu Pro Glu Pro Glu Pro Ile Pro Glu Pro Pro Lys Glu Ala
1               5                   10                  15

Pro Val Val Ile Glu Lys Pro Lys Pro Lys Pro Lys Pro Lys Pro Lys
            20                  25                  30

Pro

<210> SEQ ID NO 254
<211> LENGTH: 21
<212> TYPE: PRT
<213> ORGANISM: artificial sequence
<220> FEATURE:
<223> OTHER INFORMATION: synthetic peptide linker

<400> SEQUENCE: 254

Gly Lys Gly Lys Gly Lys Gly Lys Gly Lys Gly Lys Gly Lys Gly Lys
1               5                   10                  15

Gly Lys Gly Lys Gly
            20

<210> SEQ ID NO 255
<211> LENGTH: 8
<212> TYPE: PRT
<213> ORGANISM: artificial sequence
<220> FEATURE:
<223> OTHER INFORMATION: synthetic peptide bridge

<400> SEQUENCE: 255

Gly Ser Gly Gly Gly Gly Ser Pro
1               5

<210> SEQ ID NO 256
<211> LENGTH: 16
<212> TYPE: PRT
<213> ORGANISM: artificial sequence
<220> FEATURE:
<223> OTHER INFORMATION: synthetic peptide bridge

<400> SEQUENCE: 256

Gly Ser Gly Gly Gly Gly Ser Pro Gly Ser Gly Gly Gly Gly Ser Pro
1               5                   10                  15

<210> SEQ ID NO 257
<211> LENGTH: 28
<212> TYPE: PRT
<213> ORGANISM: Artificial sequence
<220> FEATURE:
<223> OTHER INFORMATION: PMMA-binding peptide
<220> FEATURE:
<221> NAME/KEY: MISC_FEATURE
<222> LOCATION: (28)..(28)

<223> OTHER INFORMATION: Lysine added to C-terminus for biotin
      attachment

<400> SEQUENCE: 257

Gly Trp Gln Arg Ile Trp Gln Ser Ile Leu Cys Trp Met Tyr Phe Pro
1               5                   10                  15

Leu Cys Leu Trp Met Glu Trp Tyr Arg Ala Ile Lys
            20                  25

<210> SEQ ID NO 258
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 258

Arg Val Pro Asn Lys Thr Val Thr Val Asp Gly Ala
1               5                   10

<210> SEQ ID NO 259
<211> LENGTH: 12
<212> TYPE: PRT
<213> ORGANISM: artificial sequence
<220> FEATURE:
<223> OTHER INFORMATION: Synthetic construct

<400> SEQUENCE: 259

Asp Arg His Lys Ser Lys Tyr Ser Ser Thr Lys Ser
1               5                   10

<210> SEQ ID NO 260
<211> LENGTH: 12
<212> TYPE: PRT
<213> ORGANISM: artificial sequence
<220> FEATURE:
<223> OTHER INFORMATION: Synthetic construct

<400> SEQUENCE: 260

Lys Asn Phe Pro Gln Gln Lys Glu Phe Pro Leu Ser
1               5                   10

<210> SEQ ID NO 261
<211> LENGTH: 12
<212> TYPE: PRT
<213> ORGANISM: artificial sequence
<220> FEATURE:
<223> OTHER INFORMATION: Synthetic construct

<400> SEQUENCE: 261

Gln Arg Asn Ser Pro Pro Ala Met Ser Arg Arg Asp
1               5                   10

<210> SEQ ID NO 262
<211> LENGTH: 12
<212> TYPE: PRT
<213> ORGANISM: artificial sequence
<220> FEATURE:
<223> OTHER INFORMATION: Synthetic construct

<400> SEQUENCE: 262

Thr Arg Lys Pro Asn Met Pro His Gly Gln Tyr Leu
1               5                   10

<210> SEQ ID NO 263
<211> LENGTH: 12
<212> TYPE: PRT

```
<213> ORGANISM: artificial sequence
<220> FEATURE:
<223> OTHER INFORMATION: Synthetic construct

<400> SEQUENCE: 263

Lys Pro Pro His Leu Ala Lys Leu Pro Phe Thr Thr
1               5                   10

<210> SEQ ID NO 264
<211> LENGTH: 12
<212> TYPE: PRT
<213> ORGANISM: artificial sequence
<220> FEATURE:
<223> OTHER INFORMATION: Synthetic construct

<400> SEQUENCE: 264

Asn Lys Arg Pro Pro Thr Ser His Arg Ile His Ala
1               5                   10

<210> SEQ ID NO 265
<211> LENGTH: 12
<212> TYPE: PRT
<213> ORGANISM: artificial sequence
<220> FEATURE:
<223> OTHER INFORMATION: Synthetic construct

<400> SEQUENCE: 265

Asn Leu Pro Arg Tyr Gln Pro Pro Cys Lys Pro Leu
1               5                   10

<210> SEQ ID NO 266
<211> LENGTH: 12
<212> TYPE: PRT
<213> ORGANISM: artificial sequence
<220> FEATURE:
<223> OTHER INFORMATION: Synthetic construct

<400> SEQUENCE: 266

Arg Pro Pro Trp Lys Lys Pro Ile Pro Pro Ser Glu
1               5                   10

<210> SEQ ID NO 267
<211> LENGTH: 12
<212> TYPE: PRT
<213> ORGANISM: artificial sequence
<220> FEATURE:
<223> OTHER INFORMATION: Synthetic construct

<400> SEQUENCE: 267

Arg Gln Arg Pro Lys Asp His Phe Phe Ser Arg Pro
1               5                   10

<210> SEQ ID NO 268
<211> LENGTH: 12
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa = Thr or Pro
<220> FEATURE:
<221> NAME/KEY: MISC_FEATURE
<222> LOCATION: (12)..(12)
<223> OTHER INFORMATION: Xaa = Thr or Pro

<400> SEQUENCE: 268

Ser Val Pro Asn Lys Xaa Val Thr Val Asp Gly Xaa
```

```
1               5                  10
```

<210> SEQ ID NO 269
<211> LENGTH: 12
<212> TYPE: PRT
<213> ORGANISM: artificial sequence
<220> FEATURE:
<223> OTHER INFORMATION: Synthetic construct

<400> SEQUENCE: 269

```
Thr Thr Lys Trp Arg His Arg Ala Pro Val Ser Pro
1               5                  10
```

<210> SEQ ID NO 270
<211> LENGTH: 12
<212> TYPE: PRT
<213> ORGANISM: artificial sequence
<220> FEATURE:
<223> OTHER INFORMATION: Synthetic construct

<400> SEQUENCE: 270

```
Trp Leu Gly Lys Asn Arg Ile Lys Pro Arg Ala Ser
1               5                  10
```

<210> SEQ ID NO 271
<211> LENGTH: 12
<212> TYPE: PRT
<213> ORGANISM: artificial sequence
<220> FEATURE:
<223> OTHER INFORMATION: Synthetic construct

<400> SEQUENCE: 271

```
Ser Asn Phe Lys Thr Pro Leu Pro Leu Thr Gln Ser
1               5                  10
```

<210> SEQ ID NO 272
<211> LENGTH: 12
<212> TYPE: PRT
<213> ORGANISM: artificial sequence
<220> FEATURE:
<223> OTHER INFORMATION: Synthetic construct

<400> SEQUENCE: 272

```
Ser Val Ser Val Gly Met Lys Pro Ser Pro Arg Pro
1               5                  10
```

<210> SEQ ID NO 273
<211> LENGTH: 7
<212> TYPE: PRT
<213> ORGANISM: artificial sequence
<220> FEATURE:
<223> OTHER INFORMATION: Synthetic construct

<400> SEQUENCE: 273

```
Asp Leu His Thr Val Tyr His
1               5
```

<210> SEQ ID NO 274
<211> LENGTH: 7
<212> TYPE: PRT
<213> ORGANISM: artificial sequence
<220> FEATURE:
<223> OTHER INFORMATION: Synthetic construct

<400> SEQUENCE: 274

```
His Ile Lys Pro Pro Thr Arg
1               5
```

<210> SEQ ID NO 275
<211> LENGTH: 7
<212> TYPE: PRT
<213> ORGANISM: artificial sequence
<220> FEATURE:
<223> OTHER INFORMATION: Synthetic construct

<400> SEQUENCE: 275

His Pro Val Trp Pro Ala Ile
1               5

<210> SEQ ID NO 276
<211> LENGTH: 7
<212> TYPE: PRT
<213> ORGANISM: artificial sequence
<220> FEATURE:
<223> OTHER INFORMATION: Synthetic construct

<400> SEQUENCE: 276

Met Pro Leu Tyr Tyr Leu Gln
1               5

<210> SEQ ID NO 277
<211> LENGTH: 26
<212> TYPE: PRT
<213> ORGANISM: artificial sequence
<220> FEATURE:
<223> OTHER INFORMATION: Synthetic construct

<400> SEQUENCE: 277

His Leu Thr Val Pro Trp Arg Gly Gly Gly Ser Ala Val Pro Phe Tyr
1               5                   10                  15

Ser His Ser Gln Ile Thr Leu Pro Asn His
            20                  25

<210> SEQ ID NO 278
<211> LENGTH: 41
<212> TYPE: PRT
<213> ORGANISM: artificial sequence
<220> FEATURE:
<223> OTHER INFORMATION: Synthetic construct

<400> SEQUENCE: 278

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
        35                  40

<210> SEQ ID NO 279
<211> LENGTH: 7
<212> TYPE: PRT
<213> ORGANISM: artificial sequence
<220> FEATURE:
<223> OTHER INFORMATION: Synthetic construct

<400> SEQUENCE: 279

Lys His Pro Thr Tyr Arg Gln
1               5

<210> SEQ ID NO 280
<211> LENGTH: 7
<212> TYPE: PRT
<213> ORGANISM: artificial sequence
<220> FEATURE:

<223> OTHER INFORMATION: Synthetic construct

<400> SEQUENCE: 280

His Pro Met Ser Ala Pro Arg
1               5

<210> SEQ ID NO 281
<211> LENGTH: 7
<212> TYPE: PRT
<213> ORGANISM: artificial sequence
<220> FEATURE:
<223> OTHER INFORMATION: Synthetic construct

<400> SEQUENCE: 281

Met Pro Lys Tyr Tyr Leu Gln
1               5

<210> SEQ ID NO 282
<211> LENGTH: 7
<212> TYPE: PRT
<213> ORGANISM: artificial sequence
<220> FEATURE:
<223> OTHER INFORMATION: Synthetic construct

<400> SEQUENCE: 282

Met His Ala His Ser Ile Ala
1               5

<210> SEQ ID NO 283
<211> LENGTH: 12
<212> TYPE: PRT
<213> ORGANISM: artificial sequence
<220> FEATURE:
<223> OTHER INFORMATION: Synthetic construct

<400> SEQUENCE: 283

Ala Lys Pro Ile Ser Gln His Leu Gln Arg Gly Ser
1               5                   10

<210> SEQ ID NO 284
<211> LENGTH: 12
<212> TYPE: PRT
<213> ORGANISM: artificial sequence
<220> FEATURE:
<223> OTHER INFORMATION: Synthetic construct

<400> SEQUENCE: 284

Ala Pro Pro Thr Pro Ala Ala Ala Ser Ala Thr Thr
1               5                   10

<210> SEQ ID NO 285
<211> LENGTH: 12
<212> TYPE: PRT
<213> ORGANISM: artificial sequence
<220> FEATURE:
<223> OTHER INFORMATION: Synthetic construct

<400> SEQUENCE: 285

Asp Pro Thr Glu Gly Ala Arg Arg Thr Ile Met Thr
1               5                   10

<210> SEQ ID NO 286
<211> LENGTH: 12
<212> TYPE: PRT
<213> ORGANISM: artificial sequence
<220> FEATURE:
<223> OTHER INFORMATION: Synthetic construct

```
<400> SEQUENCE: 286

Leu Asp Thr Ser Phe Pro Pro Val Pro Phe His Ala
1               5                   10

<210> SEQ ID NO 287
<211> LENGTH: 12
<212> TYPE: PRT
<213> ORGANISM: artificial sequence
<220> FEATURE:
<223> OTHER INFORMATION: Synthetic construct

<400> SEQUENCE: 287

Leu Asp Thr Ser Phe His Gln Val Pro Phe His Gln
1               5                   10

<210> SEQ ID NO 288
<211> LENGTH: 11
<212> TYPE: PRT
<213> ORGANISM: artificial sequence
<220> FEATURE:
<223> OTHER INFORMATION: Synthetic construct

<400> SEQUENCE: 288

Leu Pro Arg Ile Ala Asn Thr Trp Ser Pro Ser
1               5                   10

<210> SEQ ID NO 289
<211> LENGTH: 12
<212> TYPE: PRT
<213> ORGANISM: artificial sequence
<220> FEATURE:
<223> OTHER INFORMATION: Synthetic construct

<400> SEQUENCE: 289

Arg Thr Asn Ala Ala Asp His Pro Ala Ala Val Thr
1               5                   10

<210> SEQ ID NO 290
<211> LENGTH: 12
<212> TYPE: PRT
<213> ORGANISM: artificial sequence
<220> FEATURE:
<223> OTHER INFORMATION: Synthetic construct

<400> SEQUENCE: 290

Ser Leu Asn Trp Val Thr Ile Pro Gly Pro Lys Ile
1               5                   10

<210> SEQ ID NO 291
<211> LENGTH: 12
<212> TYPE: PRT
<213> ORGANISM: artificial sequence
<220> FEATURE:
<223> OTHER INFORMATION: Synthetic construct

<400> SEQUENCE: 291

Thr Asp Met Gln Ala Pro Thr Lys Ser Tyr Ser Asn
1               5                   10

<210> SEQ ID NO 292
<211> LENGTH: 12
<212> TYPE: PRT
<213> ORGANISM: artificial sequence
<220> FEATURE:
<223> OTHER INFORMATION: Synthetic construct

<400> SEQUENCE: 292
```

Thr Ile Met Thr Lys Ser Pro Ser Leu Ser Cys Gly
1               5                   10

<210> SEQ ID NO 293
<211> LENGTH: 12
<212> TYPE: PRT
<213> ORGANISM: artificial sequence
<220> FEATURE:
<223> OTHER INFORMATION: Synthetic construct

<400> SEQUENCE: 293

Thr Pro Ala Leu Asp Gly Leu Arg Gln Pro Leu Arg
1               5                   10

<210> SEQ ID NO 294
<211> LENGTH: 12
<212> TYPE: PRT
<213> ORGANISM: artificial sequence
<220> FEATURE:
<223> OTHER INFORMATION: Synthetic construct

<400> SEQUENCE: 294

Thr Tyr Pro Ala Ser Arg Leu Pro Leu Leu Ala Pro
1               5                   10

<210> SEQ ID NO 295
<211> LENGTH: 12
<212> TYPE: PRT
<213> ORGANISM: artificial sequence
<220> FEATURE:
<223> OTHER INFORMATION: Synthetic construct

<400> SEQUENCE: 295

Ala Lys Thr His Lys His Pro Ala Pro Ser Tyr Ser
1               5                   10

<210> SEQ ID NO 296
<211> LENGTH: 12
<212> TYPE: PRT
<213> ORGANISM: artificial sequence
<220> FEATURE:
<223> OTHER INFORMATION: Synthetic construct

<400> SEQUENCE: 296

Thr Asp Pro Thr Pro Phe Ser Ile Ser Pro Glu Arg
1               5                   10

<210> SEQ ID NO 297
<211> LENGTH: 12
<212> TYPE: PRT
<213> ORGANISM: artificial sequence
<220> FEATURE:
<223> OTHER INFORMATION: Synthetic construct

<400> SEQUENCE: 297

Ser Gln Asn Trp Gln Asp Ser Thr Ser Tyr Ser Asn
1               5                   10

<210> SEQ ID NO 298
<211> LENGTH: 12
<212> TYPE: PRT
<213> ORGANISM: artificial sequence
<220> FEATURE:
<223> OTHER INFORMATION: Synthetic construct

<400> SEQUENCE: 298

Trp His Asp Lys Pro Gln Asn Ser Ser Lys Ser Thr
1               5                   10

```
<210> SEQ ID NO 299
<211> LENGTH: 12
<212> TYPE: PRT
<213> ORGANISM: artificial sequence
<220> FEATURE:
<223> OTHER INFORMATION: Synthetic construct

<400> SEQUENCE: 299

Leu Asp Val Glu Ser Tyr Lys Gly Thr Ser Met Pro
1               5                   10

<210> SEQ ID NO 300
<211> LENGTH: 7
<212> TYPE: PRT
<213> ORGANISM: artificial sequence
<220> FEATURE:
<223> OTHER INFORMATION: Synthetic construct

<400> SEQUENCE: 300

Asn Thr Pro Lys Glu Asn Trp
1               5

<210> SEQ ID NO 301
<211> LENGTH: 7
<212> TYPE: PRT
<213> ORGANISM: artificial sequence
<220> FEATURE:
<223> OTHER INFORMATION: Synthetic construct

<400> SEQUENCE: 301

Asn Thr Pro Ala Ser Asn Arg
1               5

<210> SEQ ID NO 302
<211> LENGTH: 7
<212> TYPE: PRT
<213> ORGANISM: artificial sequence
<220> FEATURE:
<223> OTHER INFORMATION: Synthetic construct

<400> SEQUENCE: 302

Pro Arg Gly Met Leu Ser Thr
1               5

<210> SEQ ID NO 303
<211> LENGTH: 7
<212> TYPE: PRT
<213> ORGANISM: artificial sequence
<220> FEATURE:
<223> OTHER INFORMATION: Synthetic construct

<400> SEQUENCE: 303

Pro Pro Thr Tyr Leu Ser Thr
1               5

<210> SEQ ID NO 304
<211> LENGTH: 12
<212> TYPE: PRT
<213> ORGANISM: artificial sequence
<220> FEATURE:
<223> OTHER INFORMATION: Synthetic construct

<400> SEQUENCE: 304

Thr Ile Pro Thr His Arg Gln His Asp Tyr Arg Ser
1               5                   10
```

```
<210> SEQ ID NO 305
<211> LENGTH: 7
<212> TYPE: PRT
<213> ORGANISM: artificial sequence
<220> FEATURE:
<223> OTHER INFORMATION: Synthetic construct

<400> SEQUENCE: 305

Thr Pro Pro Thr His Arg Leu
1               5

<210> SEQ ID NO 306
<211> LENGTH: 7
<212> TYPE: PRT
<213> ORGANISM: artificial sequence
<220> FEATURE:
<223> OTHER INFORMATION: Synthetic construct

<400> SEQUENCE: 306

Leu Pro Thr Met Ser Thr Pro
1               5

<210> SEQ ID NO 307
<211> LENGTH: 7
<212> TYPE: PRT
<213> ORGANISM: artificial sequence
<220> FEATURE:
<223> OTHER INFORMATION: Synthetic construct

<400> SEQUENCE: 307

Leu Gly Thr Asn Ser Thr Pro
1               5

<210> SEQ ID NO 308
<211> LENGTH: 12
<212> TYPE: PRT
<213> ORGANISM: artificial sequence
<220> FEATURE:
<223> OTHER INFORMATION: Synthetic construct

<400> SEQUENCE: 308

Thr Pro Leu Thr Gly Ser Thr Asn Leu Leu Ser Ser
1               5                   10

<210> SEQ ID NO 309
<211> LENGTH: 7
<212> TYPE: PRT
<213> ORGANISM: artificial sequence
<220> FEATURE:
<223> OTHER INFORMATION: Synthetic construct

<400> SEQUENCE: 309

Thr Pro Leu Thr Lys Glu Thr
1               5

<210> SEQ ID NO 310
<211> LENGTH: 7
<212> TYPE: PRT
<213> ORGANISM: artificial sequence
<220> FEATURE:
<223> OTHER INFORMATION: Synthetic construct

<400> SEQUENCE: 310

Lys Gln Ser His Asn Pro Pro
1               5

<210> SEQ ID NO 311
<211> LENGTH: 7
```

```
<212> TYPE: PRT
<213> ORGANISM: artificial sequence
<220> FEATURE:
<223> OTHER INFORMATION: Synthetic construct

<400> SEQUENCE: 311

Gln Gln Ser His Asn Pro Pro
1               5

<210> SEQ ID NO 312
<211> LENGTH: 7
<212> TYPE: PRT
<213> ORGANISM: artificial sequence
<220> FEATURE:
<223> OTHER INFORMATION: Synthetic construct

<400> SEQUENCE: 312

Thr Gln Pro His Asn Pro Pro
1               5

<210> SEQ ID NO 313
<211> LENGTH: 12
<212> TYPE: PRT
<213> ORGANISM: artificial sequence
<220> FEATURE:
<223> OTHER INFORMATION: Synthetic construct

<400> SEQUENCE: 313

Ser Thr Asn Leu Leu Arg Thr Ser Thr Val His Pro
1               5                   10

<210> SEQ ID NO 314
<211> LENGTH: 12
<212> TYPE: PRT
<213> ORGANISM: artificial sequence
<220> FEATURE:
<223> OTHER INFORMATION: Synthetic construct

<400> SEQUENCE: 314

His Thr Gln Pro Ser Tyr Ser Ser Thr Asn Leu Phe
1               5                   10

<210> SEQ ID NO 315
<211> LENGTH: 7
<212> TYPE: PRT
<213> ORGANISM: artificial sequence
<220> FEATURE:
<223> OTHER INFORMATION: Synthetic construct

<400> SEQUENCE: 315

Ser Leu Leu Ser Ser His Ala
1               5

<210> SEQ ID NO 316
<211> LENGTH: 12
<212> TYPE: PRT
<213> ORGANISM: artificial sequence
<220> FEATURE:
<223> OTHER INFORMATION: Synthetic construct

<400> SEQUENCE: 316

Gln Gln Ser Ser Ile Ser Leu Ser Ser His Ala Val
1               5                   10

<210> SEQ ID NO 317
<211> LENGTH: 7
<212> TYPE: PRT
<213> ORGANISM: artificial sequence
```

```
<220> FEATURE:
<223> OTHER INFORMATION: Synthetic construct

<400> SEQUENCE: 317

Asn Ala Ser Pro Ser Ser Leu
1               5

<210> SEQ ID NO 318
<211> LENGTH: 7
<212> TYPE: PRT
<213> ORGANISM: artificial sequence
<220> FEATURE:
<223> OTHER INFORMATION: Synthetic construct

<400> SEQUENCE: 318

His Ser Pro Ser Ser Leu Arg
1               5

<210> SEQ ID NO 319
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= H, R or N
<220> FEATURE:
<221> NAME/KEY: MISC_FEATURE
<222> LOCATION: (2)..(2)
<223> OTHER INFORMATION: X= His, Arg or Asn

<400> SEQUENCE: 319

Lys Xaa Ser His His Thr His
1               5

<210> SEQ ID NO 320
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X = H, R or N
<220> FEATURE:
<221> NAME/KEY: MISC_FEATURE
<222> LOCATION: (2)..(2)
<223> OTHER INFORMATION: X = His, Arg or Asn

<400> SEQUENCE: 320

Glu Xaa Ser His His Thr His
1               5

<210> SEQ ID NO 321
<211> LENGTH: 12
<212> TYPE: PRT
<213> ORGANISM: artificial sequence
<220> FEATURE:
<223> OTHER INFORMATION: Synthetic construct

<400> SEQUENCE: 321

Ser His His Thr His Tyr Gly Gln Pro Gly Pro Val
1               5                   10

<210> SEQ ID NO 322
<211> LENGTH: 7
<212> TYPE: PRT
```

```
<213> ORGANISM: artificial sequence
<220> FEATURE:
<223> OTHER INFORMATION: Synthetic construct

<400> SEQUENCE: 322

Leu Glu Ser Thr Ser Leu Leu
1               5

<210> SEQ ID NO 323
<211> LENGTH: 7
<212> TYPE: PRT
<213> ORGANISM: artificial sequence
<220> FEATURE:
<223> OTHER INFORMATION: Synthetic construct

<400> SEQUENCE: 323

Asp Leu Thr Leu Pro Phe His
1               5

<210> SEQ ID NO 324
<211> LENGTH: 8
<212> TYPE: PRT
<213> ORGANISM: artificial sequence
<220> FEATURE:
<223> OTHER INFORMATION: Synthetic construct

<400> SEQUENCE: 324

Arg Thr Asn Ala Ala Asp His Pro
1               5

<210> SEQ ID NO 325
<211> LENGTH: 12
<212> TYPE: PRT
<213> ORGANISM: artificial sequence
<220> FEATURE:
<223> OTHER INFORMATION: Synthetic construct

<400> SEQUENCE: 325

Ile Pro Trp Trp Asn Ile Arg Ala Pro Leu Asn Ala
1               5                   10

<210> SEQ ID NO 326
<211> LENGTH: 18
<212> TYPE: PRT
<213> ORGANISM: artificial sequence
<220> FEATURE:
<223> OTHER INFORMATION: Synthetic construct

<400> SEQUENCE: 326

Glu Gln Ile Ser Gly Ser Leu Val Ala Ala Pro Trp Glu Gly Glu Gly
1               5                   10                  15

Glu Arg

<210> SEQ ID NO 327
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 327

Thr Pro Pro Glu Leu Leu His Gly Ala Pro Arg Ser
1               5                   10

<210> SEQ ID NO 328
<211> LENGTH: 18
<212> TYPE: PRT
```

```
<213> ORGANISM: artificial sequence
<220> FEATURE:
<223> OTHER INFORMATION: Synthetic construct

<400> SEQUENCE: 328

Leu Asp Thr Ser Phe His Gln Val Pro Phe His Gln Lys Arg Lys Arg
1               5                   10                  15

Lys Asp

<210> SEQ ID NO 329
<211> LENGTH: 18
<212> TYPE: PRT
<213> ORGANISM: artificial sequence
<220> FEATURE:
<223> OTHER INFORMATION: Synthetic construct

<400> SEQUENCE: 329

Glu Gln Ile Ser Gly Ser Leu Val Ala Ala Pro Trp Lys Arg Lys Arg
1               5                   10                  15

Lys Asp

<210> SEQ ID NO 330
<211> LENGTH: 18
<212> TYPE: PRT
<213> ORGANISM: artificial sequence
<220> FEATURE:
<223> OTHER INFORMATION: Synthetic construct

<400> SEQUENCE: 330

Thr Pro Pro Glu Leu Leu His Gly Asp Pro Arg Ser Lys Arg Lys Arg
1               5                   10                  15

Lys Asp

<210> SEQ ID NO 331
<211> LENGTH: 13
<212> TYPE: PRT
<213> ORGANISM: artificial sequence
<220> FEATURE:
<223> OTHER INFORMATION: Synthetic construct

<400> SEQUENCE: 331

Asn Thr Ser Gln Leu Ser Thr Glu Gly Glu Gly Glu Asp
1               5                   10

<210> SEQ ID NO 332
<211> LENGTH: 13
<212> TYPE: PRT
<213> ORGANISM: artificial sequence
<220> FEATURE:
<223> OTHER INFORMATION: Synthetic construct

<400> SEQUENCE: 332

Thr Pro Pro Glu Leu Leu His Gly Asp Pro Arg Ser Cys
1               5                   10

<210> SEQ ID NO 333
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 333

His Ile Asn Lys Thr Asn Pro His Gln Gly Asn His His Ser Glu Lys
1               5                   10                  15
```

```
Thr Gln Arg Gln
            20

<210> SEQ ID NO 334
<211> LENGTH: 15
<212> TYPE: PRT
<213> ORGANISM: artificial sequence
<220> FEATURE:
<223> OTHER INFORMATION: Synthetic construct

<400> SEQUENCE: 334

His Ala His Lys Asn Gln Lys Glu Thr His Gln Arg His Ala Ala
1               5                   10                  15

<210> SEQ ID NO 335
<211> LENGTH: 15
<212> TYPE: PRT
<213> ORGANISM: artificial sequence
<220> FEATURE:
<223> OTHER INFORMATION: Synthetic construct

<400> SEQUENCE: 335

His Glu His Lys Asn Gln Lys Glu Thr His Gln Arg His Ala Ala
1               5                   10                  15

<210> SEQ ID NO 336
<211> LENGTH: 20
<212> TYPE: PRT
<213> ORGANISM: artificial sequence
<220> FEATURE:
<223> OTHER INFORMATION: Synthetic construct

<400> SEQUENCE: 336

His Asn His Met Gln Glu Arg Tyr Thr Glu Pro Gln His Ser Pro Ser
1               5                   10                  15

Val Asn Gly Leu
            20

<210> SEQ ID NO 337
<211> LENGTH: 17
<212> TYPE: PRT
<213> ORGANISM: artificial sequence
<220> FEATURE:
<223> OTHER INFORMATION: Synthetic construct

<400> SEQUENCE: 337

Thr His Ser Thr His Asn His Gly Ser Pro Arg His Thr Asn Ala Asp
1               5                   10                  15

Ala

<210> SEQ ID NO 338
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 338

Gly Ser Cys Val Asp Thr His Lys Ala Asp Ser Cys Val Ala Asn Asn
1               5                   10                  15

Gly Pro Ala Thr
            20

<210> SEQ ID NO 339
<211> LENGTH: 20
<212> TYPE: PRT
```

```
<213> ORGANISM: artificial sequence
<220> FEATURE:
<223> OTHER INFORMATION: synthetic hair-binding peptide

<400> SEQUENCE: 339

Ala Gln Ser Gln Leu Pro Asp Lys His Ser Gly Leu His Glu Arg Ala
1               5                   10                  15

Pro Gln Arg Tyr
            20

<210> SEQ ID NO 340
<211> LENGTH: 20
<212> TYPE: PRT
<213> ORGANISM: artificial sequence
<220> FEATURE:
<223> OTHER INFORMATION: Synthetic construct

<400> SEQUENCE: 340

Ala Gln Ser Gln Leu Pro Ala Lys His Ser Gly Leu His Glu Arg Ala
1               5                   10                  15

Pro Gln Arg Tyr
            20

<210> SEQ ID NO 341
<211> LENGTH: 20
<212> TYPE: PRT
<213> ORGANISM: artificial sequence
<220> FEATURE:
<223> OTHER INFORMATION: Synthetic construct

<400> SEQUENCE: 341

Ala Gln Ser Gln Leu Pro Glu Lys His Ser Gly Leu His Glu Arg Ala
1               5                   10                  15

Pro Gln Arg Tyr
            20

<210> SEQ ID NO 342
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 342

Thr Asp Met Met His Asn His Ser Asp Asn Ser Pro Pro His Arg Arg
1               5                   10                  15

Ser Pro Arg Asn
            20

<210> SEQ ID NO 343
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 343

Thr Pro Pro Glu Leu Ala His Thr Pro His His Leu Ala Gln Thr Arg
1               5                   10                  15

Leu Thr Asp Arg
            20

<210> SEQ ID NO 344
<211> LENGTH: 12
<212> TYPE: PRT
```

```
<213> ORGANISM: artificial sequence
<220> FEATURE:
<223> OTHER INFORMATION: Synthetic construct

<400> SEQUENCE: 344

Arg Leu Leu Arg Leu Leu Arg Leu Leu Arg Leu Leu
1               5                   10

<210> SEQ ID NO 345
<211> LENGTH: 12
<212> TYPE: PRT
<213> ORGANISM: artificial sequence
<220> FEATURE:
<223> OTHER INFORMATION: Synthetic construct

<400> SEQUENCE: 345

Thr Pro Pro Glu Leu Leu His Gly Glu Pro Arg Ser
1               5                   10

<210> SEQ ID NO 346
<211> LENGTH: 12
<212> TYPE: PRT
<213> ORGANISM: artificial sequence
<220> FEATURE:
<223> OTHER INFORMATION: Synthetic construct

<400> SEQUENCE: 346

Thr Pro Pro Glu Leu Leu His Gly Ala Pro Arg Ser
1               5                   10

<210> SEQ ID NO 347
<211> LENGTH: 12
<212> TYPE: PRT
<213> ORGANISM: artificial sequence
<220> FEATURE:
<223> OTHER INFORMATION: Synthetic construct

<400> SEQUENCE: 347

Glu Gln Ile Ser Gly Ser Leu Val Ala Ala Pro Trp
1               5                   10

<210> SEQ ID NO 348
<211> LENGTH: 12
<212> TYPE: PRT
<213> ORGANISM: artificial sequence
<220> FEATURE:
<223> OTHER INFORMATION: Synthetic construct

<400> SEQUENCE: 348

Asn Glu Val Pro Ala Arg Asn Ala Pro Trp Leu Val
1               5                   10

<210> SEQ ID NO 349
<211> LENGTH: 13
<212> TYPE: PRT
<213> ORGANISM: artificial sequence
<220> FEATURE:
<223> OTHER INFORMATION: Synthetic construct

<400> SEQUENCE: 349

Asn Ser Pro Gly Tyr Gln Ala Asp Ser Val Ala Ile Gly
1               5                   10

<210> SEQ ID NO 350
<211> LENGTH: 12
<212> TYPE: PRT
<213> ORGANISM: artificial sequence
<220> FEATURE:
```

<223> OTHER INFORMATION: Synthetic construct

<400> SEQUENCE: 350

Ala Lys Pro Ile Ser Gln His Leu Gln Arg Gly Ser
1               5                   10

<210> SEQ ID NO 351
<211> LENGTH: 12
<212> TYPE: PRT
<213> ORGANISM: artificial sequence
<220> FEATURE:
<223> OTHER INFORMATION: Synthetic construct

<400> SEQUENCE: 351

Leu Asp Thr Ser Phe Pro Pro Val Pro Phe His Ala
1               5                   10

<210> SEQ ID NO 352
<211> LENGTH: 12
<212> TYPE: PRT
<213> ORGANISM: artificial sequence
<220> FEATURE:
<223> OTHER INFORMATION: Synthetic construct

<400> SEQUENCE: 352

Ser Leu Asn Trp Val Thr Ile Pro Gly Pro Lys Ile
1               5                   10

<210> SEQ ID NO 353
<211> LENGTH: 12
<212> TYPE: PRT
<213> ORGANISM: artificial sequence
<220> FEATURE:
<223> OTHER INFORMATION: Synthetic construct

<400> SEQUENCE: 353

Thr Gln Asp Ser Ala Gln Lys Ser Pro Ser Pro Leu
1               5                   10

<210> SEQ ID NO 354
<211> LENGTH: 12
<212> TYPE: PRT
<213> ORGANISM: artificial sequence
<220> FEATURE:
<223> OTHER INFORMATION: Synthetic construct

<400> SEQUENCE: 354

Lys Glu Leu Gln Thr Arg Asn Val Val Gln Arg Glu
1               5                   10

<210> SEQ ID NO 355
<211> LENGTH: 12
<212> TYPE: PRT
<213> ORGANISM: artificial sequence
<220> FEATURE:
<223> OTHER INFORMATION: Synthetic construct

<400> SEQUENCE: 355

Gln Arg Asn Ser Pro Pro Ala Met Ser Arg Arg Asp
1               5                   10

<210> SEQ ID NO 356
<211> LENGTH: 12
<212> TYPE: PRT
<213> ORGANISM: artificial sequence
<220> FEATURE:
<223> OTHER INFORMATION: Synthetic construct

```
<400> SEQUENCE: 356

Thr Pro Thr Ala Asn Gln Phe Thr Gln Ser Val Pro
1               5                   10

<210> SEQ ID NO 357
<211> LENGTH: 12
<212> TYPE: PRT
<213> ORGANISM: artificial sequence
<220> FEATURE:
<223> OTHER INFORMATION: Synthetic construct

<400> SEQUENCE: 357

Ala Ala Gly Leu Ser Gln Lys His Glu Arg Asn Arg
1               5                   10

<210> SEQ ID NO 358
<211> LENGTH: 12
<212> TYPE: PRT
<213> ORGANISM: artificial sequence
<220> FEATURE:
<223> OTHER INFORMATION: Synthetic construct

<400> SEQUENCE: 358

Glu Thr Val His Gln Thr Pro Leu Ser Asp Arg Pro
1               5                   10

<210> SEQ ID NO 359
<211> LENGTH: 12
<212> TYPE: PRT
<213> ORGANISM: artificial sequence
<220> FEATURE:
<223> OTHER INFORMATION: Synthetic construct

<400> SEQUENCE: 359

Lys Asn Phe Pro Gln Gln Lys Glu Phe Pro Leu Ser
1               5                   10

<210> SEQ ID NO 360
<211> LENGTH: 12
<212> TYPE: PRT
<213> ORGANISM: artificial sequence
<220> FEATURE:
<223> OTHER INFORMATION: Synthetic construct

<400> SEQUENCE: 360

Leu Pro Ala Leu His Ile Gln Arg His Pro Arg Met
1               5                   10

<210> SEQ ID NO 361
<211> LENGTH: 12
<212> TYPE: PRT
<213> ORGANISM: artificial sequence
<220> FEATURE:
<223> OTHER INFORMATION: Synthetic construct

<400> SEQUENCE: 361

Gln Pro Ser His Ser Gln Ser His Asn Leu Arg Ser
1               5                   10

<210> SEQ ID NO 362
<211> LENGTH: 12
<212> TYPE: PRT
<213> ORGANISM: artificial sequence
<220> FEATURE:
<223> OTHER INFORMATION: Synthetic construct

<400> SEQUENCE: 362
```

Arg Gly Ser Gln Lys Ser Lys Pro Pro Arg Pro Pro
1               5                   10

<210> SEQ ID NO 363
<211> LENGTH: 12
<212> TYPE: PRT
<213> ORGANISM: artificial sequence
<220> FEATURE:
<223> OTHER INFORMATION: Synthetic construct

<400> SEQUENCE: 363

Thr His Thr Gln Lys Thr Pro Leu Leu Tyr Tyr His
1               5                   10

<210> SEQ ID NO 364
<211> LENGTH: 12
<212> TYPE: PRT
<213> ORGANISM: artificial sequence
<220> FEATURE:
<223> OTHER INFORMATION: Synthetic construct

<400> SEQUENCE: 364

Thr Lys Gly Ser Ser Gln Ala Ile Leu Lys Ser Thr
1               5                   10

<210> SEQ ID NO 365
<211> LENGTH: 7
<212> TYPE: PRT
<213> ORGANISM: artificial sequence
<220> FEATURE:
<223> OTHER INFORMATION: Synthetic construct

<400> SEQUENCE: 365

Thr Ala Ala Thr Thr Ser Pro
1               5

<210> SEQ ID NO 366
<211> LENGTH: 7
<212> TYPE: PRT
<213> ORGANISM: artificial sequence
<220> FEATURE:
<223> OTHER INFORMATION: Synthetic construct

<400> SEQUENCE: 366

Leu Gly Ile Pro Gln Asn Leu
1               5

<210> SEQ ID NO 367
<211> LENGTH: 20
<212> TYPE: PRT
<213> ORGANISM: artificial sequence
<220> FEATURE:
<223> OTHER INFORMATION: Synthetic construct

<400> SEQUENCE: 367

Thr His Ser Thr His Asn His Gly Ser Pro Arg His Thr Asn Ala Asp
1               5                   10                  15

Ala Gly Asn Pro
            20

<210> SEQ ID NO 368
<211> LENGTH: 20
<212> TYPE: PRT
<213> ORGANISM: artificial sequence
<220> FEATURE:
<223> OTHER INFORMATION: Synthetic construct

<400> SEQUENCE: 368

```
Gln Gln His Lys Val His His Gln Asn Pro Asp Arg Ser Thr Gln Asp
1               5                   10                  15

Ala His His Ser
            20

<210> SEQ ID NO 369
<211> LENGTH: 15
<212> TYPE: PRT
<213> ORGANISM: artificial sequence
<220> FEATURE:
<223> OTHER INFORMATION: Synthetic construct

<400> SEQUENCE: 369

His His Gly Thr His His Asn Ala Thr Lys Gln Lys Asn His Val
1               5                   10                  15

<210> SEQ ID NO 370
<211> LENGTH: 15
<212> TYPE: PRT
<213> ORGANISM: artificial sequence
<220> FEATURE:
<223> OTHER INFORMATION: Synthetic construct

<400> SEQUENCE: 370

Ser Thr Leu His Lys Tyr Lys Ser Gln Asp Pro Thr Pro His His
1               5                   10                  15

<210> SEQ ID NO 371
<211> LENGTH: 12
<212> TYPE: PRT
<213> ORGANISM: artificial sequence
<220> FEATURE:
<223> OTHER INFORMATION: Synthetic construct

<400> SEQUENCE: 371

Ser Val Ser Val Gly Met Lys Pro Ser Pro Arg Pro
1               5                   10

<210> SEQ ID NO 372
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 372

Thr Pro Pro Thr Asn Val Leu Met Leu Ala Thr Lys
1               5                   10

<210> SEQ ID NO 373
<211> LENGTH: 12
<212> TYPE: PRT
<213> ORGANISM: artificial sequence
<220> FEATURE:
<223> OTHER INFORMATION: Synthetic construct

<400> SEQUENCE: 373

Thr Pro Pro Glu Leu Leu His Gly Asp Pro Arg Ser
1               5                   10

<210> SEQ ID NO 374
<211> LENGTH: 7
<212> TYPE: PRT
<213> ORGANISM: artificial sequence
<220> FEATURE:
<223> OTHER INFORMATION: synthetic hair-binding peptide
```

-continued

```
<400> SEQUENCE: 374

Asn Thr Ser Gln Leu Ser Thr
1               5

<210> SEQ ID NO 375
<211> LENGTH: 15
<212> TYPE: PRT
<213> ORGANISM: artificial sequence
<220> FEATURE:
<223> OTHER INFORMATION: Synthetic construct

<400> SEQUENCE: 375

Ser Thr Leu His Lys Tyr Lys Ser Gln Asp Pro Thr Pro His His
1               5                   10                  15

<210> SEQ ID NO 376
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 376

Gly Met Pro Ala Met His Trp Ile His Pro Phe Ala
1               5                   10

<210> SEQ ID NO 377
<211> LENGTH: 15
<212> TYPE: PRT
<213> ORGANISM: artificial sequence
<220> FEATURE:
<223> OTHER INFORMATION: synthetic hair-binding peptide

<400> SEQUENCE: 377

His Asp His Lys Asn Gln Lys Glu Thr His Gln Arg His Ala Ala
1               5                   10                  15

<210> SEQ ID NO 378
<211> LENGTH: 20
<212> TYPE: PRT
<213> ORGANISM: artificial sequence
<220> FEATURE:
<223> OTHER INFORMATION: Synthetic construct

<400> SEQUENCE: 378

His Asn His Met Gln Glu Arg Tyr Thr Asp Pro Gln His Ser Pro Ser
1               5                   10                  15

Val Asn Gly Leu
            20

<210> SEQ ID NO 379
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 379

Thr Ala Glu Ile Gln Ser Ser Lys Asn Pro Asn Pro His Pro Gln Arg
1               5                   10                  15

Ser Trp Thr Asn
            20

<210> SEQ ID NO 380
<211> LENGTH: 12
<212> TYPE: PRT
```

```
<213> ORGANISM: artificial sequence
<220> FEATURE:
<223> OTHER INFORMATION: Synthetic construct

<400> SEQUENCE: 380

Lys Arg Gly Arg His Lys Arg Pro Lys Arg His Lys
1               5                   10

<210> SEQ ID NO 381
<211> LENGTH: 7
<212> TYPE: PRT
<213> ORGANISM: artificial sequence
<220> FEATURE:
<223> OTHER INFORMATION: Synthetic construct

<400> SEQUENCE: 381

Arg Leu Leu Arg Leu Leu Arg
1               5

<210> SEQ ID NO 382
<211> LENGTH: 12
<212> TYPE: PRT
<213> ORGANISM: artificial sequence
<220> FEATURE:
<223> OTHER INFORMATION: Synthetic construct

<400> SEQUENCE: 382

His Lys Pro Arg Gly Gly Arg Lys Lys Ala Leu His
1               5                   10

<210> SEQ ID NO 383
<211> LENGTH: 18
<212> TYPE: PRT
<213> ORGANISM: artificial sequence
<220> FEATURE:
<223> OTHER INFORMATION: Synthetic construct

<400> SEQUENCE: 383

Lys Pro Arg Pro Pro His Gly Lys Lys His Arg Pro Lys His Arg Pro
1               5                   10                  15

Lys Lys

<210> SEQ ID NO 384
<211> LENGTH: 18
<212> TYPE: PRT
<213> ORGANISM: artificial sequence
<220> FEATURE:
<223> OTHER INFORMATION: Synthetic construct

<400> SEQUENCE: 384

Arg Gly Arg Pro Lys Lys Gly His Gly Lys Arg Pro Gly His Arg Ala
1               5                   10                  15

Arg Lys

<210> SEQ ID NO 385
<211> LENGTH: 12
<212> TYPE: PRT
<213> ORGANISM: artificial sequence
<220> FEATURE:
<223> OTHER INFORMATION: Synthetic construct

<400> SEQUENCE: 385

Thr Pro Phe His Ser Pro Glu Asn Ala Pro Gly Ser
1               5                   10

<210> SEQ ID NO 386
```

```
<211> LENGTH: 13
<212> TYPE: PRT
<213> ORGANISM: artificial sequence
<220> FEATURE:
<223> OTHER INFORMATION: Synthetic construct

<400> SEQUENCE: 386

Thr Pro Phe His Ser Pro Glu Asn Ala Pro Gly Ser Lys
1               5                   10

<210> SEQ ID NO 387
<211> LENGTH: 16
<212> TYPE: PRT
<213> ORGANISM: artificial sequence
<220> FEATURE:
<223> OTHER INFORMATION: Synthetic construct

<400> SEQUENCE: 387

Thr Pro Phe His Ser Pro Glu Asn Ala Pro Gly Ser Gly Gly Gly Ser
1               5                   10                  15

<210> SEQ ID NO 388
<211> LENGTH: 17
<212> TYPE: PRT
<213> ORGANISM: artificial sequence
<220> FEATURE:
<223> OTHER INFORMATION: Synthetic construct

<400> SEQUENCE: 388

Thr Pro Phe His Ser Pro Glu Asn Ala Pro Gly Ser Gly Gly Gly Ser
1               5                   10                  15

Ser

<210> SEQ ID NO 389
<211> LENGTH: 15
<212> TYPE: PRT
<213> ORGANISM: artificial sequence
<220> FEATURE:
<223> OTHER INFORMATION: Synthetic construct

<400> SEQUENCE: 389

Thr Pro Phe His Ser Pro Glu Asn Ala Pro Gly Ser Gly Gly Gly
1               5                   10                  15

<210> SEQ ID NO 390
<211> LENGTH: 7
<212> TYPE: PRT
<213> ORGANISM: artificial sequence
<220> FEATURE:
<223> OTHER INFORMATION: Synthetic construct

<400> SEQUENCE: 390

Phe Thr Gln Ser Leu Pro Arg
1               5

<210> SEQ ID NO 391
<211> LENGTH: 12
<212> TYPE: PRT
<213> ORGANISM: artificial sequence
<220> FEATURE:
<223> OTHER INFORMATION: Synthetic construct

<400> SEQUENCE: 391

Lys Gln Ala Thr Phe Pro Pro Asn Pro Thr Ala Tyr
1               5                   10

<210> SEQ ID NO 392
```

```
<211> LENGTH: 12
<212> TYPE: PRT
<213> ORGANISM: artificial sequence
<220> FEATURE:
<223> OTHER INFORMATION: Synthetic construct

<400> SEQUENCE: 392

His Gly His Met Val Ser Thr Ser Gln Leu Ser Ile
1               5                   10

<210> SEQ ID NO 393
<211> LENGTH: 7
<212> TYPE: PRT
<213> ORGANISM: artificial sequence
<220> FEATURE:
<223> OTHER INFORMATION: Synthetic construct

<400> SEQUENCE: 393

Leu Ser Pro Ser Arg Met Lys
1               5

<210> SEQ ID NO 394
<211> LENGTH: 7
<212> TYPE: PRT
<213> ORGANISM: artificial sequence
<220> FEATURE:
<223> OTHER INFORMATION: Synthetic construct

<400> SEQUENCE: 394

Leu Pro Ile Pro Arg Met Lys
1               5

<210> SEQ ID NO 395
<211> LENGTH: 7
<212> TYPE: PRT
<213> ORGANISM: artificial sequence
<220> FEATURE:
<223> OTHER INFORMATION: Synthetic construct

<400> SEQUENCE: 395

His Gln Arg Pro Tyr Leu Thr
1               5

<210> SEQ ID NO 396
<211> LENGTH: 7
<212> TYPE: PRT
<213> ORGANISM: artificial sequence
<220> FEATURE:
<223> OTHER INFORMATION: Synthetic construct

<400> SEQUENCE: 396

Phe Pro Pro Leu Leu Arg Leu
1               5

<210> SEQ ID NO 397
<211> LENGTH: 7
<212> TYPE: PRT
<213> ORGANISM: artificial sequence
<220> FEATURE:
<223> OTHER INFORMATION: Synthetic construct

<400> SEQUENCE: 397

Gln Ala Thr Phe Met Tyr Asn
1               5

<210> SEQ ID NO 398
<211> LENGTH: 11
<212> TYPE: PRT
```

```
<213> ORGANISM: artificial sequence
<220> FEATURE:
<223> OTHER INFORMATION: Synthetic construct

<400> SEQUENCE: 398

Val Leu Thr Ser Gln Leu Pro Asn His Ser Met
1               5                   10

<210> SEQ ID NO 399
<211> LENGTH: 7
<212> TYPE: PRT
<213> ORGANISM: artificial sequence
<220> FEATURE:
<223> OTHER INFORMATION: Synthetic construct

<400> SEQUENCE: 399

His Ser Thr Ala Tyr Leu Thr
1               5

<210> SEQ ID NO 400
<211> LENGTH: 12
<212> TYPE: PRT
<213> ORGANISM: artificial sequence
<220> FEATURE:
<223> OTHER INFORMATION: Synthetic construct

<400> SEQUENCE: 400

Ala Pro Gln Gln Arg Pro Met Lys Thr Phe Asn Thr
1               5                   10

<210> SEQ ID NO 401
<211> LENGTH: 12
<212> TYPE: PRT
<213> ORGANISM: artificial sequence
<220> FEATURE:
<223> OTHER INFORMATION: Synthetic construct

<400> SEQUENCE: 401

Ala Pro Gln Gln Arg Pro Met Lys Thr Val Gln Tyr
1               5                   10

<210> SEQ ID NO 402
<211> LENGTH: 7
<212> TYPE: PRT
<213> ORGANISM: artificial sequence
<220> FEATURE:
<223> OTHER INFORMATION: Synthetic construct

<400> SEQUENCE: 402

Pro Pro Trp Leu Asp Leu Leu
1               5

<210> SEQ ID NO 403
<211> LENGTH: 7
<212> TYPE: PRT
<213> ORGANISM: artificial sequence
<220> FEATURE:
<223> OTHER INFORMATION: Synthetic construct

<400> SEQUENCE: 403

Pro Pro Trp Thr Phe Pro Leu
1               5

<210> SEQ ID NO 404
<211> LENGTH: 7
<212> TYPE: PRT
<213> ORGANISM: artificial sequence
<220> FEATURE:
```

```
<223> OTHER INFORMATION: Synthetic construct

<400> SEQUENCE: 404

Ser Val Thr His Leu Thr Ser
1               5

<210> SEQ ID NO 405
<211> LENGTH: 7
<212> TYPE: PRT
<213> ORGANISM: artificial sequence
<220> FEATURE:
<223> OTHER INFORMATION: Synthetic construct

<400> SEQUENCE: 405

Val Ile Thr Arg Leu Thr Ser
1               5

<210> SEQ ID NO 406
<211> LENGTH: 12
<212> TYPE: PRT
<213> ORGANISM: artificial sequence
<220> FEATURE:
<223> OTHER INFORMATION: Synthetic construct

<400> SEQUENCE: 406

Asp Leu Lys Pro Pro Leu Leu Ala Leu Ser Lys Val
1               5                   10

<210> SEQ ID NO 407
<211> LENGTH: 12
<212> TYPE: PRT
<213> ORGANISM: artificial sequence
<220> FEATURE:
<223> OTHER INFORMATION: Synthetic construct

<400> SEQUENCE: 407

Ser His Pro Ser Gly Ala Leu Gln Glu Gly Thr Phe
1               5                   10

<210> SEQ ID NO 408
<211> LENGTH: 12
<212> TYPE: PRT
<213> ORGANISM: artificial sequence
<220> FEATURE:
<223> OTHER INFORMATION: Synthetic construct

<400> SEQUENCE: 408

Phe Pro Leu Thr Ser Lys Pro Ser Gly Ala Cys Thr
1               5                   10

<210> SEQ ID NO 409
<211> LENGTH: 12
<212> TYPE: PRT
<213> ORGANISM: artificial sequence
<220> FEATURE:
<223> OTHER INFORMATION: Synthetic construct

<400> SEQUENCE: 409

Asp Leu Lys Pro Pro Leu Leu Ala Leu Ser Lys Val
1               5                   10

<210> SEQ ID NO 410
<211> LENGTH: 7
<212> TYPE: PRT
<213> ORGANISM: artificial sequence
<220> FEATURE:
<223> OTHER INFORMATION: Synthetic construct
```

-continued

```
<400> SEQUENCE: 410

Pro Leu Leu Ala Leu His Ser
1               5

<210> SEQ ID NO 411
<211> LENGTH: 7
<212> TYPE: PRT
<213> ORGANISM: artificial sequence
<220> FEATURE:
<223> OTHER INFORMATION: Synthetic construct

<400> SEQUENCE: 411

Val Pro Ile Ser Thr Gln Ile
1               5

<210> SEQ ID NO 412
<211> LENGTH: 12
<212> TYPE: PRT
<213> ORGANISM: artificial sequence
<220> FEATURE:
<223> OTHER INFORMATION: Synthetic construct

<400> SEQUENCE: 412

Tyr Ala Lys Gln His Tyr Pro Ile Ser Thr Phe Lys
1               5                   10

<210> SEQ ID NO 413
<211> LENGTH: 7
<212> TYPE: PRT
<213> ORGANISM: artificial sequence
<220> FEATURE:
<223> OTHER INFORMATION: Synthetic construct

<400> SEQUENCE: 413

His Ser Thr Ala Tyr Leu Thr
1               5

<210> SEQ ID NO 414
<211> LENGTH: 12
<212> TYPE: PRT
<213> ORGANISM: artificial sequence
<220> FEATURE:
<223> OTHER INFORMATION: Synthetic construct

<400> SEQUENCE: 414

Ser Thr Ala Tyr Leu Val Ala Met Ser Ala Ala Pro
1               5                   10

<210> SEQ ID NO 415
<211> LENGTH: 12
<212> TYPE: PRT
<213> ORGANISM: artificial sequence
<220> FEATURE:
<223> OTHER INFORMATION: Synthetic construct

<400> SEQUENCE: 415

Ser Val Ser Val Gly Met Lys Pro Ser Pro Arg Pro
1               5                   10

<210> SEQ ID NO 416
<211> LENGTH: 12
<212> TYPE: PRT
<213> ORGANISM: artificial sequence
<220> FEATURE:
<223> OTHER INFORMATION: Synthetic construct

<400> SEQUENCE: 416
```

```
Thr Met Gly Phe Thr Ala Pro Arg Phe Pro His Tyr
1               5                   10
```

<210> SEQ ID NO 417
<211> LENGTH: 12
<212> TYPE: PRT
<213> ORGANISM: artificial sequence
<220> FEATURE:
<223> OTHER INFORMATION: Synthetic construct

<400> SEQUENCE: 417

```
Asn Leu Gln His Ser Val Gly Thr Ser Pro Val Trp
1               5                   10
```

<210> SEQ ID NO 418
<211> LENGTH: 15
<212> TYPE: PRT
<213> ORGANISM: artificial sequence
<220> FEATURE:
<223> OTHER INFORMATION: Synthetic construct

<400> SEQUENCE: 418

```
Gln Leu Ser Tyr His Ala Tyr Pro Gln Ala Asn His His Ala Pro
1               5                   10                  15
```

<210> SEQ ID NO 419
<211> LENGTH: 12
<212> TYPE: PRT
<213> ORGANISM: artificial sequence
<220> FEATURE:
<223> OTHER INFORMATION: Synthetic construct

<400> SEQUENCE: 419

```
Asn Gln Ala Ala Ser Ile Thr Lys Arg Val Pro Tyr
1               5                   10
```

<210> SEQ ID NO 420
<211> LENGTH: 14
<212> TYPE: PRT
<213> ORGANISM: artificial sequence
<220> FEATURE:
<223> OTHER INFORMATION: Synthetic construct

<400> SEQUENCE: 420

```
Ser Gly Cys His Leu Val Tyr Asp Asn Gly Phe Cys Asp His
1               5                   10
```

<210> SEQ ID NO 421
<211> LENGTH: 14
<212> TYPE: PRT
<213> ORGANISM: artificial sequence
<220> FEATURE:
<223> OTHER INFORMATION: Synthetic construct

<400> SEQUENCE: 421

```
Ala Ser Cys Pro Ser Ala Ser His Ala Asp Pro Cys Ala His
1               5                   10
```

<210> SEQ ID NO 422
<211> LENGTH: 14
<212> TYPE: PRT
<213> ORGANISM: artificial sequence
<220> FEATURE:
<223> OTHER INFORMATION: Synthetic construct

<400> SEQUENCE: 422

```
Asn Leu Cys Asp Ser Ala Arg Asp Ser Pro Arg Cys Lys Val
1               5                   10
```

<210> SEQ ID NO 423
<211> LENGTH: 12
<212> TYPE: PRT
<213> ORGANISM: artificial sequence
<220> FEATURE:
<223> OTHER INFORMATION: Synthetic construct

<400> SEQUENCE: 423

Asn His Ser Asn Trp Lys Thr Ala Ala Asp Phe Leu
1               5                   10

<210> SEQ ID NO 424
<211> LENGTH: 12
<212> TYPE: PRT
<213> ORGANISM: artificial sequence
<220> FEATURE:
<223> OTHER INFORMATION: Synthetic construct

<400> SEQUENCE: 424

Gly Ser Ser Thr Val Gly Arg Pro Leu Ser Tyr Glu
1               5                   10

<210> SEQ ID NO 425
<211> LENGTH: 12
<212> TYPE: PRT
<213> ORGANISM: artificial sequence
<220> FEATURE:
<223> OTHER INFORMATION: Synthetic construct

<400> SEQUENCE: 425

Ser Asp Thr Ile Ser Arg Leu His Val Ser Met Thr
1               5                   10

<210> SEQ ID NO 426
<211> LENGTH: 12
<212> TYPE: PRT
<213> ORGANISM: artificial sequence
<220> FEATURE:
<223> OTHER INFORMATION: Synthetic construct

<400> SEQUENCE: 426

Ser Pro Leu Thr Val Pro Tyr Glu Arg Lys Leu Leu
1               5                   10

<210> SEQ ID NO 427
<211> LENGTH: 12
<212> TYPE: PRT
<213> ORGANISM: artificial sequence
<220> FEATURE:
<223> OTHER INFORMATION: Synthetic construct

<400> SEQUENCE: 427

Ser Pro Tyr Pro Ser Trp Ser Thr Pro Ala Gly Arg
1               5                   10

<210> SEQ ID NO 428
<211> LENGTH: 12
<212> TYPE: PRT
<213> ORGANISM: artificial sequence
<220> FEATURE:
<223> OTHER INFORMATION: Synthetic construct

<400> SEQUENCE: 428

Val Gln Pro Ile Thr Asn Thr Arg Tyr Glu Gly Gly
1               5                   10

```
<210> SEQ ID NO 429
<211> LENGTH: 12
<212> TYPE: PRT
<213> ORGANISM: artificial sequence
<220> FEATURE:
<223> OTHER INFORMATION: Synthetic construct

<400> SEQUENCE: 429

Trp Pro Met His Pro Glu Lys Gly Ser Arg Trp Ser
1               5                   10

<210> SEQ ID NO 430
<211> LENGTH: 14
<212> TYPE: PRT
<213> ORGANISM: artificial sequence
<220> FEATURE:
<223> OTHER INFORMATION: Synthetic construct

<400> SEQUENCE: 430

Asp Ala Cys Ser Gly Asn Gly His Pro Asn Asn Cys Asp Arg
1               5                   10

<210> SEQ ID NO 431
<211> LENGTH: 14
<212> TYPE: PRT
<213> ORGANISM: artificial sequence
<220> FEATURE:
<223> OTHER INFORMATION: Synthetic construct

<400> SEQUENCE: 431

Asp His Cys Leu Gly Arg Gln Leu Gln Pro Val Cys Tyr Pro
1               5                   10

<210> SEQ ID NO 432
<211> LENGTH: 14
<212> TYPE: PRT
<213> ORGANISM: artificial sequence
<220> FEATURE:
<223> OTHER INFORMATION: Synthetic construct

<400> SEQUENCE: 432

Asp Trp Cys Asp Thr Ile Ile Pro Gly Arg Thr Cys His Gly
1               5                   10

<210> SEQ ID NO 433
<211> LENGTH: 12
<212> TYPE: PRT
<213> ORGANISM: artificial sequence
<220> FEATURE:
<223> OTHER INFORMATION: Synthetic construct

<400> SEQUENCE: 433

Ala Leu Pro Arg Ile Ala Asn Thr Trp Ser Pro Ser
1               5                   10

<210> SEQ ID NO 434
<211> LENGTH: 12
<212> TYPE: PRT
<213> ORGANISM: artificial sequence
<220> FEATURE:
<223> OTHER INFORMATION: Synthetic construct

<400> SEQUENCE: 434

Tyr Pro Ser Phe Ser Pro Thr Tyr Arg Pro Ala Phe
1               5                   10

<210> SEQ ID NO 435
<211> LENGTH: 20
```

```
<212> TYPE: PRT
<213> ORGANISM: artificial sequence
<220> FEATURE:
<223> OTHER INFORMATION: Synthetic construct

<400> SEQUENCE: 435

Ala His Pro Glu Ser Leu Gly Ile Lys Tyr Ala Leu Asp Gly Asn Ser
1               5                   10                  15

Asp Pro His Ala
            20

<210> SEQ ID NO 436
<211> LENGTH: 20
<212> TYPE: PRT
<213> ORGANISM: artificial sequence
<220> FEATURE:
<223> OTHER INFORMATION: Synthetic construct

<400> SEQUENCE: 436

Ala Ser Val Ser Asn Tyr Pro Pro Ile His His Leu Ala Thr Ser Asn
1               5                   10                  15

Thr Thr Val Asn
            20

<210> SEQ ID NO 437
<211> LENGTH: 14
<212> TYPE: PRT
<213> ORGANISM: artificial sequence
<220> FEATURE:
<223> OTHER INFORMATION: Synthetic construct

<400> SEQUENCE: 437

Asp Glu Cys Met Glu Pro Leu Asn Ala Ala His Cys Trp Arg
1               5                   10

<210> SEQ ID NO 438
<211> LENGTH: 14
<212> TYPE: PRT
<213> ORGANISM: artificial sequence
<220> FEATURE:
<223> OTHER INFORMATION: Synthetic construct

<400> SEQUENCE: 438

Asp Glu Cys Met His Gly Ser Asp Val Glu Phe Cys Thr Ser
1               5                   10

<210> SEQ ID NO 439
<211> LENGTH: 14
<212> TYPE: PRT
<213> ORGANISM: artificial sequence
<220> FEATURE:
<223> OTHER INFORMATION: Synthetic construct

<400> SEQUENCE: 439

Asp Leu Cys Ser Met Gln Met Met Asn Thr Gly Cys His Tyr
1               5                   10

<210> SEQ ID NO 440
<211> LENGTH: 14
<212> TYPE: PRT
<213> ORGANISM: artificial sequence
<220> FEATURE:
<223> OTHER INFORMATION: Synthetic construct

<400> SEQUENCE: 440

Asp Leu Cys Ser Ser Pro Ser Thr Trp Gly Ser Cys Ile Arg
1               5                   10
```

```
<210> SEQ ID NO 441
<211> LENGTH: 20
<212> TYPE: PRT
<213> ORGANISM: artificial sequence
<220> FEATURE:
<223> OTHER INFORMATION: Synthetic construct

<400> SEQUENCE: 441

Asp Pro Asn Glu Ser Asn Tyr Glu Asn Ala Thr Thr Val Ser Gln Pro
1               5                   10                  15

Thr Arg His Leu
            20

<210> SEQ ID NO 442
<211> LENGTH: 20
<212> TYPE: PRT
<213> ORGANISM: artificial sequence
<220> FEATURE:
<223> OTHER INFORMATION: Synthetic construct

<400> SEQUENCE: 442

Glu Pro Thr His Pro Thr Met Arg Ala Gln Met His Gln Ser Leu Arg
1               5                   10                  15

Ser Ser Ser Pro
            20

<210> SEQ ID NO 443
<211> LENGTH: 20
<212> TYPE: PRT
<213> ORGANISM: artificial sequence
<220> FEATURE:
<223> OTHER INFORMATION: Synthetic construct

<400> SEQUENCE: 443

Gly Asn Thr Asp Thr Thr Pro Pro Asn Ala Val Met Glu Pro Thr Val
1               5                   10                  15

Gln His Lys Trp
            20

<210> SEQ ID NO 444
<211> LENGTH: 15
<212> TYPE: PRT
<213> ORGANISM: artificial sequence
<220> FEATURE:
<223> OTHER INFORMATION: Synthetic construct

<400> SEQUENCE: 444

Asn Gly Pro Asp Met Val Gln Ser Val Gly Lys His Lys Asn Ser
1               5                   10                  15

<210> SEQ ID NO 445
<211> LENGTH: 15
<212> TYPE: PRT
<213> ORGANISM: artificial sequence
<220> FEATURE:
<223> OTHER INFORMATION: Synthetic construct

<400> SEQUENCE: 445

Asn Gly Pro Glu Val Arg Gln Ile Pro Ala Asn Phe Glu Lys Leu
1               5                   10                  15

<210> SEQ ID NO 446
<211> LENGTH: 20
<212> TYPE: PRT
<213> ORGANISM: artificial sequence
```

```
<220> FEATURE:
<223> OTHER INFORMATION: Synthetic construct

<400> SEQUENCE: 446

Asn Asn Thr Ser Ala Asp Asn Pro Pro Glu Thr Asp Ser Lys His His
1               5                   10                  15

Leu Ser Met Ser
            20

<210> SEQ ID NO 447
<211> LENGTH: 20
<212> TYPE: PRT
<213> ORGANISM: artificial sequence
<220> FEATURE:
<223> OTHER INFORMATION: Synthetic construct

<400> SEQUENCE: 447

Asn Asn Thr Trp Pro Glu Gly Ala Gly His Thr Met Pro Ser Thr Asn
1               5                   10                  15

Ile Arg Gln Ala
            20

<210> SEQ ID NO 448
<211> LENGTH: 20
<212> TYPE: PRT
<213> ORGANISM: artificial sequence
<220> FEATURE:
<223> OTHER INFORMATION: Synthetic construct

<400> SEQUENCE: 448

Asn Pro Thr Ala Thr Pro His Met Lys Asp Pro Met His Ser Asn Ala
1               5                   10                  15

His Ser Ser Ala
            20

<210> SEQ ID NO 449
<211> LENGTH: 20
<212> TYPE: PRT
<213> ORGANISM: artificial sequence
<220> FEATURE:
<223> OTHER INFORMATION: Synthetic construct

<400> SEQUENCE: 449

Asn Pro Thr Asp His Ile Pro Ala Asn Ser Thr Asn Ser Arg Val Ser
1               5                   10                  15

Lys Gly Asn Thr
            20

<210> SEQ ID NO 450
<211> LENGTH: 15
<212> TYPE: PRT
<213> ORGANISM: artificial sequence
<220> FEATURE:
<223> OTHER INFORMATION: Synthetic construct

<400> SEQUENCE: 450

Asn Pro Thr Asp Ser Thr His Met Met His Ala Arg Asn His Glu
1               5                   10                  15

<210> SEQ ID NO 451
<211> LENGTH: 14
<212> TYPE: PRT
<213> ORGANISM: artificial sequence
<220> FEATURE:
<223> OTHER INFORMATION: Synthetic construct
```

```
<400> SEQUENCE: 451

Gln His Cys Ile Thr Glu Arg Leu His Pro Pro Cys Thr Lys
1               5                   10

<210> SEQ ID NO 452
<211> LENGTH: 14
<212> TYPE: PRT
<213> ORGANISM: artificial sequence
<220> FEATURE:
<223> OTHER INFORMATION: Synthetic construct

<400> SEQUENCE: 452

Thr Pro Cys Ala Pro Ala Ser Phe Asn Pro His Cys Ser Arg
1               5                   10

<210> SEQ ID NO 453
<211> LENGTH: 14
<212> TYPE: PRT
<213> ORGANISM: artificial sequence
<220> FEATURE:
<223> OTHER INFORMATION: Synthetic construct

<400> SEQUENCE: 453

Thr Pro Cys Ala Thr Tyr Pro His Phe Ser Gly Cys Arg Ala
1               5                   10

<210> SEQ ID NO 454
<211> LENGTH: 20
<212> TYPE: PRT
<213> ORGANISM: artificial sequence
<220> FEATURE:
<223> OTHER INFORMATION: Synthetic construct

<400> SEQUENCE: 454

Trp Cys Thr Asp Phe Cys Thr Arg Ser Thr Pro Thr Ser Thr Ser Arg
1               5                   10                  15

Ser Thr Thr Ser
            20

<210> SEQ ID NO 455
<211> LENGTH: 20
<212> TYPE: PRT
<213> ORGANISM: artificial sequence
<220> FEATURE:
<223> OTHER INFORMATION: Synthetic construct

<400> SEQUENCE: 455

Ala Pro Pro Leu Lys Thr Tyr Met Gln Glu Arg Glu Leu Thr Met Ser
1               5                   10                  15

Gln Asn Lys Asp
            20

<210> SEQ ID NO 456
<211> LENGTH: 20
<212> TYPE: PRT
<213> ORGANISM: artificial sequence
<220> FEATURE:
<223> OTHER INFORMATION: Synthetic construct

<400> SEQUENCE: 456

Glu Pro Pro Thr Arg Thr Arg Val Asn Asn His Thr Val Thr Val Gln
1               5                   10                  15

Ala Gln Gln His
            20
```

```
<210> SEQ ID NO 457
<211> LENGTH: 14
<212> TYPE: PRT
<213> ORGANISM: artificial sequence
<220> FEATURE:
<223> OTHER INFORMATION: Synthetic construct

<400> SEQUENCE: 457

Gly Tyr Cys Leu Arg Gly Asp Glu Pro Ala Val Cys Ser Gly
1               5                   10

<210> SEQ ID NO 458
<211> LENGTH: 20
<212> TYPE: PRT
<213> ORGANISM: artificial sequence
<220> FEATURE:
<223> OTHER INFORMATION: Synthetic construct

<400> SEQUENCE: 458

Leu Ser Ser Lys Asp Phe Gly Val Thr Asn Thr Asp Gln Arg Thr Tyr
1               5                   10                  15

Asp Tyr Thr Thr
            20

<210> SEQ ID NO 459
<211> LENGTH: 14
<212> TYPE: PRT
<213> ORGANISM: artificial sequence
<220> FEATURE:
<223> OTHER INFORMATION: Synthetic construct

<400> SEQUENCE: 459

Asn Phe Cys Glu Thr Gln Leu Asp Leu Ser Val Cys Thr Val
1               5                   10

<210> SEQ ID NO 460
<211> LENGTH: 14
<212> TYPE: PRT
<213> ORGANISM: artificial sequence
<220> FEATURE:
<223> OTHER INFORMATION: Synthetic construct

<400> SEQUENCE: 460

Asn Thr Cys Gln Pro Thr Lys Asn Ala Thr Pro Cys Ser Ala
1               5                   10

<210> SEQ ID NO 461
<211> LENGTH: 20
<212> TYPE: PRT
<213> ORGANISM: artificial sequence
<220> FEATURE:
<223> OTHER INFORMATION: Synthetic construct

<400> SEQUENCE: 461

Pro Ser Glu Pro Glu Arg Arg Asp Arg Asn Ile Ala Ala Asn Ala Gly
1               5                   10                  15

Arg Phe Asn Thr
            20

<210> SEQ ID NO 462
<211> LENGTH: 18
<212> TYPE: PRT
<213> ORGANISM: artificial sequence
<220> FEATURE:
<223> OTHER INFORMATION: Synthetic construct

<400> SEQUENCE: 462
```

```
Thr His Asn Met Ser His Phe Pro Pro Ser Gly His Pro Lys Arg Thr
1               5                   10                  15

Ala Thr
```

```
<210> SEQ ID NO 463
<211> LENGTH: 14
<212> TYPE: PRT
<213> ORGANISM: artificial sequence
<220> FEATURE:
<223> OTHER INFORMATION: Synthetic construct

<400> SEQUENCE: 463

Thr Thr Cys Pro Thr Met Gly Thr Tyr His Val Cys Trp Leu
1               5                   10
```

```
<210> SEQ ID NO 464
<211> LENGTH: 20
<212> TYPE: PRT
<213> ORGANISM: artificial sequence
<220> FEATURE:
<223> OTHER INFORMATION: Synthetic construct

<400> SEQUENCE: 464

Tyr Cys Ala Asp His Thr Pro Asp Pro Ala Asn Pro Asn Lys Ile Cys
1               5                   10                  15

Gly Tyr Ser His
            20
```

```
<210> SEQ ID NO 465
<211> LENGTH: 20
<212> TYPE: PRT
<213> ORGANISM: artificial sequence
<220> FEATURE:
<223> OTHER INFORMATION: Synthetic construct

<400> SEQUENCE: 465

Ala Ala Asn Pro His Thr Glu Trp Asp Arg Asp Ala Phe Gln Leu Ala
1               5                   10                  15

Met Pro Pro Lys
            20
```

```
<210> SEQ ID NO 466
<211> LENGTH: 20
<212> TYPE: PRT
<213> ORGANISM: artificial sequence
<220> FEATURE:
<223> OTHER INFORMATION: Synthetic construct

<400> SEQUENCE: 466

Asp Leu His Pro Met Asp Pro Ser Asn Lys Arg Pro Asp Asn Pro Ser
1               5                   10                  15

Asp Leu His Thr
            20
```

```
<210> SEQ ID NO 467
<211> LENGTH: 14
<212> TYPE: PRT
<213> ORGANISM: artificial sequence
<220> FEATURE:
<223> OTHER INFORMATION: Synthetic construct

<400> SEQUENCE: 467

Glu Ser Cys Val Ser Asn Ala Leu Met Asn Gln Cys Ile Tyr
1               5                   10
```

```
<210> SEQ ID NO 468
<211> LENGTH: 20
<212> TYPE: PRT
<213> ORGANISM: artificial sequence
<220> FEATURE:
<223> OTHER INFORMATION: Synthetic construct

<400> SEQUENCE: 468

His Asn Lys Ala Asp Ser Trp Asp Pro Asp Leu Pro Pro His Ala Gly
1               5                   10                  15

Met Ser Leu Gly
            20

<210> SEQ ID NO 469
<211> LENGTH: 20
<212> TYPE: PRT
<213> ORGANISM: artificial sequence
<220> FEATURE:
<223> OTHER INFORMATION: Synthetic construct

<400> SEQUENCE: 469

Leu Asn Asp Gln Arg Lys Pro Gly Pro Pro Thr Met Pro Thr His Ser
1               5                   10                  15

Pro Ala Val Gly
            20

<210> SEQ ID NO 470
<211> LENGTH: 14
<212> TYPE: PRT
<213> ORGANISM: artificial sequence
<220> FEATURE:
<223> OTHER INFORMATION: Synthetic construct

<400> SEQUENCE: 470

Asn Thr Cys Ala Thr Ser Pro Asn Ser Tyr Thr Cys Ser Asn
1               5                   10

<210> SEQ ID NO 471
<211> LENGTH: 14
<212> TYPE: PRT
<213> ORGANISM: artificial sequence
<220> FEATURE:
<223> OTHER INFORMATION: Synthetic construct

<400> SEQUENCE: 471

Ser Asp Cys Thr Ala Gly Leu Val Pro Pro Leu Cys Ala Thr
1               5                   10

<210> SEQ ID NO 472
<211> LENGTH: 20
<212> TYPE: PRT
<213> ORGANISM: artificial sequence
<220> FEATURE:
<223> OTHER INFORMATION: Synthetic construct

<400> SEQUENCE: 472

Thr Ile Glu Ser Ser Gln His Ser Arg Thr His Gln Gln Asn Tyr Gly
1               5                   10                  15

Ser Thr Lys Thr
            20

<210> SEQ ID NO 473
<211> LENGTH: 20
<212> TYPE: PRT
<213> ORGANISM: artificial sequence
<220> FEATURE:
<223> OTHER INFORMATION: Synthetic construct
```

```
<400> SEQUENCE: 473

Val Gly Thr Met Lys Gln His Pro Thr Thr Thr Gln Pro Pro Arg Val
1               5                   10                  15

Ser Ala Thr Asn
            20

<210> SEQ ID NO 474
<211> LENGTH: 20
<212> TYPE: PRT
<213> ORGANISM: artificial sequence
<220> FEATURE:
<223> OTHER INFORMATION: Synthetic construct

<400> SEQUENCE: 474

Tyr Ser Glu Thr Pro Asn Asp Gln Lys Pro Asn Pro His Tyr Lys Val
1               5                   10                  15

Ser Gly Thr Lys
            20
```

PMMA BINDING PEPTIDES

This application claims the benefit of U.S. Provisional Patent Application No. 61/179,831 filed May 20, 2009.

FIELD OF THE INVENTION

The invention relates to peptides having affinity for polymethyl methacrylate polymer as well as peptide-based reagents comprising at least one of the present polymethyl methacrylate-binding peptides.

BACKGROUND OF THE INVENTION

Polymethyl methacrylate resin (PMMA; CAS RN: 9011-14-7) is a clear polymer developed as a glass substitute. It is commonly referred to as acrylic glass or acrylic and marketed under trademarks such as: PLEXIGLAS™, PERSPEX™, ACRYLITE™, ACRYLPLAST™, and LUCITE™. PMMA has several advantages over silicon glass such as lower density, higher impact strength, higher shatter resistance, and a lower processing temperature. PMMA is commonly found in large windows, aquariums, vehicle rear lights, dentures, and paint coatings, to name a few.

The ubiquitous use of PMMA in industry makes it a prime material candidate for a variety of applications in which PMMA comprises some or all of a surface. However, the physical properties of PMMA may be undesirable for certain applications. Under such circumstances a coating may be applied to mask or alter the undesirable property.

One way to alter, mask or enhance certain properties of a PMMA polymer surface is to couple to the surface an agent that provides a desired effect or benefit (a "benefit agent"). However, many benefit agents do not durably adhere to PMMA. As such, there is a need to provide a reagent suitable for enhancing the delivery and/or durability of a benefit agent targeted to a surface comprising PMMA polymer. Preferably, the reagent has a least one portion having strong affinity for PMMA polymer.

Peptide-based reagents can be prepared to couple a benefit agent to a target surface. Peptide sequences that bind to surface comprising PMMA polymer are described by Cunningham et al. in U.S. Patent Application Publication No. 2007/0265431. However, only phage display-identified PMMA-binding peptides are provided by Cunningham et al. It is known that other display techniques, such as mRNA-display, can provide greater sequence diversity that may result in the identification of linear peptides having stronger affinity for the target substrate (Gold, L., (2001) *PNAS.* 98(9):4825-4826). Additionally, some commercial applications may use peptide reagents comprising a plurality of different PMMA-binding peptides. As such, there is a need to identify additional PMMA-binding peptides having strong affinity for surfaces comprising PMMA polymer.

The problem to be solved is to provide additional PMMA-binding peptides as well as peptide-based reagents suitable for either (1) coupling a first surface comprising PMMA polymer to a benefit agent or (2) coupling a benefit agent comprising PMMA polymer to a second target surface to deliver a benefit to the second target surface.

SUMMARY OF THE INVENTION

The stated problem has been solved by the identification of PMMA-binding peptides having strong affinity for PMMA polymer. The present PMMA-binding peptides were identified using mRNA-display. One or more of the present PMMA-binding peptides may be used to prepare peptide-based reagents for use in the delivery of at least one benefit agent to a material comprising PMMA resin. One or more of the present PMMA-binding peptides may also be used to form a beneficial film on and/or coupled a benefit agent to a PMMA polymer. The peptide-based reagents may also be used to couple a benefit agent comprising PMMA (the first target surface) to a second target surface. The first and second target surfaces may be the same or different.

Many of the present PMMA-binding peptides share similar structures based on prevalence of conserved sequences identified using mRNA-display. As such, sequences of PMMA-binding peptides sharing significant structural similarity are provided.

In one embodiment, a peptide having affinity for polymethyl methacrylate (i.e. a "PMMA-binding peptide") is provided, said polypeptide having the general structure (SEQ ID NO: 21):

$$IGWWLLRYWLYLQWKLYX_1WWFSVLWTF$$

wherein $X_1$ is V or A.

One or more of the present PMMA-binding peptides may be used to prepare peptide reagents. Peptide reagents are also provided having a general structure selected from the group consisting of:

$$([PBP]_n\text{-}[L]_x\text{-}BA\text{-}[L]_y)_m; \text{ and}$$

$$([PBP]_n\text{-}[L]_x\text{-}TBD\text{-}[L]_y)_m$$

wherein:
  i) PBP is a polymethyl methacrylate-binding peptide;
  ii) L is a linker molecule;
  iii) BA is at least one benefit agent;
  iv) TBD is a target binding domain;
  v) x and y independently range from 0 to 10;
  vi) n=1 to 10; and
  vii) m=1 to 10;
  wherein the polymethyl methacrylate-binding peptide comprises an amino acid sequence of SEQ ID NO: 21.

In another embodiment, a method for binding a peptide-based reagent to PMMA is provided comprising:
  a) providing at least one peptide or peptide reagent comprising SEQ ID NO: 21; and
  b) contacting the peptide-based reagent of (a) with a surface comprising PMMA whereby the peptide-based reagent binds to the PMMA.

The present PMMA-binding peptides and/or peptide reagents may be used in personal care compositions to delivery or enhance the durability of a benefit agent to a body surface. As such, a personal care composition comprising one or more of the present PMMA-binding peptides and/or peptide reagents is also provided.

BRIEF DESCRIPTION OF THE BIOLOGICAL SEQUENCES

The following sequences comply with 37 C.F.R. 1.821-1.825 ("Requirements for patent applications Containing Nucleotide Sequences and/or Amino Acid Sequence Disclosures—the Sequence Rules") and are consistent with World Intellectual Property Organization (WIPO) Standard ST. 25 (1998) and the sequence listing requirements of the EPC and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

SEQ ID NOs: 1-35 are the amino acid sequences of peptides having strong affinity for a surface comprising PMMA polymer.

SEQ ID NO: 5 is the amino acid sequence of a peptide classified herein as Group "A" PMMA polymer-binding peptides. Examples of PMMA-binding peptides belonging to Group "A" are selected from the group consisting of SEQ ID NOs: 1, 2, 3, and 4 and 5.

SEQ ID NO: 9 is the amino acid sequence of a peptide classified herein as Group "B" PMMA polymer-binding peptides. Examples of PMMA-binding peptides belonging to Group "B" are selected from the group consisting of SEQ ID NOs: 6, 7, 8 and 9.

SEQ ID NO: 14 is the amino acid sequence of a peptide classified herein as Group "C" PMMA polymer-binding peptides. Examples of PMMA-binding peptides belonging to Group "C" are selected from the group consisting of SEQ ID NOs: 10, 11, 12, 13, and 14.

SEQ ID NO: 18 is the amino acid sequence of a peptide classified herein as Group "D" PMMA polymer-binding peptides. Examples of PMMA-binding peptides belonging to Group "D" are selected from the group consisting of SEQ ID NOs: 15, 16, 17, and 18.

SEQ ID NO: 21 is the amino acid sequence of a peptide classified herein as Group "E" PMMA polymer-binding peptides. Examples of PMMA-binding peptides belonging to Group "E" are selected from the group consisting of SEQ ID NOs: 19, 20, and 21.

SEQ ID NO: 24 is the amino acid sequence of a peptide classified herein as Group "F" PMMA polymer-binding peptides. Examples of PMMA-binding peptides belonging to Group "F" are selected from the group consisting of SEQ ID NOs: 22, 23, and 24.

SEQ ID NO: 27 is the amino acid sequence of a peptide classified herein as Group "G" PMMA polymer-binding peptides. Examples of PMMA-binding peptides belonging to Group "G" are selected from the group consisting of SEQ ID NOs: 25, 26, and 27.

SEQ ID NOs: 28-35 are additional amino acid sequences of peptides having strong affinity for PMMA polymer.

SEQ ID NO: 36 is the amino acid sequence of the N-terminal constant region used in the present display library.

SEQ ID NO: 37 is the amino acid sequence of the C-terminal constant region used in the present display library.

SEQ ID NO: 38 is the nucleic acid sequence of the oligonucleotide portion of the MHA-oligonucleotide linker used in preparing the fusion molecules.

SEQ ID NOs: 39 and 40 are primers.

SEQ ID NO: 41 is the amino acid sequence of the Caspase-3 cleavage sequence.

SEQ ID NOs: 42-100 are the amino acid sequence of polymer-binding peptides.

SEQ ID NOs: 101-104 are the amino acid sequence of cellulose acetate-binding peptides.

SEQ ID NOs: 105-159 are the amino acid sequences of pigment-binding peptides.

SEQ ID NOs: 160-174 are the amino acid sequence of clay-binding peptides.

SEQ ID NOs: 175-200 are the amino acid sequences of calcium carbonate-binding peptides.

SEQ ID NOs: 201-223 are the amino acid sequences of silica-binding peptides.

SEQ ID NOs: 224-252 are the amino acid sequences of antimicrobial peptides.

SEQ ID NOs: 253-254 are the amino acid sequences of several peptide linkers.

SEQ ID NOs: 255-256 are the amino acid sequences of several peptide bridges.

SEQ ID NO: 257 is the amino acid sequence of PMMA-binding peptide of SEQ ID NO: 6 further comprising a C-terminal lysine residue.

SEQ ID NOs: 258-474 are examples of peptides having affinity for a body surface wherein SEQ ID NOs: 258-384 bind to hair; SEQ ID NOs 380-432 binding to skin; SEQ ID NOs: 433-434 bind to nail; SEQ ID NOs: 435-454 bind to tooth pellicle; and SEQ ID NOs: 455-474 bind to tooth enamel.

DETAILED DESCRIPTION OF THE INVENTION

Provided herein are peptides having strong affinity for PMMA (PMMA-binding peptides) as well as peptide-based reagents comprising at least one of said PMMA-binding peptides. The peptide-based reagents are useful for coupling a benefit agent to a surface comprising PMMA polymer or for coupling at least one first surface comprising polymethyl methacrylate (PMMA) polymer to at least one second target surface. For example, a particulate benefit agent comprising a surface of PMMA polymer, such as a PMMA-coated pigment, can be coupled to a second surface, such as a body surface. The first and second target surface may be the same or different so long as at least one of the surfaces comprises a surface of PMMA polymer.

In this disclosure, a number of terms and abbreviations are used. The following definitions apply unless specifically stated otherwise.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

The term "comprising" means the presence of the stated features, integers, steps, or components as referred to in the claims, but does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the terms "polypeptide" and "peptide" will be used interchangeably to refer to a polymer of two or more amino acids joined together by a peptide bond. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics. In one embodiment, the peptides are comprised of L-amino acids.

As used herein, the term "polymethyl methacrylate" polymer is abbreviated as "PMMA" and is synonymous with methyl 2-methylpropanoate, poly(methyl methacrylate) and all other synonyms used under CAS#9011-14-7.

As used herein, "PBP" means a PMMA-binding peptide. As used herein, the term "PMMA-binding peptide" refers to peptides that bind with strong affinity to the surface of a PMMA polymer or copolymer comprising PMMA. In one embodiment, the PMMA-binding peptide binds to PMMA polymer. For purposes of the present discussion PMMA-binding peptides have classed into various Groups ranging from Group A to H, based on specific differentiating amino acid motifs within each group. The present application relates to Group A PMMA-binding peptides.

As used herein, the term "peptide finger" will be used to refer to an individual target surface-binding peptide, typically identified by biopanning against a target surface. Peptides having affinity for PMMA by biopanning may be referred to as "PMMA-binding peptides" or peptide "fingers".

As used herein, the term "peptide hand" will be used to refer to a binding domain or region comprising 2 or more "peptide fingers" coupled together using one or more optional, independently-selected linkers, wherein the inclusion of at least one peptide linker is preferred.

As used herein, the terms "PMMA hand" and "PMMA-binding domain" will refer to a single chain peptide comprising of at least two PMMA-binding peptides linked together by an optional molecular linker (L) ("linker") or spacer, wherein the inclusion of a molecular linker is preferred. In one embodiment, the molecular linker is a peptide linker. In another embodiment, the peptide linker ranges in length from 1 to 50 amino acids, preferably 3 to 25 amino acids in length, and may be comprised of various amino acids. In another embodiment, the molecular linker may be comprised of one or more of the amino acids selected from the group consisting of proline, lysine, glycine, alanine, glutamic acid, serine, and combinations thereof.

As used herein, the term "peptide-based reagent" or "peptide reagent" refers to a single chain peptide comprising at least one of the present PMMA-binding peptides having an amino acid sequence (SEQ ID NO: 21). In one embodiment, the peptide reagent comprises at least one of the present PMMA-binding peptides having an amino acid sequence selected from the group consisting of SEQ ID NOs: 19, 20, and 21. In another embodiment, the peptide reagent comprises at least one PMMA-binding peptides having an amino acid sequence selected from the group consisting of SEQ ID NOs: 19 and 20.

In another embodiment, the peptide-based reagent comprises two or more of the present PMMA-binding peptides separated by a molecular linker. The peptide-based reagent may also have at least one region that can be coupled to the benefit agent and/or a region that provides a binding affinity for a second target surface. As such, the peptide-based reagent may used as an interfacial material to couple a benefit agent or an additional target surface (via a target surface-binding domain or "TBD") to a surface comprised of PMMA polymer. The benefit agent-binding region may be comprised of at least benefit agent-binding peptide. The benefit agent may be coupled covalently or non-covalently to the present peptide-based reagents. In one embodiment, the benefit agent is couple non-covalently to the peptide reagent. In another embodiment, the benefit agent is coupled to the peptide-based reagent covalently.

As used herein, the terms "coupling" and "coupled" refer to any chemical association and may include both covalent and non-covalent interactions. In one embodiment, the coupling is non-covalent. In another embodiment, the coupling is covalent.

As used herein, the term "bridge", "peptide bridge", and "bridging element" will refer to a linear peptide used to join a PMMA-binding domain ("PMMA-binding hand" or the "first domain") to a peptide domain (the "second domain") capable of binding to the surface of particulate benefit agent (i.e., covalent or non-covalent coupling) or a second target surface via a target surface-binding domain (TBD). The peptide bridge may range in size from 1 to 60 amino acids in length, preferably 6 to 30 amino acids in length. Examples of peptide bridges are provided as SEQ ID NOs: 255-256.

The term "benefit agent' is abbreviated as "BA" and is a general term applying to a compound or substance that may be coupled to a surface comprising PMMA polymer using one of the present PMMA-binding peptides or peptide-based reagents in order to provide a desirable characteristic of the benefit agent to the complex. In the most general sense a benefit agent may be any element, molecule or compound that is not PMMA. In one embodiment, the benefit agent may be one or more of the PMMA-binding peptides. Benefit agents typically include, but are not limited to, colorants such as pigments and dyes as well as pharmaceuticals, markers, conditioners, fragrances, as well as domains having a defined activity ("active domains" or "AD") such as enzyme catalysts, and antimicrobial agents, such as antimicrobial peptides.

The term "target binding domain" is abbreviated as "TBD" will refer to a portion or region of the peptide-based reagent having affinity for a target surface. In one embodiment, the TBD has strong affinity for a target surface. In another embodiment, the present peptide-based reagents will comprise at least one region or domain having strong affinity for a surface comprising PMMA, wherein the domain having affinity for PMMA will be comprises of at least one of the present PMMA-binding peptides; and at least one second region or domain having strong affinity for a benefit agent or another target surface including, but not limited to, body surfaces such as hair, skin, nails, teeth, gums, and corneal tissue, as well as other surfaces such as pigments, synthetic polymers, peptides, nucleic acids, conditioning agents, print media, clay, calcium carbonate, silica, and other particulate benefit agents, such as microspheres. In one embodiment, the target binding domain (TBD) is a body surface-binding domain selected from the group consisting of a hair-binding domain, a skin-binding domain, a nail-binding domain, a tooth-binding domain (both tooth pellicle-binding peptides and/or tooth enamel-binding peptides), and domains having affinity for other body surfaces, such as the gums or corneal tissue. Examples of various peptides having affinity various benefit agent surfaces are provided in the present sequence descriptions and the accompanying sequence listing.

The term "body surface" will mean any surface of the human body that may serve as a substrate for the binding of a peptide carrying a benefit agent. Typical body surfaces may include, but are not limited to, hair, skin, nails, teeth (enamel and/or pellicle surfaces), gums, and corneal tissue. In one embodiment, the body surface is selected from the group consisting of hair, skin, nail, tooth enamel, and tooth pellicle.

As used herein, "BSBP" means body surface-binding peptide. A body surface-binding peptide is a peptide having strong affinity for a specified body surface. A body surface-binding peptide is a peptide ranging in size from 7 to 60 amino acids in length that binds with strong affinity to at least one body surface. As used herein, the body surface-binding peptide is selected from the group consisting of hair-binding peptides, skin-binding peptides, nail-binding peptides, and oral cavity surface-binding peptides, such as a tooth enamel-binding peptides and tooth pellicle-binding peptides. In a preferred embodiment, the body surface-binding peptide is selected from the group consisting of a hair-binding peptide, a skin-binding peptide, a nail-binding peptide, and a tooth-binding peptide (enamel or pellicle). Examples of body surface-binding peptides are provided as SEQ ID NOs: 258-474.

As used herein, the term "hair" as used herein refers to human hair, eyebrows, and eyelashes. The term "hair surface" will mean the surface of human hair capable of binding to a hair-binding peptide. As used herein, the term "hair-binding peptide" refers to a peptide that binds with high affinity to hair. Examples of hair-binding peptides are described in U.S. Patent Application Publication NOs. 2005-0226839; 2007-0065387; 2007-0110686; 2007-0196305; U.S. patent application Ser. Nos. 11/877,692 and 11/939,583; U.S. Pat. No. 7,220,405; and published PCT Application No. WO2004/048399. Examples of hair-binding peptides are provided as SEQ ID NOs: 258-384.

The term "skin", as used herein, refers to human skin, or pig skin, VITRO-SKIN® and EPIDERM™ which are substitutes for human skin. Skin will generally comprise a layer of epithelial cells and may additionally comprise a layer of endothelial cells. Examples of skin-binding peptides are described in U.S. Patent Application Publication NOs. 2005-0249682; US 2006-0199206; 2007-0065387; and 2007-0110686; U.S. patent application Ser. No. 11/877,692; and published PCT Application NO. WO2004/048399.

As used herein, the term "skin-binding peptide" refers to peptides that bind with strong affinity to skin. Examples of skin-binding peptides have also been reported (U.S. Patent Application Publication NOs. 2007-0274931 and 2007-0249805, and published PCT Patent Application WO 2004/000257). The skin-binding peptides may be linked together to form skin-binding domains ("hands"). Examples of skin-binding peptides are provided as SEQ ID NOs: 380-432.

As used herein, the term "nails" as used herein refers to human fingernails and toenails. As used herein, the term "nail-binding peptide" refers to peptides that bind with strong affinity to nails. Examples of nail-binding peptides are provided as SEQ ID NOs: 433-434. The nail-binding fingers may be linked together to form nail-binding domains ("hands").

As used herein, the term "oral cavity surface-binding peptide" refers to peptides that bind with strong affinity to teeth, gums, cheeks, tongue, or other surfaces in the oral cavity. As used herein, the term "tooth-binding peptide" will refer to a peptide that binds with high affinity to tooth enamel or tooth pellicle. Examples of tooth-binding peptides are disclosed in co-pending U.S. Patent Application Publication NO. 2008-0280810 and are provided as SEQ ID NOs: 435-474. The tooth-binding fingers may be linked together to form tooth-binding domains ("hands"). In one embodiment, the oral cavity surface-binding peptide is a peptide that binds with high affinity to a tooth surface.

The term "tooth surface" will refer to a surface comprised of tooth enamel (typically exposed after professional cleaning or polishing) or tooth pellicle (an acquired surface comprising salivary proteins). Hydroxyapatite can be coated with salivary glycoproteins to mimic a natural tooth pellicle surface (tooth enamel is predominantly comprised of hydroxyapatite).

As used herein, the terms "pellicle" and "tooth pellicle" will refer to the thin film (typically ranging from about 1 μm to about 200 μm thick) derived from salivary glycoproteins which forms over the surface of the tooth crown. Daily tooth brushing tends to only remove a portion of the pellicle surface while abrasive tooth cleaning and/or polishing (typically by a dental professional) will expose more of the tooth enamel surface.

As used herein, the terms "enamel" and "tooth enamel" will refer to the highly mineralized tissue which forms the outer layer of the tooth. The enamel layer is composed primarily of crystalline calcium phosphate (i.e., hydroxyapatite) along with water and some organic material. In one embodiment, the tooth surface is selected from the group consisting of tooth enamel and tooth pellicle.

As used herein, the term "pigment" means an insoluble colorant. A wide variety of organic and inorganic pigments alone or in combination may be used. In one embodiment, the pigment is a metal oxide. As used herein, the term "pigment lake" or "lake" refers to a pigment manufactured by precipitating a dye with an inert binder, usually a metallic salt.

As used herein, "Pigment-BP" means pigment-binding peptide. A pigment-binding peptide is a peptide that binds with strong affinity to a specified pigment. Pigment-binding peptides have been reported in the art (U.S. Patent Application Publ. No. 2005-0054752, U.S. Pat. No. 7,285,264, and co-pending U.S. patent application Ser. No. 12/632,827). Examples of pigment-binding peptides are provided as SEQ ID NOs: 105-159. Examples of iron oxide-based pigment binding peptides are provided as SEQ ID NOs: 131-159 (U.S. patent application Ser. No. 12/632,827).

As used herein, a "polymer" is a natural or synthetic compound of usually high molecular weight consisting of repeated linked units. As used herein, "Poly-BP" means polymer-binding peptide (excluding the PMMA-binding peptides (SEQ ID NOs: 1-35)). Examples of peptides that bind with high affinity to a specified polymer have been described (U.S. Patent Application Publication No. 2008-0206809). Examples of polymer-binding peptides may include peptides that bind to (previously reported) polymethyl methacrylate (SEQ ID NOs: 42-68), polypropylene (SEQ ID NOs: 69-75), polytetrafluoroethylene (SEQ ID NOs: 76-84), polyethylene (85-91), nylon (SEQ ID NOs: 92-97), and polystyrene (SEQ ID NOs: 98-100).

Additional peptides having strong affinity for their respective surfaces also include, but are not limited to, cellulose acetate-binding peptides (SEQ ID NOs: 101-104); silica-binding peptides (U.S. patent application Ser. No. 12/632,829 and SEQ ID NOs: 201-223); clay-binding peptides (U.S. Patent Application Publication No. 2007-0249805 and SEQ ID NOs: 160-174); and calcium carbonate-binding peptides (U.S. Patent Application Publication No. 2009-0029902 and SEQ ID NOs: 175-200).

As used herein, an "antimicrobial peptide" is a peptide having the ability to kill microbial cell populations (see U.S. Pat. No. 7,427,656). Examples of antimicrobial peptides are provided as SEQ ID NOs: 224-252.

As used herein, the term "operably-linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). In a further embodiment, the definition of "operably linked" may also be extended to describe the products of chimeric genes.

As used herein, the term "$MB_{50}$" refers to the concentration of the binding peptide that gives a signal that is 50% of the maximum signal obtained in an ELISA-based binding assay (see Example 9 of U.S. Published Patent Application No. 2005-0226839; hereby incorporated by reference). The $MB_{50}$ provides an indication of the strength of the binding interaction or affinity of the components of the complex. The lower the value of $MB_{50}$, the stronger the interaction of the peptide with its corresponding substrate.

As used herein, the terms "binding affinity" and "affinity" refer to the strength of the interaction of a binding peptide (e.g., target surface-binding peptides, target surface-binding domains, and peptide-based reagents) with its respective substrate. The binding affinity may be reported in terms of the $MB_{50}$ value as determined in an ELISA-based binding assay or as a $K_D$ (equilibrium dissociation constant) value, which may be deduced using a methodology such as surface plasmon resonance (SPR).

As used herein, the term "strong affinity" refers to a binding affinity, as measured as an $MB_{50}$ value of $K_D$ value, of $10^{-4}$ M or less, preferably less than $10^{-5}$ M, more preferably less than $10^{-6}$ M, more preferably less than $10^{-7}$ M, even more preferably less than $10^{-8}$ M, and most preferably less than $10^{-9}$ M.

As used herein, "L" means "molecular linker" or "linker". The linker may be a peptide or non-peptide-based molecular linker. In one embodiment, the linker is a peptide linker. Peptide linkers separating a PMMA-binding domain from a benefit agent, a benefit agent-binding domain or a target surface-binding domain (TBD) may also be referred to as a peptide "bridge" or "bridging element". In one embodiment, the peptide linker is 1 to 60 amino acids in length, preferably 3 to 25 amino acids in length. Examples of peptide linkers are provided as SEQ ID NOs: 253-254.

In one embodiment, the benefit agent may be an active domain within (i.e., a subsequence of the peptide reagent) or coupled to the peptide reagent. In one embodiment, the active domain is a portion of the peptide reagent that is not responsible for PMMA binding but provides additional functionality or benefit. In another embodiment the active domain may have antimicrobial functionality. For example, the peptide reagent may be comprised of at least one of the present PMMA-binding peptides and at least one antimicrobial peptide; whereby coupling of said peptide reagent to a surface comprising PMMA polymer (such as PLEXIGLAS™) provides a surface characterized by an enhancement in antimicrobial activity.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |

-continued

| Amino Acid | Three-Letter Abbreviation | One-Letter Abbreviation |
|---|---|---|
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Miscellaneous (or as defined herein) | Xaa | X |

Binding Affinity

The present PMMA-binding peptides exhibit a strong affinity for a surface comprising PMMA polymer based on their ability to bind to a PMMA polymer after many rounds of selection under stringent selection conditions. The affinity of the peptide for PMMA can be expressed in terms of the dissociation constant $K_D$ or an ELISA-based $MB_{50}$ value. $K_D$ (expressed as molar concentration) corresponds to the concentration of peptide at which the binding site on the target is half occupied, i.e. when the concentration of target with peptide bound (bound target material) equals the concentration of target with no peptide bound. The smaller the dissociation constant, the more tightly bound the peptide is; for example, a peptide with a nanomolar (nM) dissociation constant binds more tightly than a peptide with a micromolar (µM) dissociation constant. In one embodiment, the present PMMA-binding peptides have a $K_D$ value of $10^{-4}$ M or less, preferably $10^{-5}$ M or less, more preferably $10^{-6}$ M or less, even more preferably $10^{-7}$ M or less, yet even more preferably $10^{-8}$ M or less, and most preferably $10^{-9}$ M or less.

Alternatively, one of skill in the art can also use an ELISA-based assay to calculate a relative affinity of the peptide for the target material (reported as an $MB_{50}$ value; see present Example 3 and co-owned U.S. Patent Application Publication No. 2005-022683, herein incorporated by reference). As used herein, the term "$MB_{50}$" refers to the concentration of the binding peptide that gives a signal that is 50% of the maximum signal obtained in an ELISA-based binding assay. The $MB_{50}$ value provides an indication of the strength of the binding interaction or affinity of the components of the complex. The lower the value of $MB_{50}$, the stronger the interaction of the peptide with its corresponding substrate. In one embodiment, the $MB_{50}$ value (reported in terms of molar concentration) for the PMMA-binding peptide is $10^{-4}$ M or less, preferably $10^{-5}$ M or less, more preferably $10^{-6}$ M or less, more preferably $10^{-7}$ M or less, and most preferably $10^{-8}$ M or less.

mRNA-Display

The present PMMA-binding peptides were biopanned against a PMMA polymer using mRNA display, an in vitro panning method commonly used for identifying peptides having an affinity for a target material (U.S. Pat. No. 6,258,558). Briefly, a random library of DNA molecules was generated wherein they encode a peptide of a desired length. The length of the peptide within the display library may be to be up to 200 amino acids in length and is typically designed to range from about 7 to about 100 amino acids in length. In one embodiment, the library of peptides may be designed to be about 7 to about 60 amino acids in length, preferably about 7 to about 30 amino acids in length, more preferably about 15 to about 30 amino acids in length, and most preferably about 27 amino acids in length (i.e., a "27-mer" library). Typically, the nucleic acid molecule encoding the peptide includes (in addition to the coding region) appropriate 5' and 3' regulatory regions necessary for efficient in vitro transcription and translation. The design of the nucleic acid constructs used for preparing the mRNA-display library is well known to one of skill in the (see WO2005/051985). The nucleic acid molecules can be designed to optionally encode flexible linkers, cleavage sequences, fusion promoting sequences, and identification/purification tags (e.g., poly-A regions, His tags, etc.) to facility purification and/or processing in subsequence steps.

The library of random nucleic acid fragments is transcribed in vitro to produce an mRNA library. The mRNA is isolated and subsequently fused to a linker molecule (i.e., a puromycin-oligonucleotide linker or a puromycin derivative-oligonucleotide linker) using techniques well-known in the art (U.S. Pat. Nos. 6,258,558; 6,228,994; and Kurz et al., (2000) NAR, 28(18):e83 i-v). In a preferred embodiment, the puromycin-oligonucleotide linker comprises psoralen for rapid and facile preparation of the mRNA-protein fusions (Kurtz et al., supra). The mRNA-puromycin fusion molecules are then translated in vitro whereby the nascent polypeptide is fused (via the puromycin-oligonucleotide linker) to the mRNA (PROFUSION™ molecules; Adnexus Therapeutics, Weltham, Mass.). In this way, the phenotype (peptide) is linked to the corresponding genotype (RNA).

The mRNA-peptide fusion molecules are typically reverse transcribed into a DNA/mRNA-protein fusion molecules prior to affinity selection. The library (often comprising up to $10^{13}$ different sequences) is contacted with target ligand/material (typically an immobilized target and/or a solid surface). The selection process is carried out in an aqueous medium wherein parameters such as time, temperature, pH, buffer, salt concentration, and detergent concentration may be varied according the stringency of the selection strategy employed. Typically, the temperature of the incubation period ranges from 0° C. to about 40° C. and the incubation time ranges from about 1 to about 24 hours.

Several washing steps are typically used to remove the non-binding/low affinity fusion molecules. The stringency of the washing conditions may be adjusted to select those fusion molecules having the highest affinity for the target material. The high affinity fusion molecules are isolated and then PCR-amplified in order to obtain the nucleic acid sequences encoding the binding peptides. The mRNA-display selection cycle is typically repeated for 3 to 10 cycles in order to select/enrich those fusion molecules comprising peptide sequences exhibiting the highest affinity for the target material.

Error-prone PCR may optionally be incorporated into mRNA-display selection process whereby mutants derived from a previously selected high affinity sequence are used. The process is typically repeated for several cycles in order to obtain the peptides having improved affinity for the target material.

Optionally, any PMMA-binding peptide sequence identified using mRNA-display may be verified using the free peptide. Typically, the nucleic acid molecule encoding the PMMA-binding peptide is cloned and recombinantly expressed in an appropriate microbial host cell, such as *E. coli*. The free peptide is then isolated and assayed against the targeted material to validate the binding affinity of the peptide sequence.

Polymethyl Methacrylate

PMMA polymer is prepared by the polymerization of the monomer methyl methacrylate, which is available from many commercial suppliers, such as Aldrich (Milwaukee, Wis.), ICI Acrylics (Beaumont, Tex.), CYRO Industries (Rockaway, N.J.), Total Specialty Chemicals, Inc (New Canaan, Conn.), and Degussa Corp. (Parsippani, N.J.). Methyl methacrylate may be polymerized using methods known in the art, such as radical polymerization, anionic polymerization, or group transfer polymerization (*Ullmann's Encyclopedia of Industrial Chemistry*, 6$^{th}$ edition, 2003, Wiley-VCH Verlag GmbH and Co., Weinheim, Germany, Vol. 28, pp. 377-389). For example, radical polymerization may be carried out homogeneously (i.e., bulk or solution polymerization) or heterogeneously (i.e., suspension or emulsion polymerization). The radical polymerization may be initiated using radiation, heat, or chemical initiators, such as azo compounds or organic peroxy compounds. Copolymers may be produced by these methods using a mixture of the desired monomers.

The PMMA polymer may be produced in various shapes or forms, such as beads, microspheres, sheets, rods, tubes, films, plates, rings, fiber, and microfilament, using injection molding, extrusion, and casting techniques, which are well known in the art. Additionally, PMMA in various shapes is available commercially from companies such as CRYO Industries and Bang Laboratories (Fishers, Ind.).

In one embodiment, the PMMA polymer or a copolymer prepared using PMMA is coated onto another surface, such as metal, metal oxide, polymer, pigment, glass, cloth, and the like, using methods known in the art, such as spraying, brushing, dip coating and casting.

In another embodiment, the PMMA polymer or copolymer is imbedded into the surface of another material, such as another polymer. This may be done by adding particles, beads, or fragments of PMMA material into the other polymer as it cures.

In another embodiment, a PMMA copolymer is used as a dispersant for pigments or other insoluble particles, including metallic and semiconductor nanoparticles. The copolymer may be a random copolymer or a structured copolymer (i.e., a non-random block copolymer). Preferred random dispersants may include methyl methacrylate copolymers with other acrylates or styrene. Most preferred are structured polymer dispersants, which include AB, BAB and ABC block copolymers, branched polymers and graft polymers. Preferably these copolymers comprise methyl methacrylate with one or more monomers such as acrylate, methacrylate, butyl methacrylate, 2-ethylhexyl methacrylate, benzylmethacrylate, phenoxyethyl acrylate, and ethoxytriethyleneglycolmethacrylate, such as those described by Nigan (U.S. Patent Application Publication No. 2004-0232377). Some useful structured polymer dispersants are disclosed in U.S. Pat. No. 5,085,698, EP-A-0556649, and U.S. Pat. No. 5,231,131.

Production of Peptides

The present peptides may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services.

Alternatively, the present peptides may be prepared using recombinant DNA and molecular cloning techniques. Genes encoding the present peptides may be produced in heterologous host cells, particularly in the cells of microbial hosts, as described by Huang et al. (U.S. Patent Application Publication No. 2005-0050656).

Preferred heterologous host cells for expression of the present peptides are microbial hosts that can be found broadly within the fungal or bacterial families and which grow over a wide range of temperature, pH values, and solvent tolerances. Because transcription, translation, and the protein biosynthetic apparatus are the same irrespective of the cellular feedstock, functional genes are expressed irrespective of carbon feedstock used to generate cellular biomass. Examples of host strains include, but are not limited to, bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, bacterial host strains include *Escherichia, Bacillus*, and *Pseudomonas*. In a preferred embodiment, the bacterial host cell is *Escherichia coli*.

Benefit Agents

Benefit agents are any material or substance that may be complexed with the peptide-based reagent comprising one or more of the present PMMA-binding peptides in an manner so as to deliver a benefit at the point where the peptide reagent is attached. A benefit agent may be selected for the purpose of adding the physical, chemical and/or biological properties of said agent to the PMMA polymer surface.

Benefit agents may be inorganic or organic in nature. Some preferred embodiments include benefit agents that are pigments, conditioners, colorants, antimicrobial agents, and fragrances.

Conditioners

In one embodiment, a peptide-based reagent may be used that provides a conditioning effect to a body surface. For example, a peptide reagent may be designed to couple a target surface, such as a body surface, with a conditioning agent comprising a surface of PMMA polymer. The conditioning agent may be provided or incorporated with a bead, particle, or microsphere comprising a PMMA polymer or copolymer surface. Conditioner benefits agents as referred to in discussion of the present invention generally mean benefit agents that provide an improvement to the appearance, texture or quality of the substance they are designed to condition. Conditioner benefit agents may be used with the present invention to condition any substance including but not limited to hair, skin, nail, tooth enamel, tooth pellicle, gums, others tissues of the oral cavity, leather, and upholstery. In the preferred embodiment the present invention is used in combination with a benefit agent that provides a conditioning effect to hair, skin, nails, tooth enamel, and tooth pellicle.

Hair conditioning agents are well known in the art, see for example Green et al. (WO 01/07009) and are available commercially from various sources. Suitable examples of hair conditioning agents include, but are not limited to cationic polymers, such as cationized guar gum, diallyl quaternary ammonium salt/acrylamide copolymers, quaternized polyvinylpyrrolidone and derivatives thereof, and various polyquaternium-compounds; cationic surfactants, such as stearalkonium chloride, centrimonium chloride, and Sapamin hydrochloride; fatty alcohols, such as behenyl alcohol; fatty amines, such as stearyl amine; waxes; esters; nonionic polymers, such as polyvinylpyrrolidone, polyvinyl alcohol, and polyethylene glycol; silicones; siloxanes, such as decamethylcyclopentasiloxane; polymer emulsions, such as amodimethicone; and volumizing agents, such as nanoparticles (e.g., silica nanoparticles and polymer nanoparticles). The preferred hair conditioning agents contain amine or hydroxyl functional groups to facilitate coupling to the hair-binding peptides. Examples of conditioning agents are octylamine (CAS No. 111-86-4), stearyl amine (CAS No. 124-30-1), behenyl alcohol (CAS No. 661-19-8, Cognis Corp., Cincinnati, Ohio), vinyl group terminated siloxanes, vinyl group terminated silicone (CAS No. 68083-19-2), vinyl group terminated methyl vinyl siloxanes, vinyl group terminated methyl vinyl silicone (CAS No. 68951-99-5), hydroxyl terminated siloxanes, hydroxyl terminated silicone (CAS No. 80801-30-5), amino-modified silicone derivatives, [(aminoethyl)amino]propyl hydroxyl dimethyl siloxanes, [(aminoethyl)amino]propyl hydroxyl dimethyl silicones, and alpha-tridecyl-omega-hydroxy-poly(oxy-1,2-ethanediyl) (CAS No. 24938-91-8).

If the present peptide-based reagents are to be used in connection with a hair care composition, such as when the target binding domain (TBD) of the peptide reagent has affinity for hair, an effective amount of the peptide reagent (alone or in a complex with a PMMA-coated benefit agent) for use in a hair care composition is herein defined as a proportion of from about 0.01% to about 10%, preferably about 0.01% to about 5% by weight relative to the total weight of the composition. Components of a cosmetically acceptable medium for hair care compositions are described by Philippe et al. in U.S. Pat. No. 6,280,747, and by Omura et al. in U.S. Pat. No. 6,139,851 and Cannell et al. in U.S. Pat. No. 6,013,250, each of which is incorporated herein by reference. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hare care compositions may contain one or more conventional cosmetic or dermatological additives or adjuvants including but not limited to, antioxidants, preserving agents, fillers, surfactants, UVA and/or UVB sunscreens, fragrances, thickeners, wetting agents and anionic, nonionic or amphoteric polymers, and dyes or pigments.

Skin conditioning agents may include, but are not limited to, astringents, which tighten skin; exfoliants, which remove dead skin cells; emollients, which help maintain a smooth, soft, pliable appearance; humectants, which increase the water content of the top layer of skin; occlusives, which retard evaporation of water from the skin's surface; and miscellaneous compounds that enhance the appearance of dry or damaged skin or reduce flaking and restore suppleness. Particles comprising PMMA and a skin conditioning agent may be in conjunction with one of the present peptide-based reagents to couple the condition agent to skin (assuming the peptide reagent also comprises a portion having affinity for skin). Skin conditioning agents are well known in the art, see for example Green et al., supra, and are available commercially from various sources. Suitable examples of skin conditioning agents include, but are not limited to alpha-hydroxy acids, beta-hydroxy acids, polyols, hyaluronic acid, D,L-panthenol, polysalicylates, vitamin A palmitate, vitamin E acetate, glycerin, sorbitol, silicones, silicone derivatives, lanolin, natural oils and triglyceride esters. The skin conditioning agents may also include polysalicylates, propylene glycol (CAS No. 57-55-6, Dow Chemical, Midland, Mich.), glycerin (CAS No. 56-81-5, Proctor & Gamble Co., Cincinnati, Ohio), glycolic acid (CAS No. 79-14-1, DuPont Co., Wilmington, Del.), lactic acid (CAS No. 50-21-5, Alfa Aesar, Ward Hill, Mass.), malic acid (CAS No. 617-48-1, Alfa Aesar), citric acid (CAS No. 77-92-9, Alfa Aesar), tartaric acid (CAS NO. 133-37-9, Alfa Aesar), glucaric acid (CAS No. 87-73-0), galactaric acid (CAS No. 526-99-8), 3-hydroxyvaleric acid (CAS No. 10237-77-1), salicylic acid (CAS No. 69-72-7, Alfa Aesar), and 1,3 propanediol (CAS No. 504-63-2, DuPont Co., Wilmington, Del.). Polysalicylates may be prepared by the method described by White et al. in U.S. Pat. No. 4,855,483, incorporated herein by reference. Glucaric acid may be synthesized using the method described by Merbouh et al. (*Carbohydr. Res.*, (2001) 336:75-78). The 3-hydroxyvaleric acid may be prepared as described by Bramucci et al. in U.S. Pat. No. 6,562,603.

In a number of embodiments the present peptide reagents could be used in a skin care composition (for example, when the peptide reagent comprises a skin-binding domain and a PMMA polymer binding domain, wherein the benefit agent comprise PMMA polymer, such as a bead or surface coating). Skin care compositions are herein defined as compositions comprising an effective amount of a skin conditioner or a mixture of different skin conditioners in a cosmetically acceptable medium. The uses of these compositions include, but are not limited to, skin care, skin cleansing, make-up, and anti-wrinkle products. If the present invention is desired to be used in connection with a skin care composition an effective amount of the complex for skin care compositions is herein defined as a proportion of from about 0.001% to about 10%, preferably about 0.01% to about 5% by weight relative to the total weight of the composition. This proportion may vary as a function of the type of skin care composition. Suitable compositions for a cosmetically acceptable medium are described by Philippe et al., supra. For example, the cosmetically acceptable medium may be an anhydrous composition containing a fatty substance in a proportion generally of from about 10 to about 90% by weight relative to the total weight of the composition, where the fatty phase containing at least one liquid, solid or semi-solid fatty substance. The fatty substance includes, but is not limited to, oils, waxes, gums, and socalled pasty fatty substances. Alternatively, the compositions may be in the form of a stable dispersion such as a water-in-oil or oil-in-water emulsion. Additionally, the compositions may contain one or more conventional cosmetic or dermatological additives or adjuvants, including but not limited to, antioxidants, preserving agents, fillers, surfactants, UVA and/or UVB sunscreens, fragrances, thickeners, wetting agents and anionic, nonionic or amphoteric polymers, and dyes or pigments.

Colorants.

The term colorant generally refers to a coloring agent. Colorants may be chemically organic or inorganic and may include pigments, lakes or dyes. The colorants may be prepared by covalently attaching at least one of the present PMMA-binding peptides to a coloring agent, either directly or via a linker, using any of the coupling methods known in the art (see for example, U.S. Patent Application Publication No. 2005-0226839).

Pigments are a particularly suitable benefit agent. A wide variety of organic and inorganic pigments alone or in combination may be used. Preferred organic pigments are carbon black, such as Carbon Black FW18, and colored pigments such as CROMOPHTAL® Yellow 131AK (Ciba Specialty Chemicals), SUNFAST® Magenta 122 (Sun Chemical) and SUNFAST® Blue 15:3 (Sun Chemical). Examples of inorganic pigments may include, but are not limited to finely divided metals such as copper, iron, aluminum, and alloys thereof; and metal oxides, such as silica, alumina, and titania. Additional examples of suitable pigments are given by Ma et al. in U.S. Pat. No. 5,085,698, incorporated herein by reference.

Suitable coloring agents that may be used with the present PMMA-binding peptides and/or peptide-based reagents may include, but are not limited to 4-hydroxypropylamino-3-nitrophenol, 4-amino-3-nitrophenol, 2-amino-6-chloro-4-nitrophenol, 2-nitro-paraphenylenediamine, N,N-hydroxyethyl-2-nitro-phenylenediamine, 4-nitro-indole, Henna, HC Blue 1, HC Blue 2, HC Yellow 4, HC Red 3, HC Red 5, Disperse Violet 4, Disperse Black 9, HC Blue 7, HC Blue 12, HC Yellow 2, HC Yellow 6, HC Yellow 8, HC Yellow 12, HC Brown 2, D&C Yellow 1, D&C Yellow 3, D&C Blue 1, Disperse Blue 3, Disperse violet 1, eosin derivatives such as D&C Red No. 21 and halogenated fluorescein derivatives such as D&C Red No. 27, D&C Red Orange No. 5 in combination with D&C Red No. 21 and D&C Orange No. 10; and pigments, such as D&C Red No. 36 and D&C Orange No. 17, the calcium lakes of D&C Red Nos. 7, 11, 31 and 34, the barium lake of D&C Red No. 12, the strontium lake of D&C Red No. 13, the aluminum lakes of FD&C Yellow No. 5, of FD&C Yellow No. 6, of D&C Red No. 27, of D&C Red No. 21, and of FD&C Blue No. 1, iron oxides, manganese violet, chromium oxide, titanium dioxide, zinc oxide, barium oxide, ultramarine blue, bismuth citrate, and carbon black particles.

Fragrances.

The PMMA-binding peptides and/or peptide-based reagents may be used to delivery or couple a fragrance to a surface comprising PMMA. In another embodiment, a particle, bead, or microsphere comprising PMMA may also be used to delivery a fragrance to a target surface, such as a body surface, provided that the peptide reagent comprises an appropriate target binding domain (TBD), such as a body surface-binding domain.

A fragrance is a complex, compound or element that releases, a substance which may be perceived by the sense of olfaction or chemical detection in any organism, but preferably, in humans. The object sensed or detected may be a part of or the whole of the fragrance benefit agent. In the preferred embodiment the odor is perceived as desirable to humans. However, some uses may combine with a fragrance benefit agent that is repellent to a class of organisms, including a class that contains or is humans. Any known fragrance or odor may be use as a benefit agent. It may be desirable to attach a fragrance benefit agent to the PMMA-peptide complex by a bond structure or linking molecule that allows the benefit agent to be released, in part or in whole, so that it may be perceived by a sensing organ or chemical detector.

Numerous fragrances, both natural and synthetic, are well known in the art. For example, Secondini (*Handbook of Perfumes and Flavors*, Chemical Publishing Co., Inc., New York, 1990) describes many of the natural and synthetic fragrances used in cosmetics. Suitable natural fragrances may include, but are not limited to jasmine, narcissus, rose, violet, lavender, mint, spice, vanilla, anise, amber, orange, pine, lemon, wintergreen, rosemary, basil, and spruce. Suitable synthetic fragrances may include, but are no limited to, acetaldehyde, C7 to C16 alcohols, benzyl acetate, butyric acid, citric acid, isobutyl phenyl acetate, linalyl butyrate, malic acid, menthol, phenyl ethyl cinnamate, phenyl propyl formate, tannic acid, terpineol, vanillin, amyl salicylate, benzaldehyde, diphenyl ketone, indole, and the like.

Single Chain Peptide-Based Reagents for Coupling a Benefit Agent to PMMA

The present peptide reagents comprising at least one of the present PMMA-binding peptides may be used in a composition to couple a benefit agent to surface, film, sheet, particle, bead, or microsphere comprising a surface having PMMA polymer. In a further embodiment, peptide reagent comprising a target binding domain (TBD) having affinity for a target surface, such as a body surface, may be used to couple a benefit agent comprising PMMA polymer to the target surface (i.e., the benefit agent comprises a surface of PMMA polymer capable of binding to the peptide reagent).

In one embodiment, the peptide reagents may contain one or more molecular linkers (L) separating the individual PMMA-binding peptides and/or separating the PMMA-binding peptide(s) or peptide-based reagent from the benefit agent or target binding domain (TBD).

As such, a peptide-based reagent is provided comprising the general structure:

$([PBP]_n\text{-}[L]_x\text{-}BA\text{-}[L]_y)_m$; or $([PBP]_n\text{-}[L]_x\text{-}TBD\text{-}[L]_y)_m$ wherein:
i) PBP is a polymethyl methacrylate-binding peptide;
ii) L is a linker molecule;
iii) BA is at least one benefit agent;
iv) TBD is a target binding domain;
v) x and y independently range from 0 to 10;
vi) n=1 to 10; and
vii) m=1 to 10;
wherein the polymethyl methacrylate-binding peptide comprises amino acid sequence SEQ ID NO: 21.

It may also be desirable to have multiple binding peptides coupled to the benefit agent to enhance the interaction between the peptide reagent and the surface comprising PMMA polymer. Either multiple copies of the same binding peptide or a combination of different binding peptides may be used. In the case of large particles, a large number of binding peptides, such as up to about 1,000 peptides, may be coupled to the particle. A smaller number of binding peptides can be coupled to smaller molecules, i.e., up to about 50.

Linker Molecules

Linker molecules may optionally be used with one or more of the embodiments described herein. The linker may be any of a variety of molecules, such as alkyl chains, phenyl compounds, ethylene glycol, amides, esters and the like. Preferred linkers are hydrophilic and have a chain length from 1 to about 100 atoms, more preferably, from 2 to about 30 atoms. Examples of preferred linkers include, but are not limited to, ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, and ethyl, propyl, hexyl, steryl, cetyl, and palmitoyl alkyl chains. The linker may be covalently attached to the peptide and the benefit agent using any of the coupling chemistries described above. In order to facilitate incorporation of the linker, a bifunctional cross-linking agent that contains a linker and reactive groups at both ends for coupling to the peptide and the benefit agent may be used. Suitable bifunctional cross-linking agents are well known in the art and may include diamines, such as 1,6-diaminohexane; dialdehydes, such as glutaraldehyde; bis N-hydroxysuccinimide esters, such as ethylene glycol-bis (succinic acid N-hydroxysuccinimide ester), disuccinimidyl glutarate, disuccinimidyl suberate, and ethylene glycol-bis (succinimidylsuccinate); diisocyantes, such as hexamethylenediisocyanate; bis oxiranes, such as 1,4 butanediyl diglycidyl ether; dicarboxylic acids, such as succinyldisalicylate; and the like. Heterobifunctional cross-linking agents, which contain a different reactive group at each end, may also be used. Examples of peptide linkers are provided as SEQ ID NOs: 41, 253, and 254.

Applications of PMMA-Binding Peptides

It will be appreciated by the skilled person that PMMA-binding peptides or peptide reagents comprising at least one of the present PMMA-binding peptides may be used in a multiplicity of formats including as delivery means for delivering benefits agents, in assays for diagnostic applications as well as in materials applications for coating PMMA polymer or copolymer surfaces. In one embodiment, a personal care composition comprising one or more of the present PMMA-binding peptides and/or peptide-based reagents is also provided to delivery (or enhance the durability of) a benefit agent to a body surface. Examples of personal care compositions may include coloring or conditioning compositions for the body surface described herein, such as hair, skin, nail, and/or tooth surfaces.

EXAMPLES

It should be understood that these examples, while indicating various embodiments of the invention, are provided for illustration purposes. From the above discussion and the examples provided, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "sec" means second(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "pmol" means picomole(s), "mmol" means millimole(s), "µmole" means micromole(s), "g" means gram(s), "µg" means microgram(s), "mg" means milligram(s), "g" means the gravitation constant, "rpm" means revolution(s) per minute, "pfu" means plaque forming unit, "BSA" means bovine serum albumin, "ELISA" means enzyme-linked immunosorbent assay, "A" means absorbance, "$A_{450}$" means the absorbance measured at a wavelength of 450 nm, "TBS" means Tris-buffered saline, "TBST-X" means Tris-buffered saline containing TWEEN® 20 (CAS#9005-64-5) where "X" is the weight percent of TWEEN® 20, "vol %" means volume percent, TRITON®-X100 is a detergent having CAS#9002-93-1.

General Methods:

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5th Ed. Current Protocols and John Wiley and Sons, Inc., N.Y., 2002.

Materials and Methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989.

All reagents and materials used for the growth and maintenance of bacterial cells were obtained from Aldrich Chemicals (Milwaukee, Wis.), BD Diagnostic Systems (Sparks,

Example 1

Selection of PMMA Polymer-Binding Peptides Using mRNA-Display Biopanning

The purpose of this Example is to demonstrate enrichment and isolation of PMMA-binding peptides using an mRNA display biopanning method.

mRNA-Display Peptide Libraries:

Methods to make libraries of DNA molecules suitable as starting materials for mRNA-display are well-known in the art (see WO2005/051985). The following procedure was used to identify 27-mer peptides that have strong affinity for a PMMA polymer target material.

Briefly, a library of random nucleic acid molecules (ds-DNA) each molecule encoding a peptide of desired length was generated. A linear peptide library containing 81 nucleotide positions or 27 randomized amino acid positions was used ("p27 library"). The p27 library was designed to include appropriate 5' and 3' regions for efficient in vitro transcription, translation, purification, and coupling to the MHA-oligonucleotide linker (MHA is 3'-[α-amino-p-methoxy-hydrocinnamido]-3'-deoxy-adenosine) in the individual molecules.

The DNA encoding the linear peptide library was designed to include a T7 promoter and a tobacco mosaic virus (TMV) translation initiation sequence operably linked to the coding sequence (CDS) (Liu et al., *Methods in Enzymology*, (2000) 318:268-293). The CDS was designed to encode: (1) a constant N-terminal flaking region comprising a hexa-histidine tag followed by a flexible linker (underlined) sequence (MH-HHHHHSGSSSGSGSG; SEQ ID NO: 36), (2) the randomized 27-mer linear peptide, and (3) a constant C-terminal flanking region (TSGGSSGSSLGVASAI; SEQ ID NO: 37) comprising another flexible linker region (bold) and a C-terminal sequence optimized for efficient coupling to the MHA-oligonucleotide linker (double-underlined).

In Vitro Transcription

Double stranded DNA (dsDNA) as result of the PCR reactions were transcribed into RNA using the RIBOMAX™ Express in vitro transcription kit (Promega Corp., Madison, Wis.). After incubation for at least 45 min at 37° C., DNase I was added and the incubation continued at 37° C. for additional 30 minutes to degrade all template DNA. The reaction mixture was purified by phenol/chloroform extraction. Then free nucleotides were removed by gel filtration using G25 microspin columns (Pharmacia Corp.; Milwaukee, Wis.). The concentration of purified RNA was determined by photometry at 260 nm.

Library Preparation:

Approximately 10 pmol of highly purified RNA was produced by in vitro transcription from the p27 DNA library and purified after DNase I digestion (by phenol/chloroform extraction and gel filtration, methods described below). The 3'-end of the p27 library RNA was modified by attachment of a MHA-linker molecule (described above) and translated in vitro by means of a rabbit reticulocyte lysate. Covalent fusion products between peptide and coding RNA were purified on magnetic oligo(dT) beads, reverse transcribed, and again purified on a Ni-NTA purification matrix to remove uncoupled RNA and free peptides. About 8 pmol of peptide-RNA-cDNA-fusions were used as input for the first contact with target material during selection round 1.

Chemical Coupling of RNA and MHA-Oligonucleotide Linker

Purified RNA was annealed (by heat denaturation for 1 minute at 85° C. and cooling down to 25° C. for 10 minutes) with a 1.5-fold excess of MHA-oligonucleotide linker-PEG$_2$A18 (5'-psoralen-UAG CGG AUG C A$_{18}$ (PEG-9)$_2$ CC-MHA [nucleotides shown in italics represent 2'-O-methyl-derivatives] (SEQ ID NO: 38). The covalent coupling was induced by radiation with UV-light (365 nm) for 15 min at room temperature. Aliquots of this reaction mixture before and after irradiation with UV were analyzed on a 6%-TBE-Urea-polyacrylamidgel to control the coupling efficiency (usually at least 60%).

In Vitro Translation and $^{35}$S-Labelling of Peptide-RNA Fusions

Ligated RNA was translated using a rabbit reticulocyte lysate from Promega in presence of 15 µCi $^{35}$S-methionine (1000 Ci/mmole). After a 30 min incubation at 30° C., KCl and MgCl$_2$ were added to a final concentration of 530 mM and 150 mM respectively in order to promote formation of mRNA-peptide-fusions.

Oligo(dT) Purification

For the purification of peptide-RNA-fusions from translation mixtures molecules were hybridized to magnetic oligo (dT) beads (Miltenyi Biotec; Bergisch Gladbach, Germany) in annealing buffer (100 mM Tris-HCl pH 8.0, 10 mM EDTA, 1 M NaCl and 0.25% TRITON® X-100) for 5 min at 4° C. Beads were separated from the mixture using magnetic-activated cell sorting (MiniMACS®-filtration columns; Miltenyi Biotec), repetitively washed with 100 mM Tris-HCl pH 8.0, 1 M NaCl, 0.25% TRITON® X-100 and finally eluted with water. A sample of this reaction was analyzed on 4-20% Tris/glycine-SDS-PAGE; radioactive bands were visualized using a PhosphoroImager.

Reverse Transcription (RT)

The RNAs of Oligo(dT)-purified peptide-RNA-fusions were reverse transcribed using SUPERSCRIPT™ II Reverse Transcriptase (Invitrogen, Carlsbad, Calif.) according to the manufacturer's recommendations. RT reactions contained about 1.5-fold excess of 3'-reverse primer. A sample of this reaction was analyzed on 4-20% Tris/glycine-SDS-PAGE; radioactive bands were visualized using a PhosphorImager.

His-Tag Purification

Reverse transcribed mRNA-peptide-fusion molecules were mixed with Ni-NTA-agarose (QIAGEN; Valencia, Calif.) in HBS buffer (20 mM HEPES (CAS #7365-45-9) pH 7.0, 150 mM NaCl, 0.025% TRITON® X-100, 100 µg/mL sheared salmon sperm DNA, 1 mg/mL bovine serum albumin (BSA)) and incubated for 60 min at room temperature under gentle shaking. Ni-NTA was then filtrated and washed with HNT buffer (20 mM HEPES pH 7.0, 150 mM NaCl, 0.025% TRITON® X-100) containing 5 mM imidazole. Finally peptide-RNA-cDNA-fusions were eluted with 150 mM imidazole in HNT buffer (20 mM HEPES pH 7.0, 150 mM NaCl, 0.025% TRITON® X-100). A sample of this reaction was analyzed on 4-20% Tris/glycine-SDS-PAGE; radioactive bands were visualized using a PhosphorImager. BSA (final concentration 1 mg/mL) and sheared salmon sperm DNA (final concentration 100 µg/mL) were added to the eluates before contacting with target materials during selection step.

Selection by Binding to Target Materials and Washing

A. Incubation of Peptide-RNA-cDNA-Fusion Library with Target Material:

Purified peptide-RNA-cDNA-fusions (PROFUSION™ molecules; Adnexus Therapeutics, Waltham, Mass.) after Ni-NTA purification were incubated for 60 minutes at room temperature in 1 mL (final volume) of 20 mM HEPES, pH 7.4, 150 mM NaCl, 1 mg/mL BSA, 100 µg/mL sheared salmon sperm DNA, 0.025% TRITON® X-100 in presence of DEPC-treated (diethylpyrocarbonate), blocked target material. Input activity of purified peptide-RNA-cDNA-fusions was determined by scintillation measurement.

B. Washing:

Non-binding variants were washed away by one of the following washing procedures listed below:

Washing procedure A: used for washing the target material during selection round 1:
5×5 sec. each with HNTriton buffer (20 mM HEPES, pH 7.4, 150 mM NaCl, 0.025% TRITON®-X100)
1×5 sec 150 mM NaCl (for buffer removal before elution with KOH)

Washing procedure C: used for washing of target material during selection round 2-7:
2×5 sec. each with HNTween buffer (20 mM HEPES, pH 7.4, 150 mM NaCl, 0.5% Tween-20)
1×5 min. with 10% shampoo in HNTriton buffer
1×5 sec with HNTween buffer including tube change
1×5 min with 10% shampoo in HNTriton buffer
3×5 sec with HNTween buffer; 1 tube change during the third wash
1×5 sec 150 mM NaCl (for buffer removal before elution with KOH)

Washing procedure E: used for washing target material in round 8b:
2×5 sec each with HNTween buffer (20 mM HEPES, pH 7.4, 150 mM NaCl, 0.5% TWEEN®-20)
4×30 min. with 10% shampoo in HNTriton buffer
1×5 sec with HNTween buffer including tube change
3×5 sec with HNTween buffer; 1 tube change during the third wash
1×5 sec 150 mM NaCl (for buffer removal before elution with KOH)

Washing procedure G: used for washing of target material in rounds 9b and 10b:
2×5 sec each with HNTween buffer (20 mM HEPES, pH 7.4, 150 mM NaCl, 0.5% TWEEN®-20)
1×5 min. with 10% shampoo in HNTriton buffer
1×5 sec with HNTween buffer including tube change
4×30 min with 10% shampoo in HNTriton buffer
1× overnight with 10% shampoo in HNTriton buffer
3×5 sec with HNTween buffer; 1 tube change during the third wash
1×5 sec 150 mM NaCl (for buffer removal before elution with KOH)

The shampoo used in the above washing procedures was a commercially available hair shampoo having the following composition:

| Water | 51% |
| Ammonium lauryl sulfate | 20% |
| Sodium lauryl ether sulfate | 15% |
| Cocamidopropyl betaine | 7% |
| Cocamide MEA | 2.5% |
| Miscellaneous minor components** | ~4.5% |

**(e.g. various pH adjusters, preservatives, vitamins, chelating agents, dispersants, lubricants, fragrances, and dyes)

Comment on Incubation and Washing Conditions:

Normally during mRNA display selections a low detergent concentration is chosen to have low stringent conditions during up to 6 rounds of selection by keeping the detergent concentration at 0.025% TRITON®-X100. However, a higher stringency for the target material was applied from the beginning during incubation and washing (see washing procedures). The applied high concentrations of TWEEN®-20 and shampoo are close to the so called "critical micelle concentration" (CMC) allowing the formation of small micelles which might contain more than one peptide-RNA-cDNA-fusion. Since CMC driven aggregation of peptide-RNA-cDNA-fusions are critical for successful selections, higher concentrations of the detergents described above were not used.

cDNA Elution:

cDNAs of binding variants were eluted by incubation of target material in 50 μL of 100 mM KOH at 60° C. for 30 minutes. After centrifugation, supernatant was removed from target material and transferred into a fresh tube. KOH eluates were subsequently neutralized by addition of 1 μL of 1 M Tris/HCl, pH 7.0 and 3.8 μL of 1 M HCl (per 50 μL 100 mM KOH).

Polymerase Chain Reaction (PCR):

After elution in KOH and neutralization, the recovered cDNAs were amplified by quantitative PCR with increasing numbers of amplification cycles (12, 15, 18, 21, 24 and 27 cycles). Products were subsequently analyzed by agarose gel electrophoresis over 2% agarose gels. Optimized conditions (minimal cycle number to get good enrichment of DNA of correct length) were then applied for a preparative PCR reaction and controlled again by agarose gel electrophoresis.

Analytical and preparative PCR reactions were performed in presence of 10 mM Tris-HCl (pH 8.8 at 25° C.), 50 mM KCl, 0.08% Nonidet P40, 2 mM $MgCl_2$, 2.5 mM dNTPs, 1 μM of each forward and reverse primer (5'-TAATACGACT-CATAGGGACAATTACTATTTACAA TTACAATG-3'; SEQ ID NO: 39) and (5'-AATTAAATAGCGGATGCTA-CACCAAGACTAGAACCGCTG-3'; SEQ ID NO: 40), ⅕ volume of neutralized cDNA eluate and 0.05 U/μL Taq polymerase (Promega Corp.). Temperature program of PCR reaction is given below: Initial denaturation: 90 sec at 94° C.; cycling: 15 sec at 94° C. (denaturation), 20 sec at 60° C. (annealing), 30 sec at 72° C. (extension); post treatment: 3 min at 72° C. (post-treatment); hold at 4° C.

Enrichment of cDNA-RNA-Peptide Fusion Molecules Binding to PMMA

Ten rounds of selection were conducted and the relative binding of radioactively labeled cDNA-RNA-peptide fusion molecules to the PMMA polymer target material was measured. The amount of PMMA polymer (acrylic glass; PLEXI-GLAS® VS100 [Altuglas International Arkema Inc., Philadelphia, Pa.], used was once cylinder shaped PMMA pellet per selection divided into 4 quarters corresponding to approximately 27.4 mg.

Round 1 selection used washing procedure A as described above. Rounds 2-10 used various washing procedures with increased washing stringencies (see Table 1). The relative amount of enrichment (reported as percent enrichment of binding molecules relative to their respective input signals [activity of cDNA-RNA-peptide fusions before contacting with the target material]) is provided in Table 1.

TABLE 1

Relative binding of radioactive-labeled peptide-RNA-cDNA-fusions on PMMA polymer during increasing rounds of mRNA display selection:

| Selection Round | Washing Procedure | % Enrichment of cDNA-RNA-peptide fusion molecules having affinity for PMMA polymer |
|---|---|---|
| R1 | A | 0.00 |
| R2 | C | 0.23 |
| R3 | C | 0.04 |

TABLE 1-continued

Relative binding of radioactive-labeled peptide-RNA-cDNA-fusions on PMMA polymer during increasing rounds of mRNA display selection:

| Selection Round | Washing Procedure | % Enrichment of cDNA-RNA-peptide fusion molecules having affinity for PMMA polymer |
|---|---|---|
| R4 | C | 0.09 |
| R5 | C | 0.57 |
| R6 | C | 1.94 |
| R7 | C | 2.80[a] |
| R8b | E | 2.80 |
| R9b | G | 1.47[a] |
| R10b | G | 0.08[a] |

[a] = processed for sequencing

Sequencing of 27-mer PMMA-Binding Peptides

The cDNA molecules from the enriched pool of PMMA-binding fusion molecules were isolated and PCR amplified as described above. The sequences of the DNA molecules encoding the PMMA-binding peptides isolated after rounds 7, 9b and 10b of selection were determined (~30 samples each). The corresponding amino acid sequences of the PMMA-binding peptides are provided in Tables 2 (a-h). Several samples were identified encoding an identical or nearly identical amino acid sequence. Amino acid resides that vary between individual members with a specified group are in bold (Groups "A" through "G").

TABLE 2a

Amino Acid Sequences of Selected PMMA-binding Peptides Sharing Group "A" Structure

| Peptide Sample Numbers | Number Observed | Amino acid sequence | SEQ ID NO: |
|---|---|---|---|
| Round 7 samples: 15, 19, 28, 21, 23, 27, 2, 6, 1, 9; Round 9b samples: 22, 10, 14, 21, 17, 9; Round 10b sample 6 | 17 | FLHGLIHGWYSLWMWMLSWPYMVWWVF | 1 |
| Round 7 sample 26 | 1 | FLHGLIHGWYSLWMWILSWPYMVWWVF | 2 |
| Round 9b sample 4 | 1 | FMHGLIHGWYSLWMWMLSWPYMVWWVF | 3 |
| Round 7 sample 20 | 1 | FLHGLIHGWYSLWMWMLSWPYMVWWVL | 4 |
| Group "A" Sequence | — | FXHGLIHGWYSLWMWXLSWPYMVWWVX | 5 |

TABLE 2b

PMMA-binding Peptides Group "B" Structure

| Peptide Sample Numbers | Number Observed | Amino acid sequence | SEQ ID NO: |
|---|---|---|---|
| Round 7 samples 16, 17, 22, 8, 12, 7, and 3; Round 10b sample 5 | 8 | GWQRIWQSILCWMYFPLCLWMEWYRAI | 6 |
| Round 7 sample 24 | 1 | GWQRIWQSILCWMYLPLCLWMEWYRAI | 7 |
| Round 7 sample 25 | 1 | GWQRIWQSIFCWMYFPLCLWMEWYRAI | 8 |
| Group "B" Sequence | — | GWQRIWQSIXCWMYXPLCLWMEWYRAI | 9 |

TABLE 2c

PMMA-binding Peptides Group "C" Structure

| Peptide Sample Numbers | Number Observed | Amino acid sequence | SEQ ID NO: |
|---|---|---|---|
| Round 7 samples 4, 5; Round 9b samples 7, 15, 16 | 5 | GSETYLYWSWWWLYLWYWPFWYMWAGM | 10 |
| Round 10b Sample 3 | 1 | GSETYLYWSWWWLYLWYWPFWYVWAGM | 11 |
| Round 7 Sample 13 | 1 | GSETYLYWSWCWLYLWYWPFRYMWAGM | 12 |
| Round 7 sample 10 | 1 | GSETYLYWSWWWLYSWYWPFWYMWAGM | 13 |
| Group "C" Sequence | — | GSETYLYWSWXWLYXWYWPFXYXWAGM | 14 |

TABLE 2d

PMMA-binding Peptides Sharing Group "D" Structure

| Peptide Sample Numbers | Number Observed | Amino acid sequence | SEQ ID NO: |
|---|---|---|---|
| Round 7 Sample 30; Round 9b Samples 11, 12, 8, 9 | 5 | MWHGLWLWMALYWWMTWSWFLWPFRVI | 15 |
| Round 9b Sample 6; Round 10b Sample 1 | 2 | MWHGLWLWMALYWWMTWSWFLWPFWVI | 16 |
| Round 10b Sample 10 | 1 | MWYGLWLWMALYWWMTWSWFLWPFRVI | 17 |
| Group "D" Sequence | — | MWXGLWLWMALYWWMTWSWFLWPFXVI | 18 |

TABLE 2e

PMMA-binding Peptides Sharing Group "E" Structure

| Peptide Sample Numbers | Number Observed | Amino acid sequence | SEQ ID NO: |
|---|---|---|---|
| Round 9b Sample 19 | 1 | IGWWLLRYWLYLQWKLYVWWFSVLWTF | 19 |

TABLE 2e-continued

PMMA-binding Peptides Sharing Group "E" Structure

| Peptide Sample Numbers | Number Observed | Amino acid sequence | SEQ ID NO: |
|---|---|---|---|
| Round 9b Sample 8 | 1 | IGWWLLRYWLYLQWKLYAWW FSVLWTF | 20 |
| Group "E" Sequence | — | IGWWLLRYWLYLQWKLYXWW FSVLWTF | 21 |

TABLE 2f

PMMA-binding Peptides Sharing Group "F" Structure

| Peptide Sample Number | Number Observed | Amino acid sequence | SEQ ID NO: |
|---|---|---|---|
| Round 9 Samples 3, 20 | 2 | RLDSWIFQTWLMWIWMVWPWLWP FWWL | 22 |
| Round 10b Sample 4 | 1 | LDSWIFQTWLMWIWMVWPWLWPF WWL | 23 |
| Group "F" Sequence | — | XLDSWIFQTWLMWIWMVWPWLWP FWWL | 24 |

TABLE 2g

PMMA-binding Peptides Sharing Group "G" Structure

| Peptide Sample Numbers | Number Observed | Amino acid sequence | SEQ ID NO: |
|---|---|---|---|
| S15R9b_2 | 1 | VWWTFFGWFYWLWAMWWN VSLALWEWV | 25 |
| S15R10b_7 | 1 | VWWAFFGWFYWLWAMWWN VSLALWEWV | 26 |
| Group "G" Sequence | — | VWWXFFGWFYWLWAMWWN VSLALWEWV | 27 |

TABLE 2h

Additional PMMA-binding Peptides

| Peptide Sample Numbers | Number Observed | Amino acid sequence | SEQ ID NO: |
|---|---|---|---|
| Round 7 Sample 11 | 1 | VVPLMWVYWWVFMWGWPMVFW YTWWAA | 28 |
| Round 7 Sample 14 | 1 | FSSRDFLGYWISWLMWPYFVL WRWLMH | 29 |
| Round 7 Sample 29 | 1 | RSGLKRKVLRHVWTVMWTMGS WLHGSL | 30 |
| Round 9b Sample 18 | 1 | FWYGLWLFWWWHTWFVWRTLW YWMVWL | 31 |
| Round 9b Sample 13 | 1 | TLWTFYWLSWAWYMPLWPWWL YWLMWG | 32 |
| Round 9b Sample 15 | 1 | LLWLFWWPWLWWLCVTQWSYE MGMGWW | 33 |
| Round 9b Sample 1 | 1 | HFWAWYIEWLRWYLYVPLWFR WFVGF | 34 |

TABLE 2h-continued

Additional PMMA-binding Peptides

| Peptide Sample Numbers | Number Observed | Amino acid sequence | SEQ ID NO: |
|---|---|---|---|
| Round 10b Sample 2 | 1 | YVLFFMAVWWPWWLLMWIWQN LMTMTT | 35 |

Example 2

Confirmation of PMMA-Binding Affinity

The purpose of this Example was to confirm the affinity of at least one PMMA-binding peptide identified by mRNA-display for a PMMA resin surface, measured as $MB_{50}$ values, using an ELISA assay to confirm that selection process produced PMMA-binding peptides with strong affinity for PMMA polymer resin.

The peptide was synthesized using a standard solid phage synthesis method and was biotinylated by adding a biotinylated lysine residue at the C-terminus of the amino acid binding sequence for detection purposes. The peptide tested was SEQ ID NO: 6 (referred to herein as "CPXB"). A C-terminal biotinylated lysine was added to the SEQ ID NO: 6; provided separately herein as SEQ ID NO: 257.

The $MB_{50}$ measurement of the biotinylated peptide binding to PMMA was done using PMMA polymer resin from Bangs Laboratories, Inc. The polymethyl methacrylate (dry) particles were 140 µm in diameter. Each teat-tube contains 1 mg of the particles and three tubes for peptide concentration (from 1 to 1,000 µM). The PMMA resin sample was incubated in SUPERBLOCK® blocking buffer (Pierce Chemical) for 1 hour at room temperature (~22° C.), followed by 3 washes with TBST (TBS in 0.05% TWEEN® 20). Peptide binding buffer consisting of various concentrations of biotinylated peptide in TBST and 1 mg/mL BSA was added to the PMMA polymer samples and incubated for 1 hour at room temperature, followed by 6 TBST washes. Then, the streptavidin-horseradish peroxidase (HRP) conjugate (Pierce Chemical Co., Rockford, Ill.) was added to each well (1.0 µg per well), and incubated for 1 h at room temperature, followed by 6 times of washes with TBST. All samples were transferred to new tubes and the chromogenic agent ABTS (2,2'-azino-bis(3-ethylbenzthiazoline-6-sulphonic acid)) was added. The color development and the absorbance measurements were performed following the manufacturer's protocol. The plates were read at $A_{405}$ nm. The results were plotted as $A_{405}$ versus the concentration of peptide using GraphPad Prism 4.0 (GraphPad Software, Inc., San Diego, Calif.). The $MB_{50}$ value was calculated from Scatchard plots and is shown Table 3.

The very low $MB_{50}$ value measured for CPXB verifies that PMMA-binding peptide sequences identified by mRNA-display should have strong affinity for PMMA resin.

TABLE 3

$MB_{50}$ Value for PMMA-binding peptide CPXB

| Peptide ID NO. | Peptide Sequence | $MB_{50}$ (M) |
|---|---|---|
| CXPB | PLWRRITKRKLVRPVATLMWYWFTSKRK-(biotin)-NH$_2$ (SEQ ID NO: 257) | $2.5 \times 10^{-8}$ |

What is claimed is:

1. An isolated peptide having affinity for polymethyl methacrylate polymer (PMMA-binding peptide), said peptide having the general structure:

IGWWLLRYWLYLQWKLYX$_1$WWFSVLWTF;  (SEQ ID NO: 21)

wherein X$_1$ is V or A.

2. A peptide-based reagent having a general structure selected from the group consisting of:

([PBP]$_n$-[L]$_x$-BA-[L]$_y$)$_m$; and ([PBP]$_n$-[L]$_x$-TBD-[L]$_y$)$_m$ wherein:
- i) PBP is the peptide of claim 1 having affinity for polymethyl methacrylate polymer;
- ii) L is a linker molecule;
- iii) BA is at least one benefit agent;
- iv) TBD is a target binding domain;
- v) x and y are independently 0 or 1;
- vi) n=1 to 10; and
- vii) m=1 to 10.

3. The peptide-based reagent according to claim 2 wherein the linker molecule is a peptide linker ranging from 1 to 50 amino acids in length.

4. The peptide-based reagent according to claim 2 wherein the benefit agent is selected from the group consisting of pharmaceuticals, markers, colorants, conditioners, fragrances, and antimicrobial agents.

5. The peptide-based reagent according to claim 2 wherein the target binding domain is a body surface binding domain comprising at least one peptide having affinity for a body surface selected from the group consisting of hair, skin, nails and teeth.

6. A method for binding a peptide-based reagent to polymethyl methacrylate (PMMA) comprising:
- a) providing the peptide-based reagent according to claim 2; and
- b) contacting the peptide-based reagent of (a) with a surface comprising PMMA whereby the peptide reagent binds to the PMMA.

7. A personal care composition comprising the peptide of claim 1 or the peptide-based reagent of claim 2.

* * * * *